United States Patent
Kashiba et al.

(10) Patent No.: US 9,994,382 B2
(45) Date of Patent: *Jun. 12, 2018

(54) OXYGEN-ABSORBING MEDICAL MULTILAYER CONTAINER AND METHOD FOR STORING BIOLOGICAL MEDICINE

(71) Applicant: MITSUBISHI GAS CHEMICAL COMPANY, INC., Tokyo (JP)

(72) Inventors: Takashi Kashiba, Kanagawa (JP); Shun Ogawa, Kanagawa (JP); Shota Arakawa, Kanagawa (JP); Kenichiro Usuda, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 348 days.

This patent is subject to a terminal disclaimer.

(21) Appl. No.: 14/767,114

(22) PCT Filed: Mar. 6, 2014

(86) PCT No.: PCT/JP2014/055877
§ 371 (c)(1),
(2) Date: Aug. 11, 2015

(87) PCT Pub. No.: WO2014/136918
PCT Pub. Date: Sep. 12, 2014

(65) Prior Publication Data
US 2015/0368023 A1    Dec. 24, 2015

(30) Foreign Application Priority Data

Mar. 6, 2013  (JP) ................... 2013-044734
Mar. 6, 2013  (JP) ................... 2013-044737
Mar. 6, 2013  (JP) ................... 2013-044740
Mar. 6, 2013  (JP) ................... 2013-044754
Mar. 6, 2013  (JP) ................... 2013-044755

(51) Int. Cl.
*B65D 81/26* (2006.01)
*A61J 1/14* (2006.01)
(Continued)

(52) U.S. Cl.
CPC .......... *B65D 81/266* (2013.01); *A61J 1/1468* (2015.05); *B32B 27/08* (2013.01); *B32B 27/18* (2013.01); *B32B 27/32* (2013.01); *B32B 27/34* (2013.01); *B32B 27/36* (2013.01); *B65D 11/20* (2013.01); *A61J 1/10* (2013.01); *A61M 5/3129* (2013.01); *B32B 2250/00* (2013.01);
(Continued)

(58) Field of Classification Search
CPC ...... B65D 81/266; B65D 11/20; A61J 1/1468; B32B 27/08; B32B 27/36; B32B 27/34; B32B 27/32; B32B 27/18; B32B 2250/00; B32B 2553/00; B32B 2250/05; B32B 2250/02; B32B 2307/54; A61M 5/3129

USPC ......... 252/188.28, 194, 184, 182.28, 188.25, 252/397, 182.17, 188.1, 400.3, 400.53, 252/408.1, 182.1, 182.16, 186.24, 188.2, 252/188.21, 2, 364, 373, 398, 400.1, 252/400.2, 400.52, 405, 407, 586, 588, 252/589, 67, 68, 8.83; 506/9, 2, 39, 35, 506/12, 38, 7, 10, 11, 17, 18, 23, 26, 33, 506/4, 40, 8; 428/35.7, 36.6, 35.2, 35.8, 428/36.92, 523, 336, 34.1, 483, 516, 428/423.1, 474.7, 500, 220, 34.9, 35.4, 428/36.7, 411.1, 451, 457, 474.4, 475.2, 428/515, 520, 137, 141, 201, 316.6, 323, 428/34.2, 35.9, 402, 446, 476.3, 476.9, 428/480, 518, 522, 702, 76, 81, 142, 146, 428/147, 149, 156, 159, 189, 195.1, 198, 428/209, 210, 211.1, 212, 216, 219, 428/315.9, 32.39, 332, 335, 338, 339, 428/343, 349, 34.5, 34.7, 354, 35.3, 36.1, 428/36.4, 36.91, 391, 408, 412, 413, 428/424.2, 425.5, 425.9, 426, 429, 430, 428/447, 448, 450, 458, 461, 472, 475.8, 428/484.1, 512

See application file for complete search history.

(56) References Cited

U.S. PATENT DOCUMENTS 5,346,644 A      9/1994  Speer et al.
2001/0016670 A1  8/2001  Murata et al.
(Continued)

FOREIGN PATENT DOCUMENTS

CN  104582831   4/2015
JP  51-136845   11/1976
(Continued)

OTHER PUBLICATIONS

Atsushi (JP2008050403A, Atasushi, et al., machine translation, p. 1-25).*

(Continued)

*Primary Examiner* — James C Yager
*Assistant Examiner* — Kevin C Ortman, Jr.
(74) *Attorney, Agent, or Firm* — Greenblum & Bernstein, P.L.C.

(57) ABSTRACT

Provided is an oxygen-absorbing medical multilayer container including at least three layers including a first resin layer containing a thermoplastic resin (b1), an oxygen-absorbing layer containing an oxygen-absorbing composition, and a second resin layer containing a thermoplastic resin (b2), in this order, where the oxygen-absorbing composition contains at least one compound having a tetralin ring represented by Formula (1), a transition metal catalyst, and a thermoplastic resin (a).

14 Claims, No Drawings

(51) Int. Cl.
  *B65D 6/00* (2006.01)
  *B32B 27/18* (2006.01)
  *B32B 27/08* (2006.01)
  *B32B 27/32* (2006.01)
  *B32B 27/34* (2006.01)
  *B32B 27/36* (2006.01)
  *A61J 1/10* (2006.01)
  *A61M 5/31* (2006.01)

(52) U.S. Cl.
  CPC ....... *B32B 2250/02* (2013.01); *B32B 2250/05* (2013.01); *B32B 2307/412* (2013.01); *B32B 2307/54* (2013.01); *B32B 2307/7244* (2013.01); *B32B 2439/80* (2013.01); *B32B 2553/00* (2013.01)

(56) References Cited

U.S. PATENT DOCUMENTS

| | | | |
|---|---|---|---|
| 2002/0133119 A1* | 9/2002 | Eakins | A61M 5/3134 604/111 |
| 2003/0012896 A1 | 1/2003 | Ching et al. | |
| 2004/0267194 A1 | 12/2004 | Sano et al. | |
| 2005/0142373 A1 | 6/2005 | Komatsu et al. | |
| 2007/0036923 A1 | 2/2007 | Ishizaki et al. | |
| 2008/0241521 A1 | 10/2008 | Solovyov et al. | |
| 2009/0162675 A1 | 6/2009 | Bourgeois | |
| 2011/0172335 A1* | 7/2011 | Deshpande | C08K 5/3417 524/94 |
| 2013/0145962 A1* | 6/2013 | Gupta | C08K 5/1545 106/287.21 |
| 2013/0284617 A1 | 10/2013 | Yamada et al. | |
| 2015/0232251 A1 | 8/2015 | Ikeda et al. | |
| 2015/0368022 A1 | 12/2015 | Okada et al. | |

FOREIGN PATENT DOCUMENTS

| | | | |
|---|---|---|---|
| JP | 1-259870 | | 10/1989 |
| JP | 2-500846 | | 3/1990 |
| JP | 5-115776 | | 5/1993 |
| JP | 7-39329 | | 2/1995 |
| JP | 8-127641 | | 5/1996 |
| JP | 8-133345 | | 5/1996 |
| JP | 9-234832 | | 9/1997 |
| JP | 2000-319207 | | 11/2000 |
| JP | 2001-233809 | | 8/2001 |
| JP | 2001-252560 | | 9/2001 |
| JP | 2003-521552 | | 7/2003 |
| JP | 2004-229750 | | 8/2004 |
| JP | 2008050403 A | * | 3/2008 |
| JP | 2009-108153 | | 5/2009 |
| JP | 2011-212447 | | 10/2011 |
| WO | 89/01012 | | 2/1989 |
| WO | 99/48963 | | 9/1999 |
| WO | 2004/018556 | | 3/2004 |
| WO | 2005/105887 | | 11/2005 |
| WO | 2012/102086 | | 8/2012 |
| WO | 2014/034800 | | 3/2014 |

OTHER PUBLICATIONS

Search Report issued by International Bureau of WIPO, Application No. PCT/JP2014/055877 patent office in International Bureau of WIPO, Application No. PCT/JP2014/055877 Patent Application No. , dated Jun. 10, 2014.

International Preliminary Examination Report in PCT/JP2014/055877, dated Sep. 8, 2015.

Office Action from U.S. Appl. No. 14/766,562 (published as US 2015/0368022 A1), dated Dec. 1, 2017.

* cited by examiner

OXYGEN-ABSORBING MEDICAL MULTILAYER CONTAINER AND METHOD FOR STORING BIOLOGICAL MEDICINE

TECHNICAL FIELD

The present invention relates to an oxygen-absorbing medical multilayer container, and a method for storing biological medicine.

BACKGROUND ART

In order to prevent oxygen oxidation of various types of articles that are easily deteriorated or degraded by oxygen, such as foods, beverages, medicinal products, and cosmetics, and to store them for a long time, oxygen absorbers are used for removing oxygen inside the packaging bodies accommodating these articles.

As the oxygen absorber, an oxygen absorber including an iron powder as the base reactive compound is generally used because of its oxygen-absorbing ability, easiness in handling, and safety. The iron-based oxygen absorber is, however, responsive to a metal detector, and it is therefore difficult to use a metal detector for inspection of foreign matters. Furthermore, packaging bodies containing iron-based oxygen absorbers cannot be heated by a microwave oven because of a risk of ignition. Moreover, since the oxidation reaction of an iron powder needs water, the oxygen-absorbing effect is exhibited only when moisture-rich articles are stored.

Packaging containers and other containers having improved gas barrier properties and an oxygen-absorbing function have been developed by making the containers by a multilayer material including an oxygen-absorbing layer of an oxygen-absorbing resin composition composed of a thermoplastic resin and an iron-based oxygen absorber blended therein (see Patent Literature 1). Specifically, the oxygen-absorbing multilayer film includes an oxygen-absorbing layer disposed between the layers of a conventional gas barrier multilayer film composed of a heat sealing layer and a gas barrier layer, with an intermediate layer of a thermoplastic resin between the oxygen-absorbing layer and each of the layers of the conventional gas barrier multilayer film, depending on the case. The oxygen-absorbing layer is a thermoplastic resin layer dispersing an oxygen absorber therein. The oxygen-absorbing multilayer film is used as a film having the function of absorbing oxygen inside a container in addition to the function of preventing oxygen permeation from the outside and is produced by a known production method, such as extrusion lamination, coextrusion lamination, or dry lamination. However, this oxygen-absorbing multilayer film also similarly has disadvantages: The multilayer film is detected by a metal detector for foreign matter inspection of foods, etc., cannot be heated by a microwave oven, and shows the effect only on moisture-rich articles to be stored. The oxygen-absorbing multilayer film also has a disadvantage of insufficient internal visibility due to its opacity. An oxygen-absorbing multilayer film containing an oxygen absorber such as an iron powder has disadvantages: The multilayer film is detected by a metal detector for foreign matter inspection of foods, etc., has insufficient internal visibility due to its opacity, and reduces flavor when the contents are alcoholic beverage due to generation of aldehyde by oxidation reaction of alcohol using iron as a catalyst.

In the aforementioned circumstances, an oxygen absorber including an organic material as a base reactive compound has been demanded. An oxygen absorber including ascorbic acid as the base compound is known as an oxygen absorber including an organic material as a base reactive compound (see Patent Literature 2).

Meanwhile, an oxygen-absorbing resin composition composed of a resin and a transition metal catalyst is known. For example, a resin composition composed of a polyamide as an oxidizable organic component, in particular, a xylylene group-containing polyamide, and a transition metal catalyst is known (see, Patent Literatures 3 and 4). Patent Literatures 3 and 4 exemplify oxygen absorbers, packaging materials, and multilayer laminate films for wrapping prepared by molding such resin compositions.

An oxygen-absorbing resin composition composed of a resin having a carbon-carbon unsaturated bond and a transition metal catalyst is also known as an oxygen-absorbing resin composition not requiring moisture for absorbing oxygen (see Patent Literature 5).

Furthermore, a composition composed of a polymer containing a substituted cyclohexene functional group or a low molecular-weight substance bonded to the cyclohexene functional group and a transition metal is known as a composition for trapping oxygen (see Patent Literature 6).

Meanwhile, injection molding can produce a molded product having a complicated shape and also has high productivity and is therefore widely diffused in production, for example, machine parts, automobile parts, electric/electronic parts, and containers for foods and medicines. Recently, a variety of types of plastic containers have been widely used as packaging containers because of their advantages such as lightness, transparency, and easiness in molding. As typical plastic containers, for example, injection-molded products having a screw shape at the mouth stopper so that the lid can be sufficiently fastened have been widely employed in containers for beverages.

Examples of the material used in the injection-molded product may include generic thermoplastic resins such as polyolefins (e.g., polyethylene and polypropylene), polyesters, and polystyrenes. In particular, injection-molded products mainly composed of polyesters such as poly(ethylene terephthalate) (PET) are widely used as plastic containers for beverages such as tea, fruit juice beverages, carbonated beverages, and alcoholic beverages. Although injection-molded products mainly composed of thermoplastic resins are excellent as packaging materials, they apt to allow oxygen to permeate from the outside, unlike glass bottles and metal containers, and therefore have a problem in the performance of storing contents packaged in a hermetically closed condition. Accordingly, in order to provide a gas barrier property to such an injection-molded product of a generic resin, injection-molded products each having a gas barrier layer as an intermediate layer have been practically used.

Incidentally, for example, glass ampoules, vials, and prefilled syringes have been conventionally used as medical packaging containers for packaging and storing drug solutions in a hermetically closed condition. These glass containers, however, have problems: sodium ions and other components elute into the solution of the contents inside the container during storage; micro substances called flakes occur; when a light-shielding glass container colored with a metal is used, the contents are contaminated by the metal for coloring; and the container is easily broken by a shock such as falling. In addition to these problems, since glass containers have a relatively large specific gravity, medical packaging containers are disadvantageously heavy. Therefore, development of alternate materials has been demanded.

Specifically, plastics lighter than glass, for example, polyester, polycarbonate, polypropylene, and cycloolefin polymers, have been investigated as glass alternatives.

For example, a medical container made of a polyester-based resin material has been proposed (see Patent Literature 7).

Meanwhile, a plastic multilayer container including a gas barrier layer as an intermediate layer for providing a gas barrier property to the container has been investigated. Specifically, a prefilled syringe including the innermost layer and the outermost layer of a polyolefin-based resin and an intermediate layer of a resin composition having an excellent oxygen barrier property and thereby having an enhanced oxygen barrier property has been proposed (see Patent Literature 8). Furthermore, a multilayer container prepared by laminating a gas barrier layer on a resin layer has been investigated, where the gas barrier layer is made of, for example, a polyamide prepared from metaxylylenediamine and adipic acid (hereinafter, may be referred to as "nylon MXD6"), an ethylene-vinyl alcohol copolymer, polyacrylonitrile, poly(vinylidene chloride), aluminum foil, a carbon coat, or a vapor-deposited inorganic oxide.

Furthermore, in recent years, nylon MXD6 provided with an oxygen-absorbing function by being mixed with a small amount of a transition metal compound has been proposed to be used as an oxygen barrier material constituting containers or packaging materials (see Patent Literature 9).

Furthermore, examples of the medical container may include artificial kidney hemodialyzers (dialyzers), in addition to ampoules, vials, and syringes. For the housing of a dialyzer, transparent plastic allowing the contents to be well seen from the outside, such as polystyrene or polycarbonate, is used, and polycarbonate having excellent shock resistance is more preferably used in order to avoid breakage due to falling or other shocks (see Patent Literature 10).

PATENT LITERATURE

Patent Literature 1: Japanese Patent Laid-Open No. H09-234832
Patent Literature 2: Japanese Patent Laid-Open No. S51-136845
Patent Literature 3: Japanese Patent Laid-Open No. 2001-252560
Patent Literature 4: Japanese Patent Laid-Open No. 2009-108153
Patent Literature 5: Japanese Patent Laid-Open No. H05-115776
Patent Literature 6: National Publication of International Patent Application No. 2003-521552
Patent Literature 7: Japanese Patent Laid-Open No. H08-127641
Patent Literature 8: Japanese Patent Laid-Open No. 2004-229750
Patent Literature 9: Japanese Patent Laid-Open No. H02-500846
Patent Literature 10: Japanese Patent Laid-Open No. H01-259870

SUMMARY OF THE INVENTION

Problems to be Solved by the Invention

Unfortunately, the oxygen absorber in Patent Literature 2 has disadvantages: The oxygen-absorbing performance is intrinsically low; the effect is expressed only when moisture-rich articles are stored; and the cost is relatively high.

The resin composition in Patent Literature 3 expresses an oxygen-absorbing function by oxidizing a xylylene group-containing polyamide resin in the presence of a transition metal catalyst, and thereby has a disadvantage, i.e., occurrence of cleavage of the polymer chain by oxidation degradation of the resin after oxygen absorption, resulting in a reduction in the strength of the packaging container itself. This resin composition also has disadvantages that the oxygen-absorbing performance is still insufficient and that the effect is expressed only when moisture-rich articles are stored. Patent Literature 4 describes a method for preventing peeling of the interlayer, but the effect is restrictive. This resin composition also has disadvantages that the oxygen-absorbing performance is still insufficient and that the effect is expressed only when moisture-rich articles are stored.

The oxygen-absorbing resin composition in Patent Literature 5 has, as in above, the problem of generation of a low molecular-weight organic compound, which becomes an odorous component, due to cleavage of the polymer chain by oxidation of the resin, resulting in occurrence of an odor after oxygen absorption.

The composition in Patent Literature 6 needs to contain a special material having a cyclohexene functional group. This material still has a disadvantage of relatively easily causing occurrence of an odor.

The conventional gas barrier multilayer container and the medical multilayer container mentioned above are insufficient in the basic performance, such as oxygen barrier property, water vapor barrier property, drug solution adsorptivity, and durability of the container. Therefore, improvement is required from the viewpoint of the performance of storing contents, such as a drug solution or a food.

In particular, when a food or a drug solution is stored in a conventional gas barrier multilayer container, the fact is that complete removal of oxygen in a packaging container is difficult or significantly uneconomical even if any gas replacement is operated. In other words, it is difficult to completely eliminate oxygen, such as oxygen dissolved in a solution as the contents, oxygen contained in air bubbles generated and introduced during mixing of the contents, and oxygen dissolved in water in a case of adding water to the contents. Although oxygen can be removed as much as possible by strictly controlling the conditions for selection and preparation of raw materials and the conditions in production, such an operation ignoring an economic aspect is unrealistic. In addition, as described above, the oxygen barrier property of the gas barrier multilayer container is insufficient, and a small amount of oxygen penetrating from outside through the wall of the container cannot be completely eliminated.

For example, although the medical container made of a polyester-based resin of Patent Literature 7 has a relatively excellent oxygen barrier property, the oxygen barrier property is insufficient for completely blocking oxygen, and the water vapor barrier property is inferior to that of a container made of a polyolefin-based resin. In addition, since the polyester-based resin does not have oxygen-absorbing performance, the medical container has the problem of being impossible to prevent a degradation of the drug solution inside the container, if oxygen penetrates into the container from the outside or if oxygen remains in the head space above the contents inside the container.

Although the prefilled syringe of Patent Literature 8 has relatively excellent oxygen barrier property and water vapor barrier property, the oxygen barrier property is insufficient for completely blocking oxygen. In addition, the oxygen barrier resin composition in the intermediate layer does not have oxygen-absorbing performance. Thus, the prefilled syringe has the problem of being impossible to prevent a degradation of the drug solution inside the container, if oxygen penetrates into the container from the outside or if oxygen remains in the head space above the contents inside the container.

The resin composition of Patent Literature 9 has the problem of a reduction in strength due to oxidation degradation of the resin after oxidation absorption, resulting in a reduction in the strength of the packaging container itself, as in the resin compositions of Patent Literatures 3 and 4. In addition, this resin composition also has the following problems: the oxygen-absorbing performance is still insufficient and the effect is expressed only when moisture-rich articles are stored.

Although the housing of a dialyzer of Patent Literature 10 has excellent transparency and shock resistance, polycarbonate has an oxygen barrier property and a water vapor barrier property insufficient for application to a container for accommodating and storing a drug solution and therefore has a problem in storage of contents for a long time.

In particular, regarding prefilled syringes, when the above-described known gas barrier multilayer container is used as a prefilled syringe, complete removal of oxygen inside the container is actually difficult or significantly uneconomical even if any gas replacement is operated, for example, during filling with a drug. In other words, it is difficult to completely eliminate oxygen, such as oxygen dissolved in a solution as the contents, oxygen contained in air bubbles generated and introduced during mixing of the contents, and oxygen dissolved in water in a case of adding water to the contents. Although oxygen can be removed as much as possible by strictly controlling the conditions for selection and preparation of raw materials and the conditions in production, such an operation ignoring an economic aspect is unrealistic. In addition, the oxygen barrier property of the gas barrier multilayer container is insufficient, and a small amount of oxygen penetrating from the outside through the wall of the container cannot be completely eliminated.

In such a point, for example, the medical container made of a polyester-based resin of Patent Literature 7 still has an oxygen barrier property insufficient for completely blocking oxygen and also is inferior to a container made of a polyolefin-based resin in the water vapor barrier property. In addition, since the polyester-based resin does not have oxygen-absorbing performance, the medical container has the problem of being impossible to prevent a degradation of the drug solution inside the container, if oxygen penetrates into the container from outside or if oxygen remains in the head space above the contents inside the container.

The prefilled syringe of Patent Literature 8 has an oxygen barrier property insufficient for completely blocking oxygen. In addition, the oxygen barrier resin composition of the intermediate layer does not have oxygen-absorbing performance. Thus, the prefilled syringe has the problem of being impossible to prevent degradation of the drug solution inside the container, if oxygen penetrates into the container from outside or if oxygen remains in the head space above the contents inside the container.

The resin composition of Patent Literature 9 has the problem of a reduction in strength due to oxidation degradation of the resin after oxidation absorption, resulting in a reduction in the strength of the packaging container itself. In addition, this resin composition also has the following problems: the oxygen-absorbing performance is still insufficient and the effect is expressed only when a moisture-rich articles are stored.

Furthermore, regarding a method for storing a biological medicine, the above-described known gas barrier multilayer container and the medical multilayer container are insufficient in the basic performance, such as oxygen barrier property, water vapor barrier property, adsorption of drug solution, and durability of the container. These containers, therefore, have some points to be improved in order to store biological medicines, and improvement is required from the viewpoint of storage performance of drug solutions.

In particular, when a biological medicine is stored in a conventional gas barrier multilayer container, complete removal of oxygen in a packaging container is actually difficult or significantly uneconomical even if any gas replacement is operated. In other words, it is difficult to completely eliminate oxygen, such as oxygen dissolved in a biological medicine, oxygen contained in air bubbles generated and introduced during mixing of the raw materials and other ingredients of a biological medicine, and oxygen dissolved in a solvent, such as distilled water, in a case of using the solvent. Although oxygen can be removed as much as possible by strictly controlling the conditions for selection and preparation of raw materials of a biological medicine and the conditions in production, such an operation ignoring an economic aspect is unrealistic. In addition, as described above, the oxygen barrier property of the gas barrier multilayer container is insufficient, and a small amount of oxygen penetrating from outside through the wall of the container cannot be completely eliminated.

For example, the medical container made of a polyester-based resin of Patent Literature 7 still has an oxygen barrier property insufficient for completely blocking oxygen and also is inferior to a container made of a polyolefin-based resin in the water vapor barrier property. In addition, since the polyester-based resin does not have oxygen-absorbing performance, the medical container has the problem of being impossible to prevent a degradation of the drug solution inside the container, if oxygen penetrates into the container from outside or if oxygen remains in the head space above the contents inside the container.

The prefilled syringe of Patent Literature 8 has an oxygen barrier property insufficient for completely blocking oxygen. In addition, the oxygen barrier resin composition of the intermediate layer does not have oxygen-absorbing performance. Thus, the prefilled syringe has the problem of being impossible to prevent degradation of the drug solution inside the container, if oxygen penetrates into the container from outside or if oxygen remains in the head space above the contents inside the container.

The resin composition of Patent Literature 9 has the problem of a reduction in strength due to oxidation degradation of the resin after oxygen absorption, resulting in a reduction in the strength of the packaging container itself. In addition, this resin composition also has the following problems: the oxygen-absorbing performance is still insufficient and the effect is expressed only when moisture-rich articles are stored.

The present invention has been made under the above-described circumstances, and an object thereof is to provide an oxygen-absorbing medical multilayer container having an excellent oxygen barrier property, maintaining the strength even in long-term storage, securing the visibility of the contents, and having a reduced amount of eluted impurities.

Another object of the present invention is to provide an oxygen-absorbing medical multilayer container having excellent oxygen barrier property and water vapor barrier property, maintaining the strength even in long-term storage, and having a reduced amount of eluted impurities.

Further another object of the present invention is to provide an oxygen-absorbing medical multilayer container having an excellent oxygen barrier property, maintaining the strength even in long-term storage, having a reduced amount of eluted impurities, and having excellent interlayer adhesion.

Further another object of the present invention is to provide an oxygen-absorbing prefilled syringe having an excellent oxygen barrier property, preferably also having excellent water vapor barrier performance, maintaining the strength even in long-term storage, and showing significantly suppressed generation of low-molecular-weight compounds after oxygen absorption.

Further another object of the present invention is to provide a method for storing a biological medicine while preventing oxidation degradation of the biological medicine during storage, protecting the biological medicine from a shock from outside for a long time, preventing contamination of the biological medicine with impurities, and preventing a reduction in drug efficacy of the biological medicine after storage.

Means for Solving the Problems

The present inventors have conducted intensive studies and have found that the above-described problems can be solved by an oxygen-absorbing medical multilayer container including at least three layers including a first resin layer containing a thermoplastic resin, an oxygen-absorbing layer containing a predetermined oxygen-absorbing composition, and a second resin layer containing a thermoplastic resin, in this order, and have accomplished the present invention.

That is, the present invention relates to the following aspects.

<1>

An oxygen-absorbing medical multilayer container comprising at least three layers comprising:

a first resin layer containing a thermoplastic resin (b1); an oxygen-absorbing layer containing an oxygen-absorbing composition; and a second resin layer containing a thermoplastic resin (b2), in this order, wherein the oxygen-absorbing composition comprises at least one compound having a tetralin ring represented by Formula (1), a transition metal catalyst, and a thermoplastic resin (a):

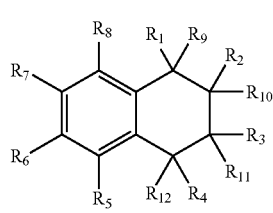

(1)

where $R_1$ to $R_{12}$ each independently represent a hydrogen atom or a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, an imide group, a substituent represented by Formula (1a), and a substituent represented by Formula (1b), which each optionally further have a substituent; two of the substituents represented by $R_1$ to $R_{12}$ are optionally bonded to each other to form a ring; and at least one hydrogen atom is bonded to a benzylic position of the tetralin ring;

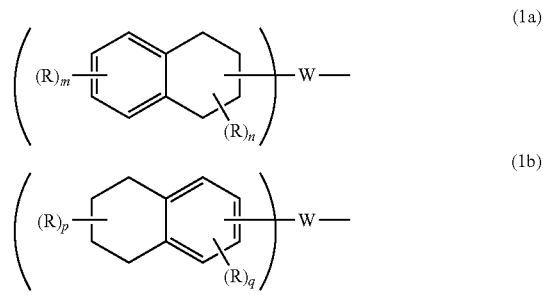

where R each independently represents a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, which each optionally further have a substituent; two of the substituents each represented by R are optionally bonded to each other to form a ring; W represents a bond or a bivalent organic group, the bivalent organic group being at least one selected from the group consisting of an aromatic hydrocarbon group, a saturated or unsaturated alicyclic hydrocarbon group, a linear or branched saturated or unsaturated aliphatic hydrocarbon group and a heterocyclic group, —C(=O)—, —OC(=O)—, —N(H)C(=O)—, and an arbitrary combination thereof; m represents an integer of 0 to 4; n represents an integer of 0 to 7; p represents an integer of 0 to 8; and q represents an integer of 0 to 3.

<2>

The oxygen-absorbing medical multilayer container according to <1>, wherein the compound having a tetralin ring represented by Formula (1) includes two or more carbonyl groups.

<3>

The oxygen-absorbing medical multilayer container according to <2>, wherein in Formula (1), at least two of $R_1$ to $R_{12}$ are monovalent substituents represented by Formula (2):

—C(=O)—X (2)

where X represents one selected from the group consisting of a hydrogen atom, a hydroxy group, an alkyl group, an alkoxy group, a monoalkylamino group, and a dialkylamino group; and a plurality of X may be the same or different.

<4>

The oxygen-absorbing medical multilayer container according to any one of <1> to <3>, wherein the compound having a tetralin ring represented by Formula (1) includes two or more tetralin rings.

<5>

The oxygen-absorbing medical multilayer container according to any one of <1> to <4>, wherein a proportion of the amount of the compound having a tetralin ring represented by Formula (1) to the total amount of the compound having a tetralin ring represented by Formula (1) and the thermoplastic resin (a) in the oxygen-absorbing composition is 1% to 30% by mass.

<6>

The oxygen-absorbing medical multilayer container according to any one of <1> to <5>, wherein the transition metal catalyst contains at least one transition metal selected from the group consisting of manganese, iron, cobalt, nickel, and copper.

<7>

The oxygen-absorbing medical multilayer container according to any one of <1> to <6>, wherein the transition metal catalyst is contained in an amount of 0.001 to 10 parts by mass in terms of the transition metal amount, in the oxygen-absorbing composition, based on 100 parts by mass of the total amount of the compound having a tetralin ring represented by Formula (1) and the thermoplastic resin (a).

<8>

The oxygen-absorbing medical multilayer container according to any one of <1> to <7>, wherein the thermoplastic resin (a) in the oxygen-absorbing composition is at least one selected from the group consisting of a polyolefin, a polyester, a polyamide, an ethylene-vinyl alcohol copolymer, a plant-derived resin, and a chlorine-containing resin.

<9>

The oxygen-absorbing medical multilayer container according to any one of <1> to <8>, wherein the thermoplastic resin (b1) is a polyolefin (PO1); and
the thermoplastic resin (b2) is a polyolefin (PO2).

<10>

The oxygen-absorbing medical multilayer container according to any one of <1> to <8>, wherein the thermoplastic resin (b1) is a polyester (PES1); and
the thermoplastic resin (b2) is a polyester (PES2).

<11>

The oxygen-absorbing medical multilayer container according to <10>, wherein at least one of the polyester (PES1) and the polyester (PES2) comprises dicarboxylic acid units, where 70 mol % or more of the dicarboxylic acid units are derived from one or more dicarboxylic acids selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid, and ester-forming derivatives thereof.

<12>

The oxygen-absorbing medical multilayer container according to any one of <1> to <8>, wherein the oxygen-absorbing medical multilayer container is an oxygen-absorbing prefilled syringe accommodating a drug in a sealed condition in advance and allowing the drug to be dispensed by releasing the sealed condition when the syringe is used.

<13>

A method for storing a biological medicine, comprising storing the biological medicine in the oxygen-absorbing medical multilayer container according to any one of <1> to <12>.

Advantageous Effects of Invention

The present invention can provide an oxygen-absorbing medical multilayer container having an excellent oxygen-absorbing performance and excellent oxygen barrier performance, maintaining the strength even in long-term storage, securing the visibility of the contents, and having a reduced amount of eluted impurities. In addition, a preferred aspect of the present invention can achieve an oxygen-absorbing medical multilayer container having an excellent water vapor barrier property and an oxygen-absorbing medical multilayer container not responsive to a metal detector.

In addition, the present invention can provide an oxygen-absorbing medical multilayer container having a good water vapor barrier property and excellent oxygen-absorbing performance having excellent oxygen barrier performance, maintaining the strength even in long-term storage, and having a reduced amount of eluted impurities. Furthermore, a preferred aspect of the present invention can achieve an oxygen-absorbing multilayer injection-molded product having excellent visibility to the inside of a container and not being responsive to a metal detector.

The present invention can provide an oxygen-absorbing medical multilayer container having excellent oxygen barrier performance having excellent oxygen-absorbing performance, maintaining the strength even in long-term storage, having a reduced amount of eluted impurities, and having excellent interlayer adhesion. In addition, a preferred aspect of the present invention can achieve an oxygen-absorbing multilayer injection-molded product having excellent visibility to the inside of a container and not being responsive to a metal detector.

The present invention can provide an oxygen-absorbing prefilled syringe having an excellent oxygen barrier property, preferably also having excellent water vapor barrier performance, maintaining the strength even in long-term storage, and showing significantly suppressed generation of low-molecular-weight compounds after oxygen absorption. In addition, a preferred aspect of the present invention can achieve an oxygen-absorbing prefilled syringe having excellent visibility to the inside of a container and not being responsive to a metal detector.

The present invention can provide a method for storing a biological medicine while preventing oxidation degradation of the biological medicine during storage, protecting the biological medicine from a shock from outside for a long time, preventing contamination of the biological medicine with impurities, and preventing a reduction in drug efficacy of the biological medicine after storage. In addition, a preferred aspect of the present invention can achieve a method for storing a biological medicine while allowing the biological medicine during storage to be seen from outside and not to be responsive to a metal detector.

DESCRIPTION OF EMBODIMENTS

Embodiments for implementing the present invention (hereinafter, simply referred to as "the embodiment") will now be described in detail. It should be noted that the following embodiments are merely examples for explaining the present invention and that the present invention is not limited to the following embodiments. The present invention can be implemented by being appropriately modified in a range not departing from the gist of the present invention.

First Embodiment

[Oxygen-Absorbing Medical Multilayer Container]

The oxygen-absorbing medical multilayer container of the embodiment includes at least three layers including a first resin layer (layer B) containing a thermoplastic resin (b), an oxygen-absorbing layer (layer A) containing an oxygen-absorbing composition, and a second resin layer (layer B) containing a thermoplastic resin (b) in this order, wherein the oxygen-absorbing composition includes at least one compound having a tetralin ring represented by Formula (1), a transition metal catalyst, and a thermoplastic resin (a):

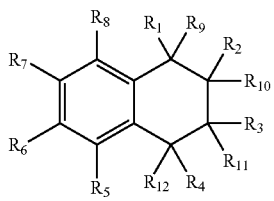
(1)

where $R_1$ to $R_{12}$ each independently represent a hydrogen atom or a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, an imide group, a substituent represented by Formula (1a), and a substituent represented by Formula (1b), which each optionally further have a substituent; two of the substituents represented by $R_1$ to $R_{12}$ are optionally bonded to each other to form a ring; and at least one hydrogen atom is bonded to a benzylic position of the tetralin ring.

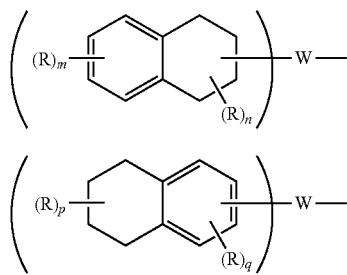

where R each independently represents a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, which each optionally further have a substituent; two of the substituents each represented by R are optionally bonded to each other to form a ring; W represents a bond or a bivalent organic group, the bivalent organic group being at least one selected from the group consisting of an aromatic hydrocarbon group, a saturated or unsaturated alicyclic hydrocarbon group, a linear or branched saturated or unsaturated aliphatic hydrocarbon group and a heterocyclic group, —C(=O)—, —OC(=O)—, —N(H)C(=O)—, and an arbitrary combination thereof; m represents an integer of 0 to 4; n represents an integer of 0 to 7; p represents an integer of 0 to 8; and q represents an integer of 0 to 3.

The oxygen-absorbing medical multilayer container of the embodiment can be used as, for example, a medical container for storing contents (article to be stored). In this case, the oxygen-absorbing medical multilayer container absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. This oxygen-absorbing medical multilayer container can absorb oxygen regardless of the presence or absence of water in the article to be stored and does not cause odor generation after oxygen absorption and can, therefore, be applied to a variety of medicinal products and medical supplies. In addition, the reduction in strength due to, for example, oxidation is significantly small even after oxygen absorption, and the strength of the oxygen-absorbing layer is maintained even in use for a long period of time. Consequently, an oxygen-absorbing medical multilayer container substantially not causing interlayer peeling can also be achieved. Accordingly, the oxygen-absorbing medical multilayer container of the embodiment is particularly useful for storage of medicinal products, biological medicines, medical supplies, and other articles that are required to be stored in a low concentration of oxygen.

The oxygen-absorbing medical multilayer container of the embodiment includes at least three layers including a first resin layer (layer B) at least containing a thermoplastic resin (b), an oxygen-absorbing layer (layer A) of an oxygen-absorbing composition, and a second resin layer (layer B) at least containing a thermoplastic resin (b) in this order.

The oxygen-absorbing medical multilayer container of the embodiment absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen.

The oxygen-absorbing medical multilayer container of the embodiment may have any layer structure in which the layers are arranged in an order of B/A/B, and the number and types of the oxygen-absorbing layer (layer A) and the resin layer (layer B) are not particularly limited. For example, the structure may be composed of one layer of layer A, two layers of layer B1 and two layers of layer B2 to form a five-layer structure of B1/B2/A/B2/B1, or may be composed of one layer of layer A and two-material two-layer of layer B1 and layer B2 to form a three-layer structure of B1/A/B2. The oxygen-absorbing medical multilayer container of the embodiment can optionally include an arbitrary layer, such as an adhesive layer (layer AD), to form, for example, a seven-layer structure of B1/AD/B2/A/B2/AD/B1.

[Oxygen-Absorbing Layer (Layer A)]

The oxygen-absorbing layer (layer A) in the oxygen-absorbing medical multilayer container of the embodiment is a layer containing an oxygen-absorbing composition that contains at least one compound having a tetralin ring represented by Formula (1) (hereinafter, also simply referred to as "tetralin compound"), a transition metal catalyst, and a thermoplastic resin (a).

<Compound Having a Tetralin Ring>

In Formula (1), examples of the monovalent substituent represented by $R_1$ to $R_{12}$ may include, but are not limited to, halogen atoms (e.g., chlorine, bromine, and iodine atoms), alkyl groups (preferably linear, branched, or cyclic alkyl groups having 1 to 15 carbon atoms, more preferably 1 to 6 carbon atoms, such as methyl, ethyl, n-propyl, isopropyl, tert-butyl, n-octyl, 2-ethylhexyl, cyclopropyl, and cyclopentyl groups), alkenyl groups (preferably linear, branched, or cyclic alkenyl groups having 2 to 10 carbon atoms, more preferably 2 to 6 carbon atoms, such as vinyl and allyl groups), alkynyl groups (preferably alkynyl groups having 2 to 10 carbon atoms, more preferably 2 to 6 carbon atoms, such as ethynyl and propargyl groups), aryl groups (preferably aryl groups having 6 to 16 carbon atoms, more preferably 6 to 10 carbon atoms, such as phenyl and naphthyl groups), heterocyclic groups (preferably monovalent groups each obtained by removing one hydrogen atom from a five- or six-membered aromatic or non-aromatic heterocyclic compound having 1 to 12 carbon atoms, more preferably 2 to 6 carbon atoms, such as 1-pyrazolyl, 1-imidazolyl, or 2-furyl group), a cyano group, a hydroxy group, a carboxyl group, ester groups, an amide group, a nitro group, alkoxy groups (preferably linear, branched, or cyclic alkoxy groups having 1 to 10 carbon atoms, more preferably 1 to 6 carbon atoms, such as methoxy and ethoxy groups), aryloxy groups (preferably aryloxy groups having 6 to 12 carbon atoms, more preferably 6 to 8 carbon atoms, such as a phenoxy group), acyl groups (including a formyl group, preferably alkylcarbonyl groups having 2 to 10 carbon atoms, more preferably 2 to 6 carbon atoms and preferably arylcarbonyl groups having 7 to 12 carbon atoms, more preferably 7 to 9 carbon atoms, such as acetyl, pivaloyl, and benzoyl groups), amino groups (preferably alkylamino groups having 1 to 10 carbon atoms, more preferably 1 to 6 carbon atoms; preferably anilino groups having 6 to 12 carbon atoms, more preferably 6 to 8 carbon atoms; and preferably heterocyclic amino groups having 1 to 12 carbon atoms, more preferably 2 to 6 carbon atoms, such as amino, methylamino, and anilino groups), a thiol group, alkylthio groups (preferably alkylthio groups having 1 to 10 carbon atoms, more preferably 1 to 6 carbon atoms, such as methylthio and ethylthio groups), arylthio groups (preferably arylthio groups having 6 to 12 carbon atoms, more preferably 6 to 8 carbon atoms, such as a phenylthio group), heterocyclic thio groups (preferably heterocyclic thio groups having 2 to 10 carbon atoms, more preferably 1 to 6 carbon atoms, such as a 2-benzothiazolylthio group), and imide groups (preferably imide groups having 2 to 10 carbon atoms, more preferably 4 to 8 carbon atoms, such as N-succinimide and N-phthalimide groups).

The compound represented by Formula (1) has at least one hydrogen atom bonded at a benzylic position of the tetralin ring. As described below, the hydrogen atom bonded to the benzylic position of the tetralin ring and a transition metal catalyst described below act such that, for example, excellent oxygen-absorbing performance is expressed. Examples of the compound having at least one hydrogen atom bonded at the benzylic position of a tetralin ring may include compounds having a hydrogen atom at any one of $R_1$, $R_4$, $R_9$, and $R_{12}$ in Formula (1)

When the monovalent substituents $R_1$ to $R_{12}$ have a hydrogen atom, the hydrogen atom may be further substituted with a substituent T (herein, substituent T is synonymous with those described as the monovalent substituents R). Examples of such substituents may include, but are not limited to, alkyl groups substituted with hydroxy groups (e.g., a hydroxyethyl group), alkyl groups substituted with alkoxy groups (e.g., a methoxyethyl group), alkyl groups substituted with aryl groups (e.g., a benzyl group), alkyl groups substituted with primary or secondary amino groups (e.g., an aminoethyl group), aryl groups substituted with alkyl groups (e.g., a p-tolyl group), and aryloxy groups substituted with alkyl groups (e.g., a 2-methylphenoxy group). When the monovalent substituent R has a monovalent substituent T, the number of carbon atoms of the substituent T is not included in the number of carbon atoms mentioned above. For example, a benzyl group is regarded as an alkyl group having one carbon atom substituted with a phenyl group and is not regarded as an alkyl group having seven carbon atoms substituted with a phenyl group. Furthermore, the monovalent substituent R may have a plurality of substituents T.

Two of the monovalent substituents represented by $R_1$ to $R_{12}$ may be bonded to each other to form a ring. Examples of such a compound may include compounds having five- to eight-membered rings formed by condensation of two of $R_1$ to $R_{12}$. The ring mentioned herein may have any known ring structure and is not particularly limited, but is preferably an aromatic or aliphatic, or hetero ring having 4 to 7 carbon atoms (more preferably a cyclohexane ring, a cycloheptane ring, an acid anhydride ring (e.g., succinic anhydride ring, glutaric anhydride ring, or adipic anhydride ring), a benzene ring, or a bicyclo ring).

From the viewpoint of suppressing the loss by volatilization during use and also increasing the amount of oxygen absorbed per unit mass of a compound, the compound having a tetralin ring represented by Formula (1) is preferably a compound in which at least one of $R_1$ to $R_{12}$ is selected from the group consisting of a substituted or unsubstituted alkyl group, a substituted or unsubstituted aryl group, a hydroxy group, a carboxyl group, a substituted or unsubstituted ester group, an alkoxy groups, an acyl group, a substituted or unsubstituted amide group, and a substituted or unsubstituted imide group (hereinafter, also simply referred to as "substituent group S") or a compound in which at least two of R are condensed to each other to form a five- or six-membered ring. Among the substituent group S, more preferred are substituted or unsubstituted alkyl groups, substituted or unsubstituted aryl groups, a hydroxy group, a carboxyl group, alkoxy groups, substituted or unsubstituted ester groups, and substituted or unsubstituted amide groups.

Examples of a preferred first aspect of the compound having a tetralin ring represented by Formula (1) may include those having the following structure:

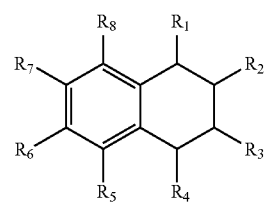

(1c)

where $R_1$ to $R_8$ each independently represent a monovalent substituent, the monovalent substituent being synonymous with $R_1$ to $R_{12}$ described above, provided that $R_1$ to $R_8$ do not form a ring by bonding of two or more thereof.

In the first aspect, at least two of $R_1$ to $R_8$ are each preferably one selected from the substituent group S, and the rest of $R_1$ to $R_8$ are each preferably a hydrogen atom. More preferably, two of $R_1$ to $R_8$ are each one selected from the substituent group S, and six of $R_1$ to $R_8$ are hydrogen atoms.

In the first aspect, there are a variety of isomers. For example, introduction of two substituents into the tetralin represented by Formula (1-1) has possibility of generating tetralin derivatives represented by Formulae (1-2) to (1-15), as structural isomers. The sites of introduction of substituents (sites of substitution) are not particularly limited.
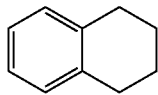
(1-1)
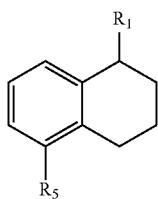
(1-2)
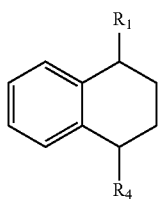
(1-3)
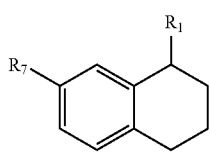
(1-4)
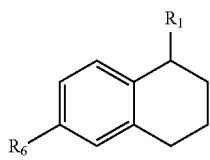
(1-5)
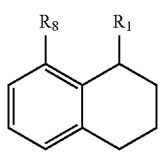
(1-6)
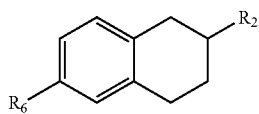
(1-7)
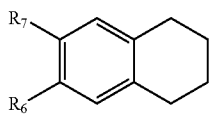
(1-8)
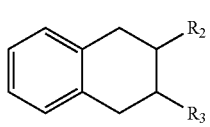
(1-9)
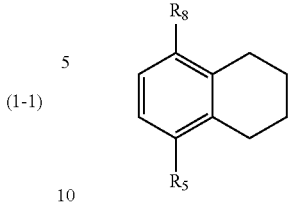
(1-10)
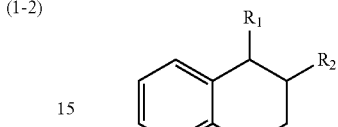
(1-11)
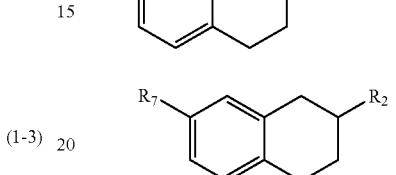
(1-12)
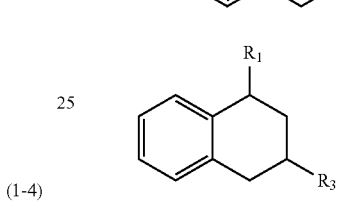
(1-13)
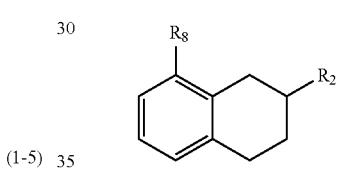
(1-14)
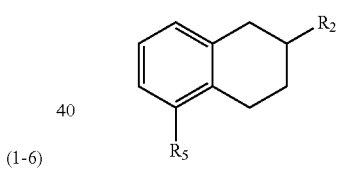
(1-15)
Non-limiting examples of the compounds included in the first aspect are shown in below.
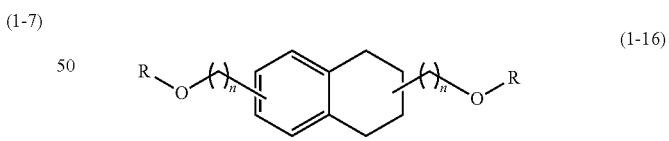
(1-16)
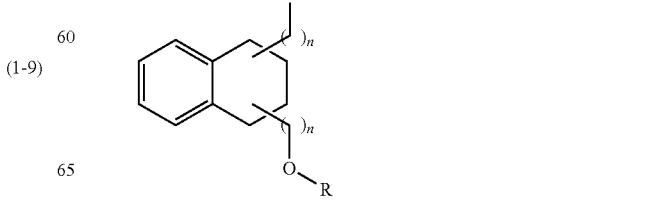
(1-17)

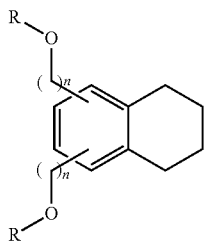
(1-18)

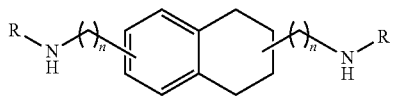
(1-19)

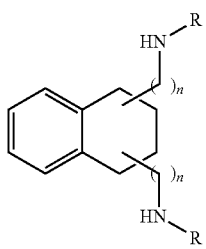
(1-20)

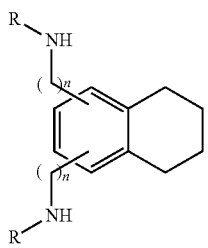
(1-21)

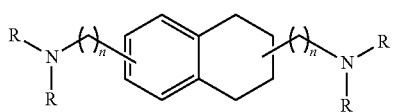
(1-22)

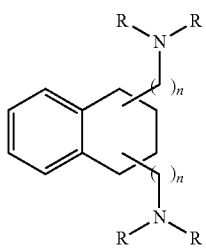
(1-23)

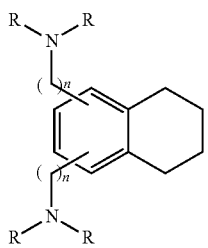
(1-24)

where n each independently represents an integer of 0 to 3; and R each independently represents a hydrogen atom or a monovalent substituent, the monovalent substituent being at least one selected from the group consisting of an aromatic hydrocarbon group, a saturated or unsaturated aliphatic hydrocarbon group, a linear or branched saturated or unsaturated aliphatic hydrocarbon group, and an acyl group.

Examples of the aromatic hydrocarbon group may include, but are not limited to, phenyl, tolyl, xylyl, naphthyl, anthracenyl, phenanthryl, biphenyl, and fluorenyl groups. Examples of the alicyclic hydrocarbon group may include, but are not limited to, cycloalkyl groups, such as cyclohexyl and cyclopentyl groups, and cycloalkenyl groups. Examples of the aliphatic hydrocarbon group may include, but are not limited to, linear or branched alkyl groups, such as methyl, ethyl, n-propyl, isopropyl, n-butyl, isobutyl, sec-butyl, tert-butyl, n-hexyl, n-octyl, 2-ethylhexyl, n-decyl, lauryl, stearyl, and palmityl groups; and alkenyl groups, such as ethenyl, propenyl, butenyl, octenyl, nonadenyl, and pentacosenyl groups. Examples of the acyl group may include, but are not limited to, acetyl, pivaloyl, and benzoyl groups. These substituents may further have substituents. Examples of such substituents may include halogen atoms, alkoxy groups, a hydroxy group, a carboxyl group, carboalkoxy groups, amino groups, acyl groups, thio groups (e.g., alkylthio, phenylthio, tolylthio, and pyridylthio groups), amino groups (e.g., unsubstituted amino, methylamino, dimethylamino, and phenylamino groups), a cyano group, and a nitro group.

Examples of a preferred second aspect of the compound having a tetralin ring represented by Formula (1) may include those having the following structures represented by Formulae (2-1) to (2-5):

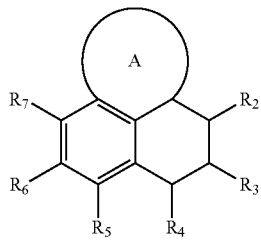
(2-1)

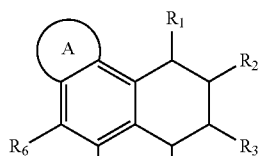
(2-2)

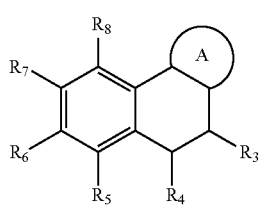
(2-3)

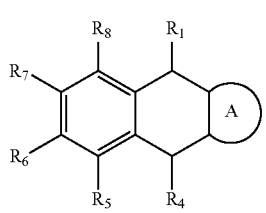
(2-4)

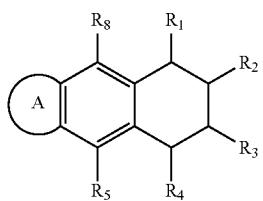

(2-5)

where $R_1$ to $R_8$ each independently represent a hydrogen atom or a monovalent substituent, the monovalent substituents $R_1$ to $R_8$ being synonymous with $R_1$ to $R_{12}$ described in Formula (1); and arc A represents a substituted or unsubstituted aromatic, heterocyclic, or acid anhydride ring having 4 to 7 carbon atoms.

In the second aspect, arc A is preferably an aromatic, aliphatic, or hetero ring having 4 to 7 carbon atoms. Examples of such a ring may include a benzene ring, a cyclopentane ring, a cyclohexane ring, a cycloheptane ring, and acid anhydride rings (succinic anhydride ring, glutaric anhydride ring, and adipic anhydride ring).

Examples of a preferred third aspect of the compound having a tetralin ring represented by Formula (1) may include those having two or more carbonyl groups.

In examples of the third aspect of the compound having two or more carbonyl groups, two or more of $R_1$ to $R_{12}$ in Formula (1) are preferably monovalent substituents represented by Formula (2):

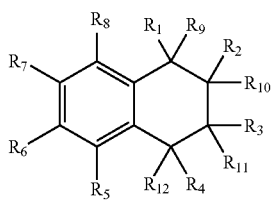

(1)

where $R_1$ to $R_{12}$ each independently represent a hydrogen atom or a monovalent substituent, the monovalent substituents $R_1$ to $R_{12}$ being synonymous with those described above, provided that $R_1$ to $R_{12}$ do not form a ring by bonding of two or more thereof.

—C(=O)X    (2)

where X represents one selected from the group consisting of a hydrogen atom, a hydroxy group, an alkyl group, an alkoxy group, a monoalkylamino group, and a dialkylamino group, and a plurality of X may be the same or different.

In the third aspect, $R_1$ to $R_{12}$ more preferably satisfy any of the following requirements (A) to (C):

(A) One or more monovalent substituents represented by Formula (2) are bonded to the aromatic ring of the tetralin ring, and one or more monovalent substituents represented by Formula (2) are bonded to the aliphatic ring of the tetralin ring;

(B) Two or more monovalent substituents represented by Formula (2) are bonded to the aromatic ring of the tetralin ring; and (C) Two or more monovalent substituents represented by Formula (2) are bonded to the aliphatic ring of the tetralin ring.

In the monovalent substituent represented by Formula (2), X is preferably an alkoxy group represented by an —O—Z group or a monoalkylamino group represented by an NH—Z group, where —Z more preferably represents an aromatic hydrocarbon, saturated or unsaturated aliphatic hydrocarbon, or linear or branched saturated or unsaturated aliphatic hydrocarbon group having 1 to 10 carbon atoms. Since specific examples of these substituents are the same as those described in substituent R, the description thereof is omitted here.

Non-limiting examples of the third aspect satisfying any of the requirements (A) to (C) are shown below:

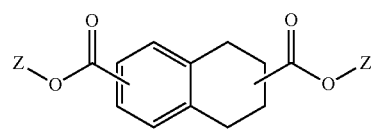

(3-1)

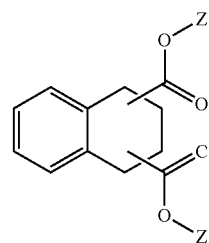

(3-2)

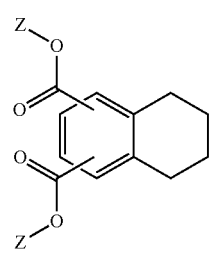

(3-3)

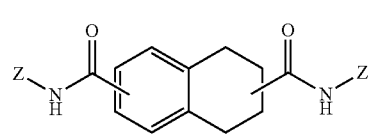

(3-4)

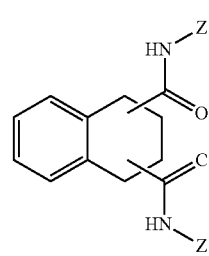

(3-5)

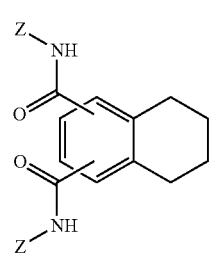

(3-6)

where each Z is synonymous with that described in Formula (2).

Among the above-mentioned examples of the third aspect, more preferred are compounds represented by Formulae (3-10) to (3-20):

(3-20)
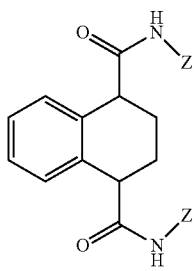
Non-limiting examples of the compound having a tetralin ring represented by Formula (1) are shown below:
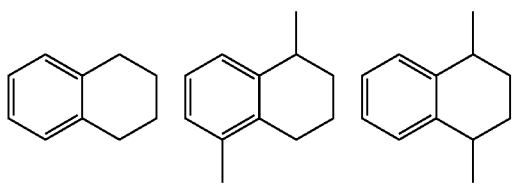
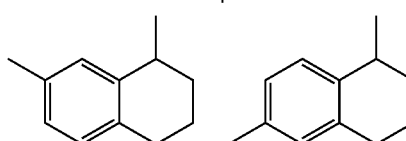
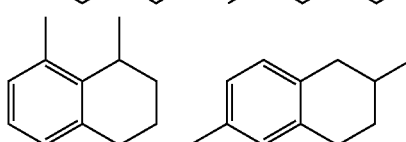
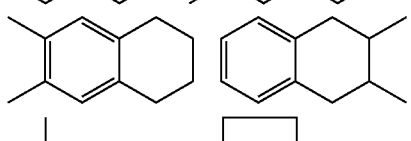
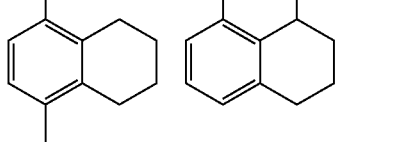
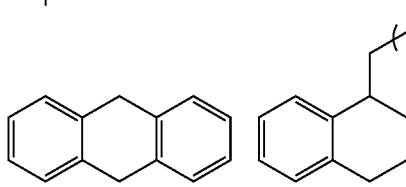
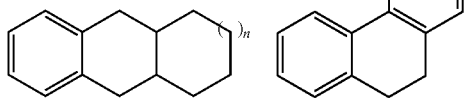
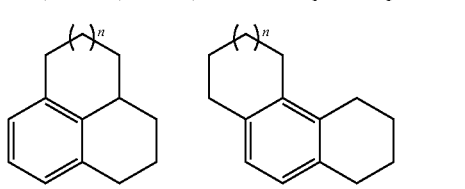
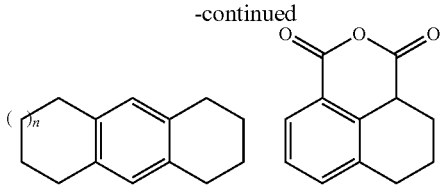
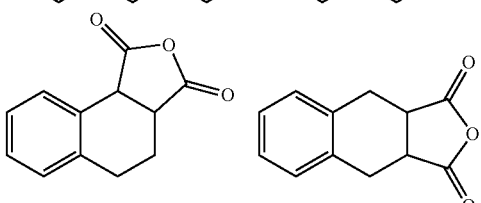
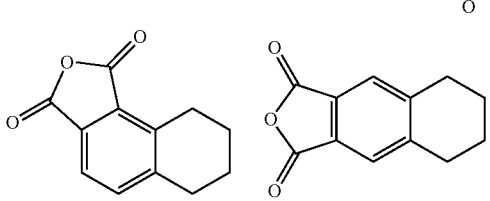
where each n represents an integer of 0 to 3,
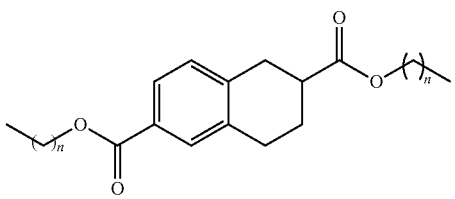
where n each independently represents an integer of 0 to 7,

25
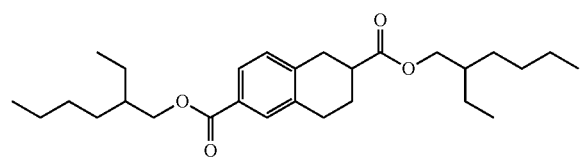
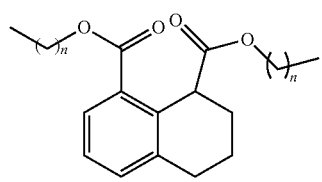
where n each independently represents an integer of 0 to 7,
26
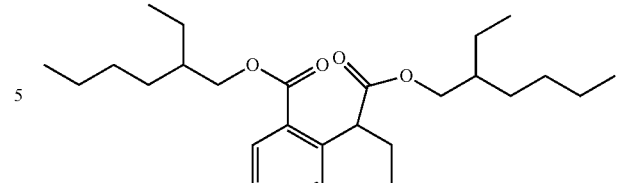
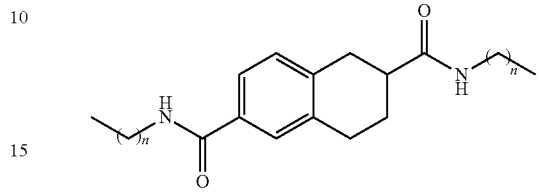
where n each independently represents an integer of 0 to 7,
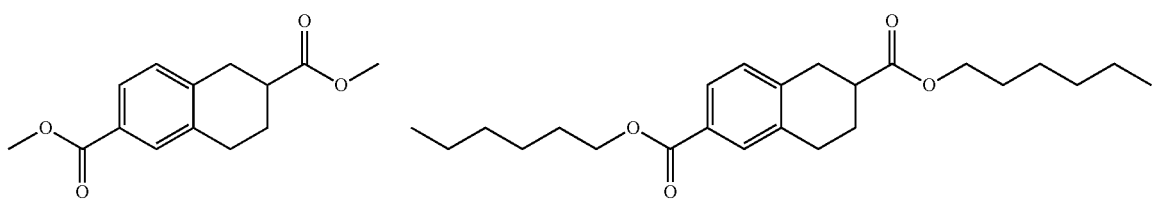
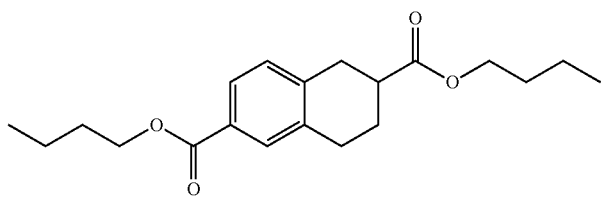
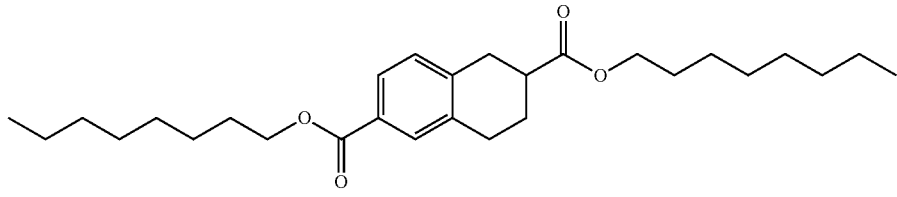
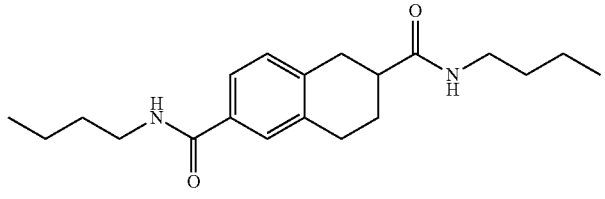
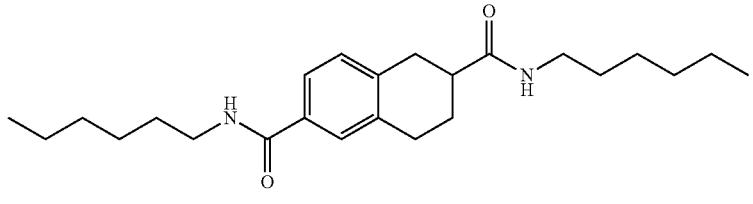
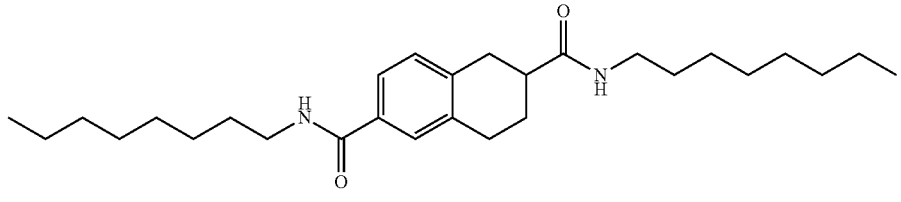

Examples of a preferred fourth aspect of the compound having a tetralin ring represented by Formula (1) may include those having two or more tetralin rings. The upper limit of the number of the tetralin rings is preferably 12, and the number of the tetralin rings is preferably 3 or less, from the viewpoint of easiness of acquisition. In particular, from the viewpoint of balance among oxygen-absorbing performance, the effect of heat resistance, and easiness of acquisition, the number of tetralin rings is more preferably 2.

Examples of the compound having two or more tetralin rings in the fourth aspect are preferably compounds represented by formulae selected from the group consisting of Formulae (4-1) to (4-6):

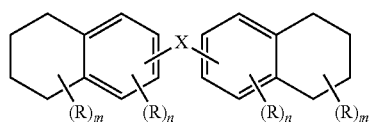

(4-1)

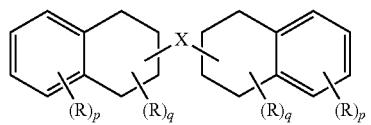

(4-2)

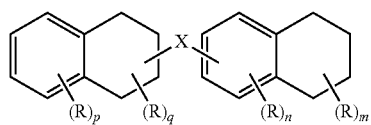

(4-3)

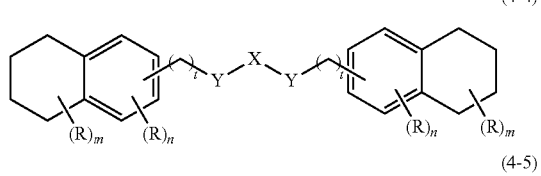

(4-4)

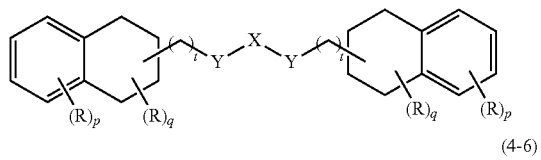

(4-5)

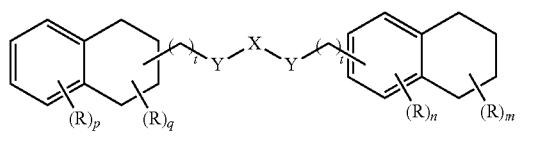

(4-6)

where R each independently represents a monovalent substituent, the monovalent substituent R being synonymous with $R_1$ to $R_{12}$ described above; m each independently represents an integer of 0 to 7; n each independently represents an integer of 0 to 3; p each independently represents an integer of 0 to 4; q each independently represents an integer of 0 to 6; one or more hydrogen atoms are bonded to a benzylic position of the tetralin ring; each X represents a bivalent group containing at least one group selected from the group consisting of an aromatic hydrocarbon group, a saturated or unsaturated alicyclic hydrocarbon group, a linear or branched saturated or unsaturated aliphatic hydrocarbon group, and a heterocyclic group; Y each independently represents an ester group or an amide group; and t each independently represents an integer of 0 to 6.

Examples of the substituent represented by R in Formulae (4-1) to (4-6) may include those exemplified as $R_1$ to $R_{12}$. Among them, preferred are a hydrogen atom, substituted or unsubstituted alkyl group, substituted or unsubstituted aryl groups, a hydroxy group, a carboxyl group, ester groups, alkoxy groups, acyl groups, amide groups, and imide groups; more preferred are a hydrogen atom, substituted or unsubstituted alkyl groups, substituted or unsubstituted aryl groups, alkoxy groups, ester groups, and acyl groups; and most preferred are a hydrogen atom, unsubstituted alkyl groups, alkoxy groups, and ester groups.

The compound represented by any of Formulae (4-1) to (4-6) preferably has a molecular weight of 276 to 1000, more preferably 300 to 800, and most preferably 350 to 600. A compound having a molecular weight of 276 or more can suppress the loss by volatilization during use, compared to a compound having a molecular weight less than 276. A compound having a molecular weight of 1000 or less increases the proportion of the tetralin ring portion in the compound and increases the amount of oxygen absorbed per unit mass of the compound, compared to a compound having a molecular weight higher than 1000.

The compound represented by any of Formulae (4-1) to (4-6) preferably has a high boiling point and a low vapor pressure at the temperature during use, from the viewpoint of suppressing the loss by volatilization during use. When the compound is used in an oxygen-absorbing composition described below, a lower vapor pressure at the temperature for kneading with a thermoplastic resin and a higher 3% weight-reduction temperature are preferred for suppressing the loss by volatilization during production of the oxygen-absorbing composition. The 3% weight-reduction temperature is preferably 150° C. or more, more preferably 200° C. or more, and most preferably 250° C. or more.

Among the functional groups mentioned above, one having a hydrogen atom may be further substituted with any of the above-mentioned substituents. Examples of such a functional group may include, but are not limited to, alkyl groups substituted with hydroxy groups (e.g., a hydroxyethyl group), alkyl groups substituted with alkoxy groups (e.g., a methoxyethyl group), alkyl groups substituted with aryl groups (e.g., a benzyl group), aryl groups substituted with alkyl groups (e.g., a p-tolyl group), and aryloxy groups substituted with alkyl groups (e.g., a 2-methylphenoxy group). When a functional group is further substituted with a substituent, the number of carbon atoms of the substituent is not included in the number of carbon atoms mentioned above. For example, a benzyl group is regarded as an alkyl group having one carbon atom substituted with a phenyl group and is not regarded as an alkyl group having 7 carbon atoms substituted with a phenyl group. Furthermore, the substituent of the tetralin may have a plurality of substituents. These are not necessarily a single substance and may be a mixture of two or more thereof.

The compounds represented by Formulae (4-1) to (4-6) are more preferably the compounds represented by Formulae (4-7) to (4-16) and most preferably the compounds represented by Formula (4-7), (4-10), (4-13), or (4-16).

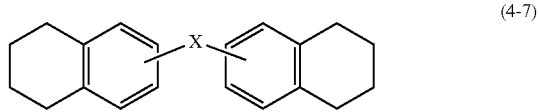

(4-7)

-continued (4-8)
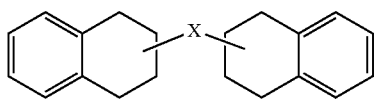

(4-9)
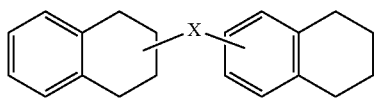

(4-10)
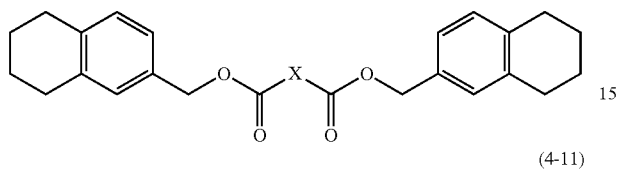

(4-11)
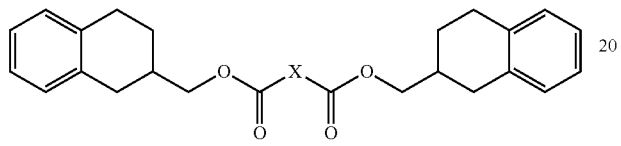

(4-12)
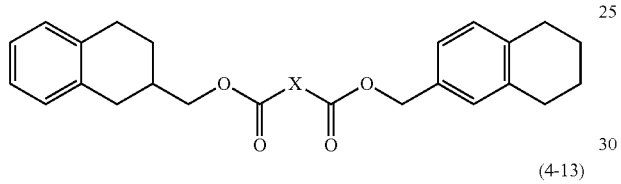

(4-13)
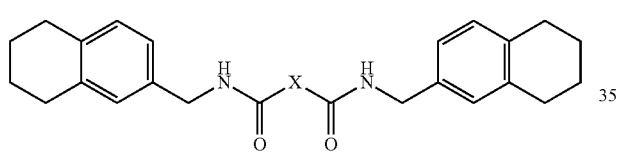

(4-14)
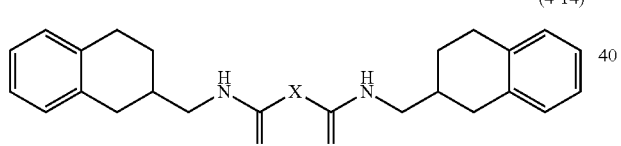

(4-15)
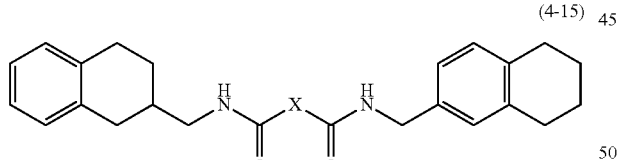

(4-16)
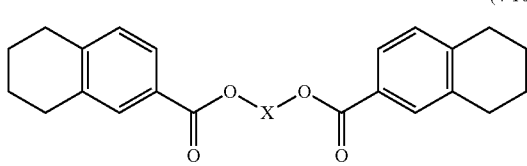

where each X represents an aromatic hydrocarbon group, a saturated or unsaturated alicyclic hydrocarbon group, a linear or branched saturated or unsaturated aliphatic hydrocarbon group.

Preferred examples of the compound represented by Formula (4-7) are shown below, but the embodiment is not limited thereto.

(4-17)
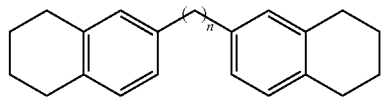

where n represents an integer of 1 to 10;

(4-18)
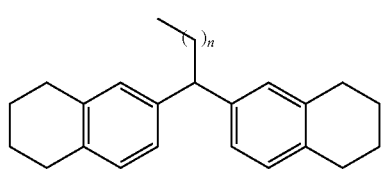

where n represents an integer of 1 to 8; and (4-19)
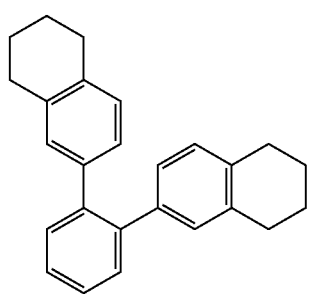

(4-20)
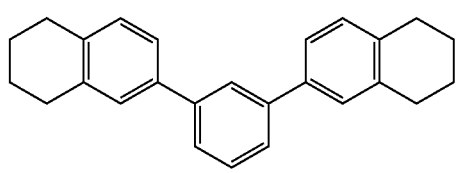

(4-21)
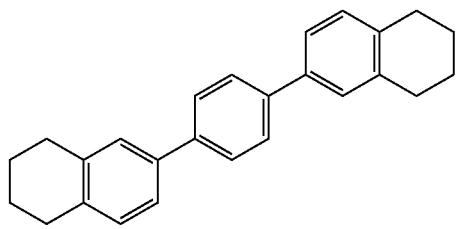

Preferred examples of the compound represented by Formula (4-10) are shown below, but the embodiment is not limited thereto.

(4-22)
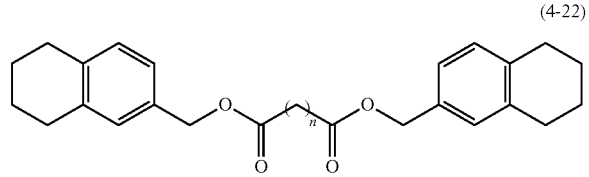

where n represents an integer of 1 to 8; and
(4-23)
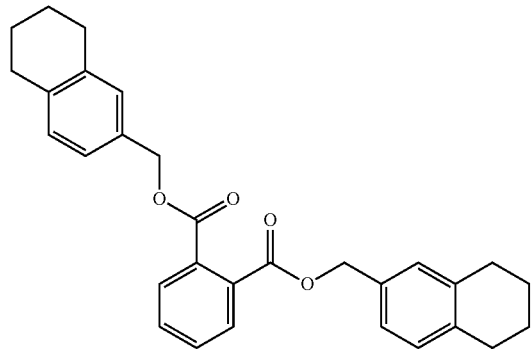
(4-24)
(4-25)
Preferred examples of the compound represented by Formula (4-13) are shown below, but the embodiment is not limited thereto.
(4-26)
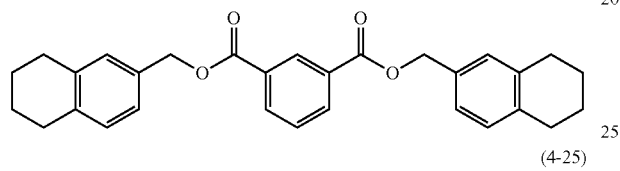
where n represents an integer of 1 to 8; and
(4-27)
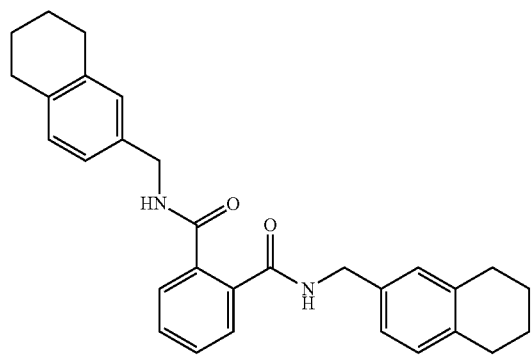
(4-28)
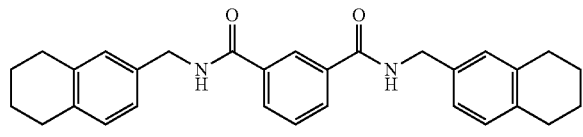
(4-29)
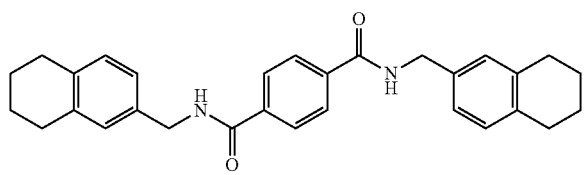
Preferred examples of the compound represented by Formula (4-16) are shown below, but the embodiment is not limited thereto.
(4-30)
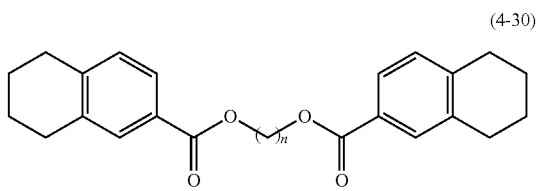
where n represents an integer of 1 to 10; and
(4-31)
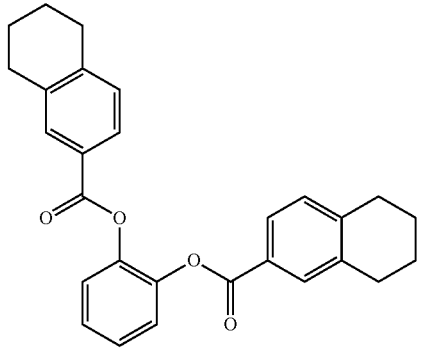
(4-32)
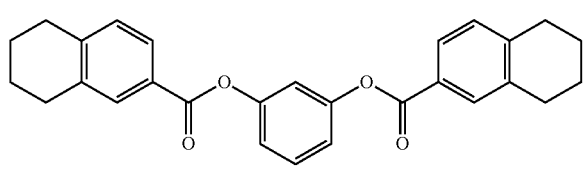
(4-33)
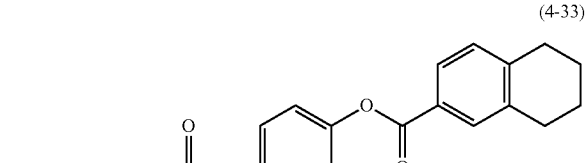

The compounds represented by Formulae (4-1) to (4-16) and (4-17) to (4-33) are examples of the compound having two tetralin rings in one molecule. In the embodiment, compounds having three or more tetralin rings in one molecule can also be preferably used.

The compounds represented by Formulae (4-1) to (4-6) may be produced by any method and can be produced by a known method. For example, such a compound can be preferably produced through transesterification between an ester of a polycarboxylic acid having two or more carboxyl groups and a compound having a hydroxy group and a tetralin ring, a reaction between a polyol having two or more hydroxy groups and a compound having a carboxyl group and a tetralin ring, and a reaction between an aldehyde and a compound having a tetralin ring.

Other preferred examples of the compound having two or more tetralin rings in the fourth aspect may include compounds having two or more tetralin rings at least one of which has a benzylic position to which a hydrogen atom is bonded and has two or more imide bonds.

Such a compound can have a larger number of reactive sites with oxygen due to the existence of the two or more tetralin rings and can further improve the heat resistance due to the existence of the two or more imide bonds. Such a compound is preferably at least one compound represented by a formula selected from, for example, the group consisting of Formulae (4-34) to (4-37):

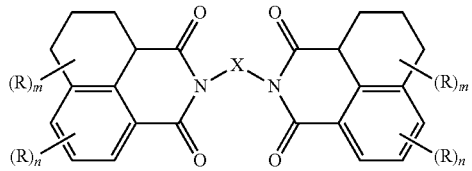
(4-34)

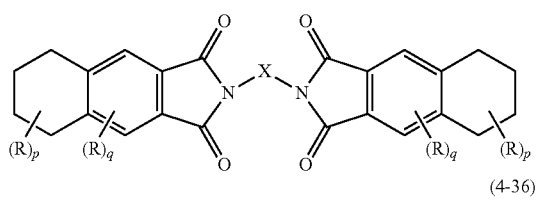
(4-35)

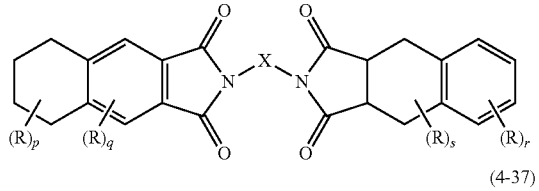
(4-36)

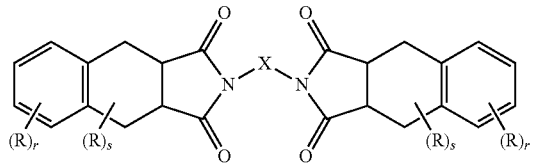
(4-37)

where R each independently represents a monovalent substituent, the monovalent substituent R being synonymous with $R_1$ to $R_{12}$ described above; m each independently represents an integer of 0 to 6; n each independently represents an integer of 0 to 3, p each independently represents an integer of 0 to 7, q each independently represents an integer of 0 to 2, R each independently represents an integer of 0 to 4, and s each independently represents an integer of 0 to 5; one or more hydrogen atoms are bonded to the benzylic position of at least one tetralin ring; and each X represents a bivalent substituent, the bivalent substituent being at least one selected from the group consisting of an aromatic hydrocarbon group, a saturated or unsaturated alicyclic hydrocarbon group, a linear or branched saturated or unsaturated aliphatic hydrocarbon group, and a heterocyclic group.

The compound represented by any of Formulae (4-34) to (4-37) may have any molecular weight, and the molecular weight is preferably 414 to 1000, more preferably 430 to 800, and most preferably 450 to 600. A molecular weight of 414 or more can further suppress the loss by volatilization during use. A molecular weight of 1000 or less can further improve the oxygen absorbing performance.

The compound represented by any of Formulae (4-34) to (4-37) preferably has a high boiling point and a low vapor pressure at the temperature during use, from the viewpoint of further suppressing the loss by volatilization during use. Such a compound also preferably has a lower vapor pressure at the temperature for kneading with a thermoplastic resin and also preferably has a higher 3% weight-reduction temperature. The 3% weight-reduction temperature is not specifically limited and is preferably 150° C. or more, more preferably 200° C. or more, further preferably 250° C. or more, and most preferably 270° C. or more.

The compounds represented by Formulae (4-34) to (4-37) may be produced by any method and can be produced by a known method, such as a reaction between a diamine compound and an acid anhydride compound.

The compound having a tetralin ring represented by Formula (1) has a hydrogen atom at a benzylic position of the tetralin ring and expresses excellent oxygen-absorbing performance by removing the hydrogen atom at the benzylic position through the use together with a transition metal catalyst described below.

The oxygen-absorbing composition can prevent an increase in odor strength after oxygen absorption. Although the reason thereof is not elucidated, for example, the following oxidation reaction mechanism is presumed. That is, it is presumed that a compound having a tetralin ring represented by Formula (1) is turned into a radical by removing a hydrogen atom at a benzylic position of the tetralin ring and that the carbon atom at the benzylic position is oxidized by the reaction between the radical and an oxygen atom to generate a hydroxy group or a ketone group. Consequently, in the oxygen-absorbing composition, the molecular chain of the oxygen-absorbing base compound is not cleaved by an oxidation reaction, unlike existing technologies, and the structure of the oxygen-absorbing base compound is maintained. An organic compound having a low molecular weight causing an odor is, therefore, scarcely generated after oxygen absorption, and as a result, an increase in odor strength after oxygen absorption is presumed to be inhibited. From also these viewpoints, a compound having a larger number of tetralin rings is preferred. Such a compound has an increased number of reactive sites with oxygen and has further excellent oxygen-absorbing performance. Although at least one tetralin ring may have the benzylic position to which a hydrogen atom is bonded, for example, when a compound has a substituent represented by Formula (1a) or Formula (1b), the tetralin ring of the substituent represented by Formula (1a) or Formula (1b) also preferably has the benzylic position to which a hydrogen atom bonded, from the viewpoint described above.

The molecular weight of the compound having a tetralin ring represented by Formula (1) can be appropriately adjusted depending on the desired characteristics or the substituents $R_1$ to $R_{12}$ to be introduced and is not specifically limited. From the viewpoint of suppressing the loss by volatilization during use and also increasing the amount of oxygen absorbed per unit mass of the compound, the molecular weight is preferably 190 to 1500, more preferably 210 to 1200, and most preferably 250 to 1000. The above-described compounds having tetralin rings represented by Formula (1) may be used alone or in combination of two or more thereof.

Among compounds having tetralin rings represented by Formula (1), preferred is a compound having a high boiling point, i.e., having a low vapor pressure at the temperature during use, from the viewpoint of suppressing the loss by volatilization during use. For example, a compound having a lower vapor pressure at the temperature for kneading with a thermoplastic resin (a) can suppress the loss by volatilization during production of the oxygen-absorbing composition and is therefore preferred. An index of the loss by volatilization can be, for example, the 3% weight-reduction temperature. That is, the compound preferably has a 3% weight-reduction temperature of 100° C. or more, more preferably 150° C. or more, and most preferably 200° C. or more. The upper limit of the 3% weight-reduction temperature is not specifically limited.

In the oxygen-absorbing composition, the proportion of the compound having a tetralin ring represented by Formula (1) based on the total amount of the compound having a tetralin ring represented by Formula (1) and the thermoplastic resin (a) described below is preferably 1% to 30% by mass, more preferably 1.5% to 25% by mass, and most preferably 2% to 20% by mass. A proportion of the compound having a tetralin ring represented by Formula (1) not lower than the above-mentioned lower limit can further enhance the oxygen-absorbing performance, and a proportion not higher than the above-mentioned upper limit can further enhance the moldability.

<Transition Metal Catalyst>

The transition metal catalyst contained in the oxygen-absorbing composition can be appropriately selected from known catalysts that can function as a catalyst for the oxidation reaction of the compound having a tetralin ring and is not specifically limited.

Examples of such a transition metal catalyst may include organic acid salts, halides, phosphates, phosphites, hypophosphites, nitrates, sulfates, oxides, and hydroxides of transition metals. Examples of the transition metal contained in the transition metal catalyst may include, but are not limited to, titanium, vanadium, chromium, manganese, iron, cobalt, nickel, copper, zinc, ruthenium, and rhodium. Among these metals, preferred are manganese, iron, cobalt, nickel, and copper. Examples of the organic acid may include, but are not limited to, acetic acid, propionic acid, octanoic acid, lauric acid, stearic acid, acetylacetone, dimethyldithiocarbamic acid, palmitic acid, 2-ethylhexanoic acid, neodecanoic acid, linoleic acid, tall acid, oleic acid, capric acid, and naphthenic acid. The transition metal catalyst is preferably a combination of such a transition metal and an organic acid, where the transition metal is more preferably manganese, iron, cobalt, nickel, or copper; and the organic acid is more preferably acetic acid, stearic acid, 2-ethylhexanoic acid, oleic acid, or naphthenic acid. The transition metal catalysts may be used alone or in combination of two or more thereof.

The amount of the transition metal catalyst blended can be appropriately determined depending on the types of the compound having a tetralin ring, the transition metal catalyst, and the thermoplastic resin (a) used and the desired performance and is not specifically limited. From the viewpoint of the amount of oxygen absorbed by the oxygen-absorbing composition, the amount of the transition metal catalyst blended is preferably 0.001 to 10 parts by mass, more preferably 0.005 to 2 parts by mass, and most preferably 0.01 to 1 parts by mass, as the amount of the transition metal, based on 100 parts by mass of the total amount of the compound having a tetralin ring represented by Formula (1) and the thermoplastic resin (a).

In addition, for example, a mixture of the compound and the transition metal catalyst may be molded into a powdery, granular, pellet-like, or other small-piece form by a known granulation or molding method and may be blended with the thermoplastic resin (a) to form layer A.

The oxygen-absorbing composition used in the embodiment may optionally further contain a support material. On this occasion, the oxygen-absorbing composition containing a support material can be prepared as a mixture of the above-described compound, a thermoplastic resin (a), a transition metal catalyst, and a support material and can be directly used as an oxygen absorber. Alternatively, the above-described compound having a tetralin ring represented by Formula (1) is supported on or impregnated in the support material, if necessary, together with the transition metal catalyst to give a supporting body composed of the support material and the compound supported on or impregnated in the support material (hereinafter, also referred to as "oxygen absorber-supporting body"). This supporting body can also be used as an oxygen absorber. Thus, the supporting or impregnation of the compound to the support material increases the contact area with oxygen and can thereby increase the oxygen absorption rate or the amount of oxygen absorbed and can simplify the handling.

The support material can be appropriately selected from those known in the art, and examples thereof may include, but are not limited to, powders of synthetic calcium silicate, calcium hydroxide, activated carbon, zeolite, perlite, diatomaceous earth, activated clay, silica, kaolin, talc, bentonite, activated alumina, gypsum, silica alumina, calcium silicate, magnesium oxide, graphite, carbon black, aluminum hydroxide, and iron oxide. Among these support materials, preferred are synthetic calcium silicate, diatomaceous earth, silica, and activated carbon. The support materials may be used alone or in combination of two or more thereof.

The amount of the support material blended can be appropriately determined depending on the types of the compound, the thermoplastic resin (a), and the transition metal catalyst used and the desired performance and is not specifically limited. The amount of the support material blended is preferably 10 to 1000 parts by mass, more preferably 20 to 800 parts by mass, based on 100 parts by mass of the compound having a tetralin ring represented by Formula (1).

The compound can be supported on the support material by a common method, and the method is not specifically limited. For example, a mixture containing the above-described compound having a tetralin ring represented by Formula (1) or a mixture containing the compound and a transition metal catalyst is prepared, and, for example, this mixture is applied to a support material, or a support material is immersed in this mixture. Thus, an oxygen absorber supporting body in which the compound (and optionally a transition metal catalyst) is supported on (impregnated in) the support material can be obtained. In the preparation of the mixture, a solvent may be further added to the mixture. When the compound and the transition metal catalyst are solids, the use of a solvent allows these solids to be efficiently supported on a support material. The solvent used here can be appropriately selected from known solvents with consideration of, for example, solubility of the compound and the transition metal catalyst and is not specifically limited. The solvent is preferably an organic solvent, such as methanol, 2-propanol, ethylene glycol, toluene, xylene, methyl acetate, ethyl acetate, butyl acetate, diisopropyl ether, tetrahydrofuran, methyl ethyl ketone, dichloromethane, or chloroform, and more preferably methanol, 2-propanol, ethyl acetate, or methyl ethyl ketone. These solvents may be used alone or in combination of two or more thereof.

<Thermoplastic Resin (a)>

The oxygen-absorbing composition contains a thermoplastic resin (a). On this occasion, the compound and the transition metal catalyst may be contained in the oxygen-absorbing composition in any forms. For example, the compound and the transition metal catalyst may be directly contained in the thermoplastic resin (a), or the compound and the transition metal catalyst supported on the above-described support material may be contained in the thermoplastic resin (a).

The oxygen-absorbing composition can be prepared by a common method, and the method is not specifically limited. For example, an oxygen-absorbing composition can be prepared by mixing or kneading the compound, a transition metal catalyst, and an optional support material with a thermoplastic resin (a).

As the thermoplastic resin (a), any known one can be appropriately used. Examples thereof may include, but are not limited to, low-density polyethylenes, medium-density polyethylenes, high-density polyethylenes, linear low-density polyethylenes, linear extremely low-density polyethylenes, polypropylene, poly-1-butene, and poly-4-methyl-1-pentene; polyolefins being random or block copolymers of α-olefins such as ethylene, propylene, 1-butene, and 4-methyl-1-pentene; acid modified polyolefins, such as maleic anhydride grafted polyethylene and maleic anhydride grafted polypropylene; ethylene-vinyl compound copolymers, such as ethylene-vinyl acetate copolymers, ethylene-vinyl alcohol copolymers, ethylene-vinyl chloride copolymers, ethylene-(meth)acrylic acid copolymers and ion crosslinked compounds thereof (ionomers), and ethylene-methyl methacrylate copolymers; styrene-based resins such as polystyrene, acrylonitrile-styrene copolymers, and α-methylstyrene-styrene copolymers; polyvinyl compounds, such as poly(methyl acrylate) and poly(methyl methacrylate); polyamides, such as nylon 6, nylon 66, nylon 610, nylon 12, and poly(metaxylylene adipamide) (MXD6); polyesters, such as poly(ethylene terephthalate) (PET), poly(butylene terephthalate) (PBT), poly(trimethylene terephthalate) (PTT), poly(ethylene naphthalate) (PEN), glycol-modified poly(ethylene terephthalate) (PETG), poly(ethylene succinate) (PES), poly(butylene succinate) (PBS), poly(lactic acid), poly(glycolic acid), polycaprolactone, and poly(hydroxy alkanoate); polycarbonate; polyethers such as polyethylene oxide; and mixtures thereof. These thermoplastic resins may be used alone or in combination of two or more thereof.

Among these thermoplastic resins, the thermoplastic resin (a) is more preferably at least one selected from the group consisting of a polyolefin, a polyester, a polyamide, an ethylene-vinyl alcohol copolymer, a plant-derived resin, and a chlorine-containing resin, more preferably at least one selected from the group consisting of a polyolefin, a polyester, a polyamide, an ethylene-vinyl alcohol copolymer, and a chlorine-containing resin. These preferred thermoplastic resins will now be described in detail.

<Polyolefin>

Examples of the polyolefin contained in the oxygen-absorbing composition may include polyethylenes, such as low-density polyethylene, medium-density polyethylenes, high-density polyethylenes, linear low-density polyethylenes, and linear extremely low-density polyethylenes; olefin homopolymers, such as polypropylene, polybutene-1, and poly-4-methylpentene-1; copolymers of ethylene and α-olefin, such as ethylene-propylene random copolymers, ethylene-propylene block copolymers, ethylene-propylene-polybutene-1 copolymers, and ethylene-cyclic olefin copolymers; ethylene-α,β-unsaturated carboxylic acid copolymers, such as ethylene-(meth)acrylic acid copolymers; ethylene-α,β-unsaturated carboxylic acid ester copolymers, such as ethylene-ethyl (meth)acrylate copolymers; other ethylene copolymers, such as ion crosslinked compounds of ethylene-α,β-unsaturated carboxylic acid copolymers and ethylene-vinyl acetate copolymers; and ring-opened polymers of cyclic olefins and hydrogen-added products thereof, cyclic olefin-ethylene copolymers, and graft-modified polyolefins prepared by graft modification of these polyolefins with acid anhydrides such as maleic anhydride.

<Polyester>

The polyester contained in the oxygen-absorbing composition is, for example, composed of one or two or more selected from polyvalent carboxylic acids including dicarboxylic acids and their ester-forming derivatives and one or two or more selected from polyhydric alcohols including glycols; composed of a hydroxycarboxylic acid and its ester-forming derivative; or composed of a cyclic ester. The ethylene terephthalate-based thermoplastic polyester is mainly composed of ester repeating units, in general, occupied by ethylene terephthalate units in 70 mol % or more thereof and preferably has a glass transition temperature (Tg) of 50° C. to 90° C. and a melting point (Tm) within a range of 200° C. to 275° C. Polyethylene terephthalate is, as an ethylene terephthalate-based thermoplastic polyester, excellent in, for example, pressure resistance, heat resistance, and heat and pressure resistance. In addition to ethylene terephthalate units, copolymer polyesters composed of dicarboxylic acids, such as isophthalic acid or naphthalenedicarboxylic acid, and a small amount of ester units of diols, such as propylene glycol, can be used.

Examples of the dicarboxylic acid may include saturated aliphatic dicarboxylic acids, such as oxalic acid, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 1,3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 2,5-norbornanedicarboxylic acid, and dimer acid, and ester-forming derivatives thereof; unsaturated aliphatic dicarboxylic acids, such as fumaric acid, maleic acid, and itaconic acid, and ester-forming derivatives thereof; naphthalenedicarboxylic acids, such as orthophthalic acid, isophthalic acid, terephthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid; aromatic dicarboxylic acids, such as 4,4'-biphenyldicarboxylic acid, 4,4'-biphenylsulfonedicarboxylic acid, 4,4'- biphenyletherdicarboxylic acid, 1,2-bis(phenoxy)ethane-p, p'-dicarboxylic acid, and anthracenedicarboxylic acid, and ester-forming derivatives thereof; and metal sulfonate group-containing aromatic dicarboxylic acids, such as 5-sodium sulfo-isophthalic acid, 2-sodium sulfo-terephthalic acid, 5-lithium sulfo-isophthalic acid, 2-lithium sulfo-terephthalic acid, 5-potassium sulfo-isophthalic acid, and 2-potassium sulfo-terephthalic acid, and lower alkyl ester derivatives thereof.

Among the use of the above-mentioned dicarboxylic acids, the use of terephthalic acid, isophthalic acid, and naphthalenedicarboxylic acids is particularly preferred, from the viewpoint of, for example, the physical properties resulting from the polyesters. The carboxylic acid may be optionally copolymerized with another dicarboxylic acid.

Examples of polyvalent carboxylic acids other than these dicarboxylic acids may include ethanetricarboxylic acid, propanetricarboxylic acid, butanetetracarboxylic acid, pyromellitic acid, trimellitic acid, trimesic acid, and 3,4,3',4'-biphenyltetracarboxylic acid, and ester-forming derivatives thereof.

Examples of the glycol may include aliphatic glycols, such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexanediol, 1,2-cyclohexanediol, 1,3-cyclohexanediol, 1,4-cyclohexanediol, 1,2-cyclohexane dimethanol, 1,3-cyclohexane dimethanol, 1,4-cyclohexane dimethanol, 1,4-cyclohexane diethanol, 1,10-decamethylene glycol, 1,12-dodecanediol, poly(ethylene glycol), poly(trimethylene glycol), and poly(tetramethylene glycol); and aromatic glycols, such as hydroquinone, 4,4'-dihydroxy bisphenol, 1,4-bis(β-hydroxyethoxy)benzene, 1,4-bis(β-hydroxyethoxyphenyl)sulfone, bis(p-hydroxyphenyl)ether, bis(p-hydroxyphenyl)sulfone, bis(p-hydroxyphenyl)methane, 1,2-bis(p-hydroxyphenyl)ethane, bisphenol A, bisphenol C, and 2,5-naphthalene diol, and glycols formed by adding an ethylene oxide to these glycols.

Among the above-mentioned glycols, in particular, ethylene glycol, 1,3-propyleneglycol, 1,4-butylene glycol, or 1,4-cyclohexane dimethanol can be preferably used as a main component.

Examples of polyhydric alcohols other than these glycols may include trimethylol methane, trimethylol ethane, trimethylol propane, pentaerythritol, glycerol, and hexane triol.

Examples of the hydroxycarboxylic acid may include lactic acid, citric acid, malic acid, tartaric acid, hydroxyacetic acid, 3-hydroxybutyric acid, p-hydroxybenzoic acid, p-(2-hydroxyethoxyl)benzoic acid, and 4-hydroxycyclohexanecarboxylic acid, and ester-forming derivatives thereof.

Examples of the cyclic ester may include ε-caprolactone, β-propiolactone, β-methyl-β-propiolactone, δ-valerolactone, glycolide, and lactide.

Examples of the ester-forming derivatives of polyvalent carboxylic acid and hydroxycarboxylic acid may include alkyl esters, acid chlorides, and acid anhydrides thereof.

Among them, preferred are polyesters having terephthalic acid or its ester-forming derivative or naphthalenedicarboxylic acid or its ester-forming derivative as the main acid component and alkylene glycol as the main glycol component.

The polyester having terephthalic acid or its ester-forming derivative as the main acid components preferably contains the terephthalic acid or its ester-forming derivative in a total amount of 70 mol % or more, more preferably 80 mol % or more, and most preferably 90 mol % or more, based on the total amount of the acid components. Similarly, the polyester having naphthalenedicarboxylic acid or its ester-forming derivative as the main acid components contains the naphthalenedicarboxylic acid or its ester-forming derivative in a total amount of 70 mol % or more, more preferably 80 mol % or more, and most preferably 90 mol % or more, based on the total amount of the acid components.

Among the above-mentioned naphthalenedicarboxylic acids and ester-forming derivatives thereof, preferred are 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid, and ester-forming derivatives thereof exemplified as the dicarboxylic acids.

The polyester having alkylene glycol as the main glycol component contains the alkylene glycol in a total amount of 70 mol % or more, more preferably 80 mol % or more, and most preferably 90 mol % or more, based on the total amount of the glycol components. The alkylene glycol herein may contain a substituent or an alicyclic structure in the molecular chain.

The copolymer component other than the above-mentioned terephthalic acid/ethylene glycol is, from the viewpoint of achieving transparency and moldability simultaneously, preferably at least one selected from the group consisting of isophthalic acid, 2,6-naphthalenedicarboxylic acid, diethylene glycol, neopentylglycol, 1,4-cyclohexane dimethanol, 1,2-propanediol, 1,3-propanediol, and 2-methyl-1,3-propanediol, and more preferably at least one selected from the group consisting of isophthalic acid, diethylene glycol, neopentylglycol, and 1,4-cyclohexane dimethanol.

A preferred example of the polyester contained in the oxygen-absorbing composition is a polyester having a main repeating unit of ethylene terephthalate, more preferably a linear polyester containing 70 mol % or more of ethylene terephthalate units, further preferably a linear polyester containing 80 mol % or more of ethylene terephthalate units, and further preferably a linear polyester containing 90 mol % or more of ethylene terephthalate units.

Another preferred example of the polyester contained in the oxygen-absorbing composition is a polyester having a main repeating unit of ethylene-2,6-naphthalate, more preferably a linear polyester containing 70 mol % or more of ethylene-2,6-naphthalate units, further preferably a linear polyester containing 80 mol % or more of ethylene-2,6-naphthalate units, and further preferably a linear polyester containing 90 mol % or more of ethylene-2,6-naphthalate units.

Another preferred example of the polyester contained in the oxygen-absorbing composition is a linear polyester containing 70 mol % or more of propylene terephthalate units, a linear polyester containing 70 mol % or more of propylene naphthalate units, a linear polyester containing 70 mol % or more of 1,4-cyclohexanedimethylene terephthalate units, a linear polyester containing 70 mol % or more of butylene naphthalate units, or a linear polyester containing 70 mol % or more of butylene terephthalate units.

From the viewpoint of achieving transparency and moldability simultaneously, particularly preferred combinations of whole polyesters are a combination of terephthalic acid/isophthalic acid/ethylene glycol, a combination of terephthalic acid/ethylene glycol/1,4-cyclohexane dimethanol, and a combination of terephthalic acid/ethylene glycol/neopentylglycol. Understandably, the above-mentioned polyesters may contain a small amount (5 mol % or less) of diethylene glycol generated by dimerization of ethylene glycol during esterification (transesterification) reaction or polycondensation reaction.

Other preferred examples of the polyester contained in the oxygen-absorbing composition may include poly(glycolic acid) prepared by polycondensation of glycolic acid or methyl glycolate or by ring-opening polycondensation of glycolide. The poly(glycolic acid) may one copolymerized with another component such as lactide.

<Polyamide>

Examples of the polyamide contained in the oxygen-absorbing composition may include a polyamide having a main constitutional unit derived from a lactam or an aminocarboxylic acid, an aliphatic polyamide having a main constitutional unit derived from an aliphatic diamine and an aliphatic dicarboxylic acid, a partially aromatic polyamide having a main constitutional unit derived from an aliphatic diamine and an aromatic dicarboxylic acid, and a partially aromatic polyamide having a main constitutional unit derived from an aromatic diamine and an aliphatic dicarboxylic acid. The polyamide herein may be optionally copolymerized with a monomer unit other than the main constitutional unit.

Examples of the lactam or aminocarboxylic acid may include lactams, such as ε-caprolactam and laurolactam; aminocarboxylic acids, such as aminocaproic acid and aminoundecanoic acid; and aromatic aminocarboxylic acids, such as para-aminomethylbenzoic acid.

Examples of the aliphatic diamine may include aliphatic diamines having 2 to 12 carbon atoms and functional derivatives thereof, and alicyclic diamines. The aliphatic diamine may be a linear aliphatic diamine or a branched linear aliphatic diamine. Examples of the linear aliphatic diamine may include aliphatic diamines, such as ethylenediamine, 1-methylethylenediamine, 1,3-propylenediamine, tetramethylenediamine, pentamethylenediamine, hexamethylenediamine, heptamethylenediamine, octamethylenediamine, nonamethylenediamine, decamethylenediamine, undecamethylenediamine, and dodecamethylenediamine. Examples of the alicyclic diamine may include cyclohexanediamine, 1,3-bis(aminomethyl)cyclohexane, and 1,4-bis(aminomethyl)cyclohexane.

Examples of the aliphatic dicarboxylic acid may include linear aliphatic dicarboxylic acids and alicyclic dicarboxylic acids. In particular, linear aliphatic dicarboxylic acids including alkylene groups having 4 to 12 carbon atoms are preferred. Examples of the linear aliphatic dicarboxylic acid may include adipic acid, sebacic acid, malonic acid, succinic acid, glutaric acid, pimelic acid, suberic acid, azelaic acid, undecanoic acid, undecanedioic acid, dodecanedioic acid, and dimer acid, and functional derivatives thereof. Examples of the alicyclic dicarboxylic acid may include 1,4-cyclohexanedicarboxylic acid, hexahydroterephthalic acid, and hexahydroisophthalic acid.

Examples of the aromatic diamine may include metaxylylenediamine, para-xylylenediamine, and para-bis(2-aminoethyl)benzene.

Examples of the aromatic dicarboxylic acid may include terephthalic acid, isophthalic acid, phthalic acid, 2,6-naphthalenedicarboxylic acid, diphenyl-4,4'-dicarboxylic acid, and diphenoxyethanedicarboxylic acid, and functional derivatives thereof.

Examples of the polyamide may include polyamide 4, polyamide 6, polyamide 10, polyamide 11, polyamide 12, polyamide 4,6, polyamide 6,6, polyamide 6,10, polyamide 6T, polyamide 9T, polyamide 6IT, poly(meta-xylylene adipamide) (polyamide MXD6), isophthalic acid copolymerized poly(meta-xylylene adipamide) (polyamide MXD6I), poly(meta-xylylene sebacamide) (polyamide MXD10), poly(meta-xylylene dodecanamide) (polyamide MXD12), poly(1,3-bis aminocyclohexane adipamide) (polyamide BAC6), and poly(para-xylylene sebacamide) (polyamide PXD10). More preferred examples of the polyamide may include polyamide 6, polyamide MXD6, and polyamide MXD6I.

The copolymer component that may be copolymerized with the polyamide is a polyether having at least one terminal amino group or terminal carboxyl group and having a number-average molecular weight of 2000 to 20000, an organic carboxylate of a polyether having the terminal amino group, or an amino salt of a polyether having the terminal carboxyl group. Examples thereof may include bis(aminopropyl)poly(ethylene oxide) (polyethylene glycol having a number-average molecular weight of 2000 to 20000).

The partially aromatic polyamide may contain a constitutional unit derived from a tri- or more-basic polyvalent carboxylic acid, such as trimellitic acid or pyromellitic acid, within a range of being substantially linear.

<Ethylene-Vinyl Alcohol Copolymer>

The ethylene-vinyl alcohol copolymer contained in the oxygen-absorbing composition preferably has an ethylene content of 15 to 60 mol % and includes a vinyl acetate component having a degree of saponification of 90 mol % or more. The ethylene content is preferably 20 to 55 mol % and more preferably 29 to 44 mol %. The degree of saponification of the vinyl acetate component is preferably 95 mol % or more. The ethylene-vinyl alcohol copolymer may further contain a small amount of comonomer of α-olefin, such as propylene, isobutene, α-octene, α-dodecene, or α-octadecene, an unsaturated carboxylic acid or its salt, a partial alkyl ester, a complete alkyl ester, nitrile, an amide, an anhydride, or an unsaturated sulfonic acid or its salt.

<Plant-Derived Resin>

The plant-derived resin contained in the oxygen-absorbing composition may be any resin containing a plant-derived material, and the plant for the raw material is not specifically limited. Examples of the plant-derived resin may include aliphatic polyester-based biodegradable resins. Examples of the aliphatic polyester-based biodegradable resin may include poly(α-hydroxy acid), such as poly(glycolic acid) (PGA) and poly(lactic acid) (PLA); and polyalkylene alkanoate, such as poly(butylene succinate) (PBS) and poly(ethylene succinate) (PES).

<Chlorine-Containing Resin>

The chlorine-containing resin contained in the oxygen-absorbing composition may be any resin containing chlorine in its constitutional unit and can be a known resin. Examples of the chlorine-containing resin may include poly(vinyl chloride), poly(vinylidene chloride), and their copolymers with vinyl acetate, a maleic acid derivative, or higher alkyl vinyl ether.

Among the thermoplastic resins exemplified above, linear low-density polyethylene (LLDPE), ethylene-vinyl alcohol copolymer (EVOH), nylon 6 (PA6), polyethylene terephthalate (PET), and poly(vinyl chloride) (PVC) are preferably used as packaging materials for food.

The oxygen-absorbing composition may further optionally contain a radical generator or a photoinitiator for facilitating the oxygen absorption reaction. Examples of the radical generator may include a variety of N-hydroxyimide compounds, for example, but not limited to, N-hydroxysuccinimide, N-hydroxymaleimide, N,N'-dihydroxycyclohexanetetracarboxylic acid diimide, N-hydroxyphthalimide, N-hydroxytetrachlorophthalimide, N-hydroxytetrabromophthalimide, N-hydroxyhexahydrophthalimide, 3-sulfonyl-N-hydroxyphthalimide, 3-methoxycarbonyl-N-hydroxyphthalimide, 3-methyl-N-hydroxyphthalimide, 3-hydroxy-N-hydroxyphthalimide, 4-nitro-N-hydroxyphthalimide, 4-chloro-N-hydroxyphthalimide, 4-methoxy-N-hydroxyphthalimide, 4-dimethylamino-N-hydroxyphthalimide, 4-carboxy-N-hydroxyhexahydrophthalimide, 4-methyl-N-hydroxyhexahydrophthalimide, N-hydroxy HET acid imide, N-hydroxy High Mick acid imide, N-hydroxytrimellitic acid imide, and N,N-dihydroxypyromellitic acid dimide. Examples of the photoinitiator may include, but are not limited to, benzophenone and derivatives thereof, thiazine dyes, metal porphyrin derivatives, and anthraquinone derivatives. These radical generators and photoinitiators may be used alone or in combination of two or more thereof.

The oxygen-absorbing composition may contain a variety of additives known in the art within a range that does not impair the effects of the embodiments. Examples of such optional components may include, but are not limited to, fillers, such as calcium carbonate, clay, mica, and silica, desiccants, pigments, dyes, antioxidants, slipping agents, antistatic agents, stabilizers, plasticizers, and deodorants.

[Thermoplastic Resin Layer (Layer B)]

The thermoplastic resin layer (layer B) of the oxygen-absorbing medical multilayer laminate of the embodiment contains a thermoplastic resin (b). The content of the thermoplastic resin (b) in layer B can be appropriately determined and is not specifically limited, and is preferably 70% to 100% by mass, more preferably 80% to 100% by mass, and most preferably 90% to 100% by mass, based on the total amount of layer B.

The oxygen-absorbing medical multilayer laminate of the embodiment may include a first layer B and a second layer B and may further include another layer, and a plurality of layers of layer B may have the same or different structures. The thickness of layer B in the oxygen-absorbing medical multilayer laminate of the embodiment can be appropriately determined depending on the use and the desired performance. Although the thickness is not specifically limited, from the viewpoint of securing various physical properties, i.e., the strength, such as drop resistance, and flexibility, required in the multilayer laminate, the thickness is preferably 5 to 1000 µm, more preferably 10 to 800 µm, and most preferably 20 to 500 µm.

The thermoplastic resin (b) of layer B of the oxygen-absorbing medical multilayer laminate of the embodiment may be any thermoplastic resin without specific limitation and, for example, may be the same as or different from the thermoplastic resin (a) used in layer A described above. In addition, the thermoplastic resin (b) used in the first resin layer and the thermoplastic resin (b) used in the second resin layer may be the same or different. Layer B of the embodiment preferably contains at least one selected from the group consisting of a polyolefin, a polyester, a polyamide, an ethylene-vinyl alcohol copolymer, a plant-derived resin, and a chlorine-containing resin and more preferably contains at least one selected from the group consisting of a polyolefin, a polyester, a polyamide, a ethylene-vinyl alcohol copolymer, and a chlorine-containing resin. The content of the thermoplastic resin (b) used in layer B of the embodiment is preferably 50% to 100% by mass, more preferably 70% to 100% by mass, and most preferably 90% to 100% by mass, based on the total amount of layer B.

The exemplified thermoplastic resin (b) that can be used in layer B, i.e., polyolefins, polyesters, polyamides, ethylene-vinyl alcohol copolymers, plant-derived resins, and chlorine-containing resins, may be those exemplified as the thermoplastic resin that can be used in layer A.

Layer B of the oxygen-absorbing medical multilayer laminate of the embodiment may contain a variety of additives known in the art, in addition to the above-mentioned thermoplastic resins. Examples of such optional components may include, but are not limited to, desiccants, color pigments such as titanium oxide, dyes, antioxidants, slipping agents, antistatic agents, plasticizers, stabilizers, additives such as lubricants, fillers such as calcium carbonate, clay, mica, and silica, and deodorants.

[Other Layer]

The oxygen-absorbing medical multilayer laminate of the embodiment may further include an arbitrary layer, in addition to the above-described oxygen-absorbing layer (layer A) and the resin layer (layer B), depending on desired performance and other factors. Examples of such an arbitrary layer may include adhesive layers, metal foil, metal vapor deposition layers, and organic-inorganic films.

For example, from the viewpoint of further increasing the interlayer adhesion strength between adjacent two layers, an adhesive layer (layer AD) is preferably disposed between the two layers. The adhesive layer preferably contains a thermoplastic resin having adhesiveness. Examples of the thermoplastic resin having adhesiveness may include acid-modified polyolefin resins obtained by modifying polyolefin-based resins, such as polyethylene and polypropylene, with unsaturated carboxylic acids, such as acrylic acid, methacrylic acid, maleic acid, maleic anhydride, fumaric acid, and itaconic acid; and polyester-based thermoplastic elastomers mainly composed of polyester-based block copolymers. In addition, from the viewpoint of enhancing the adhesiveness to the above-described resin layer (layer B), preferred is a resin prepared by modifying a resin of the same type as the thermoplastic resin used in layer B. The adhesive layer may have any thickness, but from the viewpoint of securing molding processability while maintaining practical adhesion strength, the thickness is preferably 2 to 100 µm, more preferably 5 to 90 µm, and most preferably 10 to 80 µm.

In addition, from the viewpoint of further enhancing the gas barrier property, one surface of layer B is preferably provided with, for example, a metal vapor deposition layer or an organic-inorganic film. The metal vapor deposition layer is not specifically limited, and preferred is, for example, a film of a metal, such as aluminum or alumina, or an oxide thereof deposited on a resin film. Examples of the method for forming the vapor deposition film may include, but are not limited to, physical vapor deposition, such as vacuum vapor deposition, sputtering, or ion plating; and chemical vapor deposition, such as PECVD, and a known method can be employed. The vapor deposition film preferably has a thickness of 5 to 500 nm and more preferably 5 to 200 nm, from the viewpoint of, for example, the gas barrier property and bending resistance. The organic-inorganic film layer is not specifically limited, and is preferably, for example, a resin film coated with a silica-poly(vinyl alcohol) hybrid film prepared by a sol-gel method. The coating film preferably has a thickness of 100 nm to 50 µm and more preferably 1 to 15 µm, from the viewpoint of, for example, the gas barrier property and bending resistance.

[Production Process and Other Items]

The oxygen-absorbing medical multilayer container of the embodiment can be produced by a known method depending on, for example, the properties of each material and the desired shapes, and the method is not specifically limited. The oxygen-absorbing medical multilayer container can be produced by a variety of types of injection molding processes.

In injection molding processes of a multilayer, for example, a multilayer injection-molded product having a two-layer structure of A/B having a shape along the shape of the cavity of an injection mold can be produced with a molding apparatus equipped with two or more extruders and an injection mold by injecting a material for forming layer A and a material for forming layer B into the cavity from the respective injection cylinders through a mold hot runner. A multilayer injection-molded product having a three-layer structure of B/A/B can be produced by first injecting a material for forming layer B from an injection cylinder, subsequently injecting a material for forming layer A from another injection cylinder simultaneously with the material for forming layer B, and then injecting the material for forming layer B in an amount necessary for filling the cavity. A multilayer injection-molded product having a five-layer structure of B/A/B/A/B can be produced by first injecting a material for forming layer B, subsequently injecting a material for forming layer A alone, and lastly injecting the material for forming layer B in an amount necessary for filling the cavity. A multilayer injection-molded product having a five-layer structure of B1/B2/A/B2/B1 can be produced by first injecting a material for forming layer B1 from an injection cylinder, subsequently injecting a material for forming layer B2 from another injection cylinder, simultaneously with the material for forming layer B1, then injecting a material for forming layer A, simultaneously with the materials for forming layer B1 and layer B2, and then injecting the material for forming layer B1 in an amount necessary for filling the cavity.

The oxygen-absorbing medical multilayer container of the embodiment may have any thickness without specific limitation and is preferably 500 to 5000 µm, more preferably 700 to 4000 µm, and most preferably 800 to 3000 µm, from the viewpoint of enhancing the oxygen-absorbing performance and securing various physical properties, such as flexibility, required in the injection-molded product.

The oxygen-absorbing medical multilayer container of the embodiment used in a part of the components of a container for sealing absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. On this occasion, the injection-molded product of the embodiment itself may be molded into the shape of the container. Alternatively, the resulting injection-molded product can be fabricated into a container having a desired shape by secondary processing. The secondary processing can be, for example, blow molding. Considering that the oxygen-absorbing medical multilayer container of the embodiment expresses oxygen-absorbing performance, preferred is a storage container, such as an ampoule, a vial, or a prefilled syringe.

The multilayer molded product can be prepared by, for example, compression molding instead of injection molding by, for example, providing an oxygen-absorbing composition into a thermoplastic resin molten material, supplying the molten lump to a male mold and compressing it with a female mold, and cooling and solidifying the compression molded product to give a multilayer molded product.

Alternatively, the multilayer molded product can also be prepared by another method than by injection molding and compression molding. the multilayer molded product can also be prepared through extrusion blow molding by, for example, forming a cylindrical parison with an extrusion blow molding apparatus composed of a plurality of extruders and a cylindrical die, extruding the parison into a tube form, pinching the parison with molds, pinching off the bottom of the parison and fusing it, blowing the parison with high-pressure air before being cooled to inflate the parison into a multilayer molded product.

The usage of the oxygen-absorbing medical multilayer container of the embodiment is not specifically limited, and the medical container can be applied to a variety of uses in a variety of shapes. Preferred examples of the usage may include, but are not limited to, vials, ampoules, prefilled syringes, and vacuum blood collection tubes. Preferred usage will now be described in detail.

[Vial]

The oxygen-absorbing medical multilayer container of the embodiment can be used as a vial. In general, a vial is constituted of a bottle, a rubber stopper, and a cap. The bottle is filled with a drug solution and is fitted with the rubber stopper, and the cap is further tightened on the bottle to hermetically close the bottle. The oxygen-absorbing medical multilayer container of the embodiment can be used in the bottle portion of the vial.

The oxygen-absorbing medical multilayer container of the embodiment can be preferably molded into the bottle portion of a vial by, for example, injection blow molding or extrusion blow molding. As a specific example thereof, an injection blow molding process will now be described. For example, a multilayer injection-molded product having a three-layer structure of B/A/B having a shape along the shape of the cavity of an injection mold can be produced with a molding apparatus equipped with two or more extruders and an injection mold by injecting a material for forming layer A and a material for forming layer B into the cavity of the injection mold from the respective injection cylinders through a mold hot runner. A multilayer injection-molded product having a three-layer structure of B/A/B can be produced by first injecting a material for forming layer B from an injection cylinder, subsequently injecting a material for forming layer A from another injection cylinder simultaneously with the material for forming layer B, and then injecting the material for forming layer B in an amount necessary for filling the cavity. A multilayer injection-molded product having a five-layer structure of B/A/B/A/B can be produced by first injecting a material for forming layer B, subsequently injecting a material for forming layer A alone, and lastly injecting the material for forming layer B in an amount necessary for filling the cavity. A multilayer injection-molded product having a five-layer structure of B1/B2/A/B2/B1 can be produced by first injecting a material for forming layer B1 from an injection cylinder, subsequently injecting a material for forming layer B2 from another injection cylinder, simultaneously with the material for forming layer B1, then injecting a material for forming layer A, simultaneously with the materials for forming layer B1 and layer B2, and then injecting the material for forming layer B1 in an amount necessary for filling the cavity. In this injection blow molding, the thus-prepared multilayer injection-molded product is fit into a final-shape mold (blow mold) while maintaining the state heated to some extent and is inflated by feeding air thereinto to be brought into contact with the mold. The molded product is cooled and solidified to be molded into a bottle shape.

[Ampoule]

The oxygen-absorbing medical multilayer container of the embodiment can be used as an ampoule. In general, an ampoule is a small container having a narrow neck. The ampoule is filled with a drug solution and is then hermetically closed by sealing the end of the neck. The oxygen-absorbing medical multilayer container of the embodiment can be used in this ampoule (small container). The suitable method for forming the oxygen-absorbing medical multilayer container of the embodiment into an ampoule is, for example, injection blow molding or extrusion blow molding.

[Prefilled Syringe]

Furthermore, the oxygen-absorbing medical multilayer container of the embodiment can be used as the barrel of a prefilled syringe. A prefilled syringe barrel generally has a shape composed of a male luer taper nozzle to which an injection needle can be connected, a shoulder formed from the nozzle base end to the cylindrical portion, and a flange formed at the cylindrical portion base end. The nozzle is sealed with a cap during the storage of a drug, and a gasket connected to a plunger is inserted in the cylindrical portion. The oxygen-absorbing medical multilayer container of the embodiment can be used in this barrel.

The oxygen-absorbing medical multilayer container of the embodiment is suitably molded into the barrel of a prefilled syringe by, for example, injection molding. Specifically, first, a certain amount of a material for forming layer B is injected into the cavity of an injection mold. Subsequently, a certain amount of a material for forming layer A is injected, and a certain amount of a material for forming layer B is then injected again to produce the barrel as a multilayer injection-molded product. The barrel and the junction may be integrally molded or may be separately molded. After filling with a drug solution, the end of the junction needs to be sealed. The method of sealing is not specifically limited, and a known method can be employed. For example, the resin at the end of the junction is heated to a molten state and is fused by being pinched with, for example, a pair of pliers.

The thickness of the barrel container of a prefilled syringe can be appropriately determined depending on the intended purpose and the size thereof and is not specifically limited. In general, the thickness is preferably about 0.5 to 20 mm and more preferably about 0.5 to 5 mm, from the viewpoint of the long storage stability of a drug solution, moldability, and the operability of a syringe. The thickness may be constant or may vary. On the barrel surface, another gas barrier film or a light-shielding film may be formed for long storage stability. These arbitrary films and methods for forming them are described in, for example, Japanese Patent Laid-Open No. 2004-323058.

[Vacuum Blood Collection Tube]

In addition, the oxygen-absorbing medical multilayer container of the embodiment can be used as a vacuum blood collection tube. In general, a vacuum blood collection tube is composed of a tubular component and a stopper component. The oxygen-absorbing medical multilayer container of the embodiment can be used in this tubular component.

The oxygen-absorbing medical multilayer container of the embodiment is suitably molded into the tubular component of a vacuum blood collection tube by, for example, injection molding. Specifically, first, a certain amount of a material for forming layer B is injected into the cavity of an injection mold. Subsequently, a certain amount of a material for forming layer A is injected, and a certain amount of a material for forming layer B is then injected again to produce the tubular component as a multilayer injection-molded product.

[Article to be Stored]

The oxygen-absorbing medical multilayer container of the embodiment may be filled with any article to be stored (filling material) without specific limitation. The container can be filled with, for example, an arbitrary natural product or a compound, for example, a vitamin supplement, such as vitamin A, vitamin B2, vitamin B12, vitamin C, vitamin D, vitamin E, or vitamin K; an alkaloid, such as atropine; a hormone, such as adrenalin or insulin; a saccharide, such as glucose or maltose; an antibiotic, such as ceftriaxone, cephalosporin, or cyclosporine; or a benzodiazepine-based drug, such as oxazolam, flunitrazepam, clotiazepam, or clobazam. When the oxygen-absorbing medical multilayer container of the embodiment is filled with such a natural product or a compound, the amount of the natural product or the compound adsorbed to the medical container is small, and the medical container can prevent the natural product or the compound from being deteriorated by oxidation and can also prevent the solvent (e.g., water) from being transpirated.

Second Embodiment

[Oxygen-Absorbing Medical Multilayer Container]

The oxygen-absorbing medical multilayer container of the embodiment includes at least three layers including a first resin layer (layer B) containing a polyolefin (PO1), an oxygen-absorbing layer (layer A) containing an oxygen-absorbing composition, and a second resin layer (layer B) containing a polyolefin (PO2), in this order, wherein the oxygen-absorbing composition contains at least one compound having a tetralin ring represented by Formula (1), a transition metal catalyst, and a thermoplastic resin (a).

This oxygen-absorbing medical multilayer container is the same as the oxygen-absorbing medical multilayer container of the first embodiment except that a polyolefin (PO1) is used instead of the thermoplastic resin (b1) and that a polyolefin (PO2) is used instead of the thermoplastic resin (b2).

The oxygen-absorbing medical multilayer container of the embodiment can be used as, for example, a medical container for storing contents (article to be stored). In such a case, the medical container absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. This oxygen-absorbing medical multilayer container can absorb oxygen regardless of the presence or absence of water in the article to be stored and does not cause odor generation after oxygen absorption and can, therefore, be applied to a variety of medicinal products and medical supplies. Furthermore, when the contents (article to be stored) are a liquid such as an aqueous injection, the evaporation of water vapor from the inside of the container can be inhibited to prevent a change in concentration of the contents (article to be stored). In addition, the reduction in strength due to, for example, oxidation is significantly small even after oxygen absorption, and the strength of the oxygen-absorbing layer is maintained even in use for a long period of time. Consequently, an oxygen-absorbing medical multilayer container substantially not causing interlayer peeling can also be achieved. Accordingly, the oxygen-absorbing medical multilayer container of the present invention is particularly useful for storage of medicinal products, biological medicines, medical supplies, and other articles that are required to be stored in a low concentration of oxygen.

The oxygen-absorbing medical multilayer container of the embodiment includes at least three layers including a first resin layer (layer B) at least containing a thermoplastic resin, and an oxygen-absorbing layer (layer A) of an oxygen-absorbing composition, and a second resin layer (layer B) at least containing a thermoplastic resin, in this order.

The oxygen-absorbing medical multilayer container of the embodiment absorbs oxygen inside the container and also absorbs oxygen from the outside of the container, if oxygen passes through or penetrates the wall of the container, even if the amount of the oxygen is small, and can thereby prevent the contents (article to be stored) from, for example, being deteriorated by oxygen.

The oxygen-absorbing medical multilayer container of the embodiment may have any layer structure in which the layers are arranged in an order of B/A/B, and the number and types of the oxygen-absorbing layer (layer A) and the resin layer (layer B) are not are not particularly limited. For example, the structure may be composed of one layer of layer A, two layers of layer B1 and two layers of layer B2 to form a five-layer structure of B1/B2/A/B2/B1, or may be composed of one layer of layer A and two-material two-layer of layer B1 and layer B2 to form a three-layer structure of B1/A/B2. The oxygen-absorbing medical multilayer container of the embodiment can optionally include an arbitrary layer, such as an adhesive layer (layer AD), to form, for example, a seven-layer structure of B1/AD/B2/A/B2/AD/B1.

[Oxygen-Absorbing Layer (Layer A)]

The oxygen-absorbing layer (layer A) in the oxygen-absorbing medical multilayer container of the embodiment is a layer containing an oxygen-absorbing composition that contains at least one compound having a tetralin ring represented by Formula (1) (hereinafter, also simply referred to as "tetralin compound"), a transition metal catalyst, and a thermoplastic resin (a).

<Compound Having a Tetralin Ring>

The compound having a tetralin ring described in the first embodiment can be appropriately used.

<Transition Metal Catalyst>

The transition metal catalyst described in the first embodiment can be appropriately used.

<Thermoplastic Resin (a)>

The thermoplastic resin (a) described in the first embodiment can be appropriately used.

[Resin Layer (Layer B)]

The resin layers (layer B: first resin layer and second resin layer) of the oxygen-absorbing medical multilayer container of the embodiment contain polyolefins (PO1 and PO2).

<Polyolefin>

Examples of the polyolefins (PO1 and PO2) used in layer B of the embodiment include, but are not limited to, polyethylenes (low-density polyethylene, medium-density polyethylene, high-density polyethylene, straight-chain (linear) low-density polyethylene), polypropylene, polybutene-1, poly-4-methylpentene-1, copolymers of ethylene and α-olefin, copolymers of propylene and α-olefin, ethylene-α,β-unsaturated carboxylic acid copolymers, and ethylene-α,β-unsaturated carboxylic acid ester copolymers. Examples of these polyolefins include those exemplified as the thermoplastic resin preferably used in layer B of the oxygen-absorbing multilayer laminate of the second embodiment. Particularly preferred resins are cycloolefin ring-opened polymers of norbornene or tetracyclododecene or derivatives thereof and hydrogenated products of the polymers; and copolymers having cyclopentyl residues or substituted cyclopentyl residues inserted in their molecular chains by polymerization of cycloolefin, such as norbornene or tetracyclododecene or a derivative thereof, and ethylene or propylene. Here, the cycloolefin may be of a monocycle or a polycycle. Thermoplastic norbornene-based resins and thermoplastic tetracyclododecene-based resins are more preferred examples. Examples of the thermoplastic norbornene-based resin may include ring-opened polymers of norbornene-based monomers, hydroge-added products thereof, addition polymers of norbornene-based monomers, and addition polymers of norbornene-based monomers and olefins. Examples of the thermoplastic tetracyclododecene-based resin may include ring-opened polymers of tetracyclododecene-based monomers, hydrogenated products thereof, addition polymers of tetracyclododecene-based monomers, and addition polymers of tetracyclododecene-based monomers and olefins. The thermoplastic norbornene-based resins are described in, for example, Japanese Patent Laid-Open Nos. H03-01488, H03-122137, and H04-063807. The polyolefin (PO1) and the polyolefin (PO2) may be the same or different.

Cycloolefin polymers (COPs) prepared through ring-opening polymerization of norbornene and hydrogenation are particularly preferred. In addition, cycloolefin copolymers (COCs), e.g., copolymers, the raw materials of which are norbornene and olefin such as ethylene; and copolymers, the raw materials of which are tetracyclododecene and olefin such as ethylene, are also particularly preferred. These COPs and COCs are described in, for example, Japanese Patent Laid-Open Nos. H05-317411 and H05-300939.

The COP is commercially available as, for example, "Zeonex®" or "Zeonor®" manufactured by Zeon Corporation or "Daikyo Resin CZ®" manufactured by Daikyo Seiko, Ltd. The COC is commercially available as, for example, "Apel®" manufactured by Mitsui Chemicals, Incorporated. The COP and the COC show the characteristics as polyolefin resins in chemical properties, such as heat resistance and light resistance, and in chemical resistance and show the characteristics as amorphous resins in physical properties, such as mechanical properties, melting, flow properties, and dimensional accuracy. Thus, the COP and the COC are particularly preferred materials.

The first resin layer and the second resin layer may further contain a thermoplastic resin, in addition to the polyolefins. Such additional thermoplastic resin can be, for example, the thermoplastic resin other than polyolefin that can be used in layer A described above. Such a thermoplastic resin is preferably at least one selected from the group consisting of polyesters, polyamides, ethylene-vinyl alcohol copolymers, plant-derived resins, and chlorine-containing resins. The content of the thermoplastic resin used in layer B of the embodiment is preferably 50% to 100% by mass, more preferably 70% to 100% by mass, and most preferably 90% to 100% by mass, based on the total amount of layer B.

In the oxygen-absorbing medical multilayer container of the embodiment, a plurality of layers of layer B may be the same as or different from one another. In the oxygen-absorbing medical multilayer container of the embodiment, the thickness of layer B can be appropriately determined depending on the use and the desired performance. Although the thickness is not specifically limited, from the viewpoint of securing various physical properties, i.e., the strength, such as drop resistance, and flexibility, required in the multilayer laminate, the thickness is preferably 5 to 1000 μm, more preferably 10 to 800 μm, and most preferably 20 to 500 μm.

Layer B of the oxygen-absorbing medical multilayer container of the embodiment may contain a variety of additives known in the art, in addition to the above-mentioned thermoplastic resins. Examples of such optional components may include, but are not limited to, desiccants, color pigments such as titanium oxide, dyes, antioxidants, slipping agents, antistatic agents, plasticizers, stabilizers, additives such as lubricants, fillers such as calcium carbonate, clay, mica, and silica, and deodorants.

[Other Layer]

The oxygen-absorbing medical multilayer laminate of the embodiment may further include an arbitrary layer, in addition to the above-described oxygen-absorbing layer (layer A) and resin layer (layer B), depending on desired performance and other factors. Examples of such an arbitrary layer may include adhesive layers, metal foil, metal vapor deposition layers, and organic-inorganic films. As these layers, the layers described in the paragraph "other layer" of the first embodiment can be appropriately used.

[Production Process and Other Items]

The oxygen-absorbing medical multilayer container of the embodiment can be produced by a known method depending on, for example, the properties of each material and the desired shapes, and the method is not specifically limited. The oxygen-absorbing medical multilayer container can be produced by a variety of types of injection molding processes. The detailed description of general injection molding of a multilayer laminate is the same as that described in the first embodiment, and duplicated description is omitted.

The oxygen-absorbing medical multilayer container of the embodiment may have any thickness without specific limitation and is preferably 500 to 5000 µm, more preferably 700 to 4000 µm, and most preferably 800 to 3000 µm, from the viewpoint of enhancing the oxygen-absorbing performance and securing various physical properties, such as flexibility, required in the injection-molded product.

The oxygen-absorbing medical multilayer container of the embodiment used in a part of the components of a container for sealing absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. On this occasion, the injection-molded product of the embodiment itself may be molded into the shape of a container. Alternatively, the resulting injection-molded product can be fabricated into a container having a desired shape by secondary processing. The secondary processing can be, for example, blow molding. Considering that the oxygen-absorbing medical multilayer container of the embodiment expresses oxygen-absorbing performance, preferred is a storage container, such as an ampoule, a vial, or a prefilled syringe.

The methods other than injection molding are the same as that described in the first embodiment, and duplicated description is omitted.

The usage of the oxygen-absorbing medical multilayer container of the embodiment is not specifically limited, and the medical container can be applied to a variety of uses and in a variety of shapes. Preferred examples of the usage may include, but are not limited to, vials, ampoules, prefilled syringes, and vacuum blood collection tubes. The details of the vials, ampoules, prefilled syringes, and vacuum blood collection tubes are the same as those described in the first embodiment, and duplicated description is omitted.

[Article to be Stored]

The oxygen-absorbing medical multilayer container of the embodiment may be filled with any article to be stored (filling material) without specific limitation. The details of the article to be stored are the same as those described in the first embodiment, and duplicated description is omitted.

Third Embodiment

[Oxygen-Absorbing Medical Multilayer Container]

The oxygen-absorbing medical multilayer container of the embodiment includes at least three layers including a first resin layer containing a polyester (PES1), an oxygen-absorbing layer containing an oxygen-absorbing composition, and a second resin layer containing a polyester (PES2), in this order. The oxygen-absorbing composition contains at least one compound having a tetralin ring represented by Formula (1), a transition metal catalyst, and a thermoplastic resin.

This oxygen-absorbing medical multilayer container is the same as that in the first embodiment except that a polyester (PES1) is used instead of the thermoplastic resin (b1) and that a polyester (PES2) is used instead of the thermoplastic resin (b2).

The oxygen-absorbing medical multilayer container of the embodiment can be used as, for example, a medical container for storing the contents (article to be stored). In such a case, the medical container absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. This oxygen-absorbing medical multilayer container can absorb oxygen regardless of the presence or absence of water in the article to be stored and shows significantly suppressed generation of low-molecular-weight compounds after oxygen absorption and can, therefore, be applied to a variety of medicinal products and medical supplies. In addition, the reduction in strength due to, for example, oxidation is significantly small even after oxygen absorption, and the strength of the oxygen-absorbing layer is maintained even in use for a long period of time. Consequently, an oxygen-absorbing medical multilayer container substantially not causing interlayer peeling can also be achieved. Accordingly, the oxygen-absorbing medical multilayer container of the present invention is particularly useful for storing medicinal products, biological medicines, medical supplies, and other articles that are required to be stored in a low concentration of oxygen.

The oxygen-absorbing medical multilayer container of the embodiment includes at least three layers including a first resin layer (layer B) at least containing a polyester (PES1), an oxygen-absorbing layer (layer A) of an oxygen-absorbing composition, and a second resin layer (layer B) at least containing a polyester (PES2), in this order.

The oxygen-absorbing medical multilayer container of the embodiment absorbs oxygen inside the container and also absorbs oxygen from the outside of the container, if oxygen passes through or penetrates the wall of the container, even if the amount of the oxygen is small, and can thereby prevent the contents (article to be stored) from, for example, being deteriorated by oxygen.

The oxygen-absorbing medical multilayer container of the embodiment may have any layer structure in which the layers are arranged in an order of B/A/B, and the number and types of the oxygen-absorbing layer (layer A) and the resin layer (layer B) containing a polyester are not particularly limited. For example, the structure may be composed of one layer of layer A, two layers of layer B1 and two layers of layer B2 to form a five-layer structure of B1/B2/A/B2/B1, or may be composed of one layer of layer A and two-material two-layer of layer B1 and layer B2 to form a three-layer structure of B1/A/B2. The oxygen-absorbing medical multilayer container of the embodiment can optionally include an arbitrary layer, such as an adhesive layer (layer AD), to form, for example, a seven-layer structure of B1/AD/B2/A/B2/AD/B1.

[Oxygen-Absorbing Layer (Layer A)]

The oxygen-absorbing layer (layer A) of the oxygen-absorbing medical multilayer container of the embodiment is a layer containing an oxygen-absorbing composition that contains at least one compound having a tetralin ring represented by Formula (1) (hereinafter, also simply referred to as "tetralin compound"), a transition metal catalyst, and a thermoplastic resin.

<Compound Having a Tetralin Ring>

The compound having a tetralin ring described in the first embodiment can be appropriately used.

<Transition Metal Catalyst>

The transition metal catalyst used in the oxygen-absorbing composition of the embodiment can be appropriately selected from known catalysts that can function as catalysts for the oxidation reaction of the compound having a tetralin ring and is not specifically limited. As the transition metal catalyst, that described in the first embodiment can be appropriately used. In the embodiment, the above-described compound, the transition metal catalyst, and the thermoplastic resin (a) can be mixed by a known method and are preferably kneaded with an extruder, which allows the use of an oxygen-absorbing composition in a satisfactory dispersion state.

<Thermoplastic Resin (a)>

The oxygen-absorbing composition of the embodiment contains a thermoplastic resin. On this occasion, the above-described compound and the transition metal catalyst may be contained in the oxygen-absorbing composition in any forms without specific limitation. For example, the compound and the transition metal catalyst may be directly contained in the thermoplastic resin, or the compound and the transition metal catalyst supported on the above-described support material may be contained in the thermoplastic resin. As the thermoplastic resin (a), that described in the first embodiment can be appropriately used.

[Resin Layer (Layer B) Containing Polyester]

The resin layer (layer B) in the oxygen-absorbing medical multilayer container of the embodiment is a layer containing polyesters (PES1 and PES2).

Examples of the polyesters (PES1 and PES2) used in layer B of the oxygen-absorbing multilayer laminate of the embodiment may include polyesters composed of one or two or more polyvalent carboxylic acids selected from polyvalent carboxylic acids including dicarboxylic acids and their ester-forming derivatives and one or two or more polyhydric alcohols selected from polyhydric alcohols including glycols; polyesters composed of hydroxycarboxylic acids and their ester-forming derivatives; and polyesters composed of cyclic esters. Polyester PES1 and polyester PES2 may be the same or different.

Examples of the dicarboxylic acid may include saturated aliphatic dicarboxylic acids, such as oxalic acid, malonic acid, succinic acid, glutaric acid, adipic acid, pimelic acid, suberic acid, azelaic acid, sebacic acid, decanedicarboxylic acid, dodecanedicarboxylic acid, tetradecanedicarboxylic acid, hexadecanedicarboxylic acid, 1,3-cyclobutanedicarboxylic acid, 1,3-cyclopentanedicarboxylic acid, 1,2-cyclohexanedicarboxylic acid, 1,3-cyclohexanedicarboxylic acid, 1,4-cyclohexanedicarboxylic acid, 2,5-norbornanedicarboxylic acid, and dimer acid, and ester-forming derivatives thereof; unsaturated aliphatic dicarboxylic acids, such as fumaric acid, maleic acid, and itaconic acid, and ester-forming derivatives thereof; naphthalenedicarboxylic acids, such as orthophthalic acid, isophthalic acid, terephthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid; aromatic dicarboxylic acids, such as 4,4'-biphenyldicarboxylic acid, 4,4'-biphenylsulfonedicarboxylic acid, 4,4'-biphenyletherdicarboxylic acid, 1,2-bis(phenoxy)ethane-p,p'-dicarboxylic acid, and anthracenedicarboxylic acid, and ester-forming derivatives thereof; and metal sulfonate group-containing aromatic dicarboxylic acids, such as 5-sodium sulfo-isophthalic acid, 2-sodium sulfo-terephthalic acid, 5-lithium sulfo-isophthalic acid, 2-lithium sulfo-terephthalic acid, 5-potassium sulfo-isophthalic acid, and 2-potassium sulfo-terephthalic acid, and lower alkyl ester derivatives thereof.

Among the above-mentioned dicarboxylic acids, terephthalic acid, isophthalic acid, naphthalenedicarboxylic acids, and their ester-forming derivatives are particularly preferred, from the viewpoint of, for example, the physical properties of the resulting polyesters. Specifically, the polyester more preferably includes units derived from one or more dicarboxylic acids selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid, and ester-forming derivatives thereof. The polyester may be optionally copolymerized with another dicarboxylic acid. The total amount of these repeating units mentioned above is preferably 70 mol % or more, more preferably 90 mol % or more, of the dicarboxylic acid units of the polyester.

Examples of polyvalent carboxylic acids other than these dicarboxylic acids may include ethanetricarboxylic acid, propanetricarboxylic acid, butanetetracarboxylic acid, pyromellitic acid, trimellitic acid, trimesic acid, and 3,4,3',4'-biphenyltetracarboxylic acid, and ester-forming derivatives thereof.

Examples of the glycol may include aliphatic glycols, such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentyl glycol, 1,6-hexanediol, 1,2-cyclohexanediol, 1,3-cyclohexanediol, 1,4-cyclohexanediol, 1,2-cyclohexane dimethanol, 1,3-cyclohexane dimethanol, 1,4-cyclohexane dimethanol, 1,4-cyclohexane diethanol, 1,10-decamethylene glycol, 1,12-dodecanediol, poly(ethylene glycol), poly(trimethylene glycol), and poly(tetramethylene glycol); and aromatic glycols, such as hydroquinone, 4,4'-dihydroxy bisphenol, 1,4-bis(β-hydroxyethoxy)benzene, 1,4-bis(3-hydroxyethoxyphenyl) sulfone, bis(p-hydroxyphenyl) ether, bis(p-hydroxyphenyl)sulfone, bis(p-hydroxyphenyl)methane, 1,2-bis(p-hydroxyphenyl)ethane, bisphenol A, bisphenol C, and 2,5-naphthalene diol, and glycols formed by adding ethylene oxide to these glycols.

Among the above-mentioned glycols, in particular, ethylene glycol, 1,3-propylene glycol, 1,4-butylene glycol, or 1,4-cyclohexane dimethanol can be preferably used as a main component.

Examples of polyhydric alcohols other than these glycols may include trimethylol methane, trimethylol ethane, trimethylol propane, pentaerythritol, glycerol, and hexane triol.

Examples of the hydroxycarboxylic acid may include lactic acid, citric acid, malic acid, tartaric acid, hydroxyacetic acid, 3-hydroxybutyric acid, p-hydroxybenzoic acid, p-(2-hydroxyethoxyl)benzoic acid, and 4-hydroxycyclohexanecarboxylic acid, and ester-forming derivatives thereof.

Examples of the cyclic ester may include ε-caprolactone, β-propiolactone, β-methyl-β-propiolactone, δ-valerolactone, glycolide, and lactide.

Examples of the above-mentioned ester-forming derivative may include alkyl esters, acid chlorides, and acid anhydrides thereof.

Among them, preferred are polyesters having terephthalic acid or its ester-forming derivative or naphthalenedicarboxylic acid or its ester-forming derivative as the main acid component and alkylene glycol as the main glycol component.

In the dicarboxylic acid units of the polyester, preferably 70 mol % or more, more preferably 80 mol % or more, and most preferably 90 mol % or more of the units are derived from terephthalic acid. Such a polyester is preferably a linear polyester.

In the dicarboxylic acid units of the polyester, preferably 70 mol % or more, more preferably 80 mol % or more, and most preferably 90 mol % or more of the units are derived from 2,6-naphthalenedicarboxylic acid. Such a polyester is preferably a linear polyester.

The polyester having alkylene glycol as the main glycol component contains the alkylene glycol in a total amount of preferably 70 mol % or more, more preferably 80 mol % or more, and most preferably 90 mol % or more, based on the total amount of all glycol components. The alkylene glycol herein may contain a substituent or an alicyclic structure in the molecular chain.

Other preferred examples of the polyester used in layer B of the oxygen-absorbing multilayer laminate of the embodiment may include poly(glycolic acid) prepared by polycondensation of glycolic acid or methyl glycolate or by ring-opening polycondensation of glycolide. The poly(glycolic acid) may be copolymerized with another component such as lactide.

The resin layer (layer B) containing polyester may further contain another thermoplastic resin, in addition to the polyester. Such an additional thermoplastic resin can be, for example, the thermoplastic resin other than the polyester used in layer A described above. Such a thermoplastic resin is preferably at least one resin selected from the group consisting of polyolefins, polyamides, ethylene-vinyl alcohol copolymers, plant-derived resins, and chlorine-containing resins. The amount of the thermoplastic resin used in layer B of the embodiment is preferably 50% to 100% by mass, more preferably 70% to 100% by mass, and most preferably 90% to 100% by mass, based on the total amount of layer B.

In the oxygen-absorbing medical multilayer container of the embodiment, a plurality of layers of layer B may be the same as or different from one another. In the oxygen-absorbing medical multilayer container of the embodiment, the thickness of layer B can be appropriately determined depending on the use and the desired performance. Although the thickness is not specifically limited, from the viewpoint of securing various physical properties, i.e., the strength, such as drop resistance, and flexibility, required in the medical multilayer container, the thickness is preferably 5 to 1000 μm, more preferably 10 to 800 μm, and most preferably 20 to 500 μm.

In addition, layer B of the oxygen-absorbing medical multilayer container of the embodiment may contain a variety of additives known in the art, in addition to the above-mentioned polyester and thermoplastic resin. Examples of such an arbitrary component may include, but are not limited to, desiccants, color pigments such as titanium oxide, dyes, antioxidants, slipping agents, antistatic agents, plasticizers, stabilizers, additives such as lubricants, fillers such as calcium carbonate, clay, mica, and silica, and deodorants. In particular, in the viewpoint of recycling and reprocessing offcuts generated during production, it is preferable to add an antioxidant to layer B.

[Other Layer]

The oxygen-absorbing medical multilayer laminate of the embodiment may further include an arbitrary layer, in addition to the above-described oxygen-absorbing layer (layer A) and the resin layer (layer B) containing polyester, depending on desired performance and other factors. Examples of such an arbitrary layer may include adhesive layers, metal vapor deposition layers, and organic-inorganic films. As the other layer, that described in the first embodiment can be appropriately used. The metal vapor deposition layer is not specifically limited, and is preferably a transparent vapor deposition film, such as silica or alumina, from the viewpoint of securing the visibility of the contents.

[Production Process and Other Items]

The oxygen-absorbing medical multilayer container of the embodiment can be produced by a known method depending on, for example, the properties of each material and the desired shapes, and the method is not specifically limited. The oxygen-absorbing medical multilayer container can be produced by a variety of types of injection molding processes. The detailed description of general injection molding of a multilayer laminate is the same as that described in the first embodiment, and duplicated description is omitted.

The oxygen-absorbing medical multilayer container of the embodiment may have any thickness without specific limitation and is preferably 500 to 5000 μm, more preferably 700 to 4000 μm, and most preferably 800 to 3000 μm, from the viewpoint of enhancing the oxygen-absorbing performance and securing various physical properties required in the medical container.

The oxygen-absorbing medical multilayer container of the embodiment used in a part of the components of a container for sealing absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen. On this occasion, the injection-molded product of the embodiment itself may be molded into the shape of a container. Alternatively, the resulting injection-molded product can be fabricated into a container having a desired shape by secondary processing. The secondary processing can be, for example, blow molding. Considering that the oxygen-absorbing medical multilayer container of the embodiment expresses oxygen-absorbing performance, preferred is a storage container, such as an ampoule, a vial, or a prefilled syringe.

The methods other than injection molding are the same as those described in the first embodiment, and duplicated description is omitted.

The usage of the oxygen-absorbing medical multilayer container of the embodiment is not specifically limited, and the medical container can be applied to a variety of uses and in a variety of shapes. Preferred examples of the usage may include, but are not limited to, vials, ampoules, prefilled syringes, and vacuum blood collection tubes. The details of the vials, ampoules, prefilled syringes, and vacuum blood collection tubes are the same as those described in the first embodiment, and duplicated description is omitted.

[Article to be Stored]

The article to be stored (filling material) filled in the oxygen-absorbing medical multilayer container of the embodiment is not specifically limited. The details of the article to be stored are the same as those described in the first embodiment, and duplicated description is omitted.

Fourth Embodiment

[Oxygen-Absorbing Prefilled Syringe]

The oxygen-absorbing prefilled syringe of the embodiment is an oxygen-absorbing prefilled syringe accommodating a drug in advance in a sealed condition and allowing the drug to be dispensed by releasing the sealed condition when used, wherein the prefilled syringe includes at least three layers including a first resin layer at least containing a thermoplastic resin (b1), an oxygen-absorbing layer containing an oxygen-absorbing composition, and a second resin layer at least containing a thermoplastic resin (b2), in this order; and the oxygen-absorbing composition contains at least one compound having a tetralin ring represented by Formula (1), a transition metal catalyst, and a thermoplastic resin (a).

The oxygen-absorbing prefilled syringe is the same as the container in any one of the first to third embodiments except that the oxygen-absorbing medical multilayer container accommodates a drug in a sealed condition in advance and allowing the drug to be dispensed by releasing the sealed condition when used.

The oxygen-absorbing prefilled syringe of the embodiment includes at least three layers including a first resin layer (layer B) at least containing a thermoplastic resin (b1), an oxygen-absorbing layer (layer A) containing an oxygen-absorbing composition, and a second resin layer (layer B) at least containing a thermoplastic resin (b2), in this order.

The oxygen-absorbing prefilled syringe of the embodiment absorbs oxygen inside the container and also absorbs oxygen from outside of the container, if oxygen passes through or penetrates the wall of the container, even if the amount of the oxygen is small, and can thereby prevent the contents (article to be stored) from, for example, being deteriorated by oxygen.

The oxygen-absorbing prefilled syringe of the embodiment may have any layer structure in which the layers are arranged in an order of B/A/B, and the number and types of the oxygen-absorbing layer (layer A) and the resin layer (layer B) are not particularly limited. For example, the structure may be composed of one layer of layer A, two layers of layer B1 and two layers of layer B2 to form a five-layer structure of B1/B2/A/B2/B1, or may be composed of one layer of layer A and two-material two-layer of layer B1 and layer B2 to form a three-layer structure of B1/A/B2. The oxygen-absorbing medical multilayer container of the embodiment can optionally include an arbitrary layer, such as an adhesive layer (layer AD), to form, for example, a seven-layer structure of B1/AD/B2/A/B2/AD/B1.

One mode of the oxygen-absorbing prefilled syringe of the embodiment is an injector (syringe) at least including a barrel for storing a drug solution, a junction for connecting an injection needle to an end of the barrel, and a plunger for extruding the drug solution when using, and being configured such that a drug solution is accommodated in the barrel in a sealed condition in advance and that the front end of the barrel is opened and an injection needle is mounted thereon when used. Such an oxygen-absorbing prefilled syringe is widely used because of its easiness in use. For example, this barrel can be made of the above-described oxygen absorbing multilayer laminate including at least three layers including a first resin layer, an oxygen-absorbing layer, and a second resin layer. The oxygen-absorbing prefilled syringe of the embodiment can be produced by molding as such an oxygen-absorbing multilayer laminate, the details of which will be described below.

The thickness of the barrel container of a prefilled syringe can be appropriately determined depending on the intended purpose and the size thereof and is not specifically limited. In general, the thickness is preferably about 0.5 to 20 mm and more preferably about 0.5 to 5 mm, from the viewpoint of the long storage stability of a drug solution, moldability, and the operability of a syringe. The thickness may be constant or may vary. On the barrel surface, another gas barrier film or a light-shielding film may be formed for long storage stability. These arbitrary films and methods for forming them are described in, for example, Japanese Patent Laid-Open No. 2004-323058.

[Oxygen-Absorbing Layer (Layer A)]

The oxygen-absorbing layer (layer A) of the oxygen-absorbing medical multilayer container of the embodiment contains an oxygen-absorbing composition containing at least one compound having a tetralin ring represented by Formula (1), such as one described above, a transition metal catalyst, and a thermoplastic resin (a). This oxygen-absorbing composition can significantly suppress the generation of low-molecular-weight compounds after oxygen absorption. Although the reasons thereof are not elucidated, for example, the following oxidation reaction mechanism is presumed.

It is presumed that the compound having a tetralin ring represented by Formula (1) is turned into a radical by removing a hydrogen atom at a benzylic position of the tetralin ring and that the carbon atom at the benzylic position is oxidized by the reaction between the radical and an oxygen atom to generate a hydroxy group or a ketone group. Consequently, in the oxygen-absorbing composition, the molecular chain of the oxygen-absorbing base compound is not cleaved by an oxidation reaction, unlike in existing technologies, and the structure of the oxygen-absorbing base compound is maintained to prevent generation of low-molecular-weight organic compounds.

<Compound Having a Tetralin Ring>

The compound having a tetralin ring described in the first embodiment can be appropriately used.

<Transition Metal Catalyst>

The transition metal catalyst used in the oxygen-absorbing composition of the embodiment can be appropriately selected from known catalysts that can function as catalysts for the oxidation reaction of the compound having a tetralin ring and is not specifically limited. As the transition metal catalyst, that described in the first embodiment can be appropriately used. In the embodiment, the above-described compound, the transition metal catalyst, and the thermoplastic resin (a) can be mixed by a known method and are preferably kneaded with an extruder, which allows the use of an oxygen-absorbing composition in a satisfactory dispersion state.

<Thermoplastic Resin (a)>

The oxygen-absorbing composition of the embodiment contains a thermoplastic resin (a). On this occasion, the above-described compound and the transition metal catalyst may be contained in the oxygen-absorbing composition in any forms without specific limitation. For example, the compound and the transition metal catalyst may be directly contained in the thermoplastic resin (a), or the compound and the transition metal catalyst supported on the above-described support material may be contained in the thermoplastic resin (a). As the thermoplastic resin (a), that described in the first embodiment can be appropriately used.

[Resin Layer (Layer B: First Resin Layer and Second Resin Layer)]

The first resin layer and the second resin layer (layer B) of the oxygen-absorbing prefilled syringe of the embodiment are layers containing a thermoplastic resin (b). The content of the thermoplastic resin (b) in each layer B can be appropriately determined and is not specifically limited, and is preferably 70% to 100% by mass, more preferably 80% to 100% by mass, and most preferably 90% to 100% by mass, based on the total amount of layer B.

The oxygen-absorbing prefilled syringe of the embodiment may include three or more layers of layer B. A plurality of layers of layer B may have the same or different structures. The thickness of layer B in the oxygen-absorbing prefilled syringe of the embodiment can be appropriately determined depending on the use and the desired performance. Although the thickness is not specifically limited, from the viewpoint of securing various physical properties, i.e., the strength, such as drop resistance, and flexibility, required in the prefilled syringe, the thickness is preferably 5 to 1000 µm, more preferably 10 to 800 µm, and most preferably 20 to 500 µm.

The thermoplastic resin (b) in layer B of the oxygen-absorbing prefilled syringe of the embodiment may be any thermoplastic resin without specific limitation and, for example, may be the same as or different from the thermoplastic resin (a) used in layer A described above. Layer B of the embodiment preferably contains at least one thermoplastic resin selected from the group consisting of polyolefins, polyesters, polyamides, ethylene-vinyl alcohol copolymers, plant-derived resins, and chlorine-containing resins. The content of the thermoplastic resin (b) used in layer B of the embodiment is preferably 50% to 100% by mass, more preferably 70% to 100% by mass, and most preferably 90% to 100% by mass, based on the total amount of layer B.

The polyolefin, polyester, polyamide, ethylene-vinyl alcohol copolymer, plant-derived resin, and chlorine-containing resin exemplified as the thermoplastic resin (b) that can be used in layer B can be those exemplified as the thermoplastic resin (a) that can be used in layer A.

Layer B of the oxygen-absorbing prefilled syringe of the embodiment may contain a variety of additives known in the art, in addition to the above-mentioned thermoplastic resins. Examples of such optional components may include, but are not limited to, desiccants, color pigments such as titanium oxide, dyes, antioxidants, slipping agents, antistatic agents, plasticizers, stabilizers, additives such as lubricants, fillers such as calcium carbonate, clay, mica, and silica, and deodorants. In particular, from the viewpoint of recycling and reprocessing offcuts generated during production, it is preferable to add an antioxidant to layer B.

[Other Layer]

The oxygen-absorbing prefilled syringe of the embodiment may further include an arbitrary layer, in addition to the above-described oxygen-absorbing layer (layer A) and the resin layer (layer B), depending on desired performance and other factors. Examples of such an arbitrary layer may include adhesive layers, metal vapor deposition layers, and organic-inorganic films.

For example, from the viewpoint of further increasing the interlayer adhesion strength between adjacent two layers, an adhesive layer (layer AD) is preferably disposed between the two layers. The adhesive layer preferably contains a thermoplastic resin having adhesiveness. Examples of the thermoplastic resin having adhesiveness may include acid-modified polyolefin resins obtained by modifying polyolefin-based resins, such as polyethylene and polypropylene, with unsaturated carboxylic acids, such as acrylic acid, methacrylic acid, maleic acid, maleic anhydride, fumaric acid, and itaconic acid; and polyester-based thermoplastic elastomers mainly composed of polyester-based block copolymers. In addition, from the viewpoint of enhancing the adhesiveness to the above-described resin layer (layer B), preferred is a resin prepared by modifying a resin of the same type as the thermoplastic resin used in layer B. The adhesive layer may have any thickness, but from the viewpoint of securing molding processability while maintaining the practical adhesion strength, the thickness is preferably 2 to 100 µm, more preferably 5 to 90 µm, and most preferably 10 to 80 µm.

In addition, from the viewpoint of further enhancing the gas barrier property, one surface of the above-described layer B is preferably provided with, for example, a metal vapor deposition layer or an organic-inorganic film. The metal vapor deposition layer is not specifically limited, and preferred is a transparent vapor deposition film of, for example, silica or alumina for securing the visibility of the contents. Examples of the method for forming the vapor deposition film may include, but are not limited to, physical vapor deposition, such as vacuum vapor deposition, sputtering, or ion plating; and chemical vapor deposition, such as PECVD, and a known method can be employed. The vapor deposition film preferably has a thickness of 5 to 500 nm and more preferably 5 to 200 nm, from the viewpoint of the gas barrier property. The organic-inorganic film layer is not specifically limited, and is preferably, for example, a silica-poly(vinyl alcohol) hybrid film prepared by a sol-gel method. The coating film preferably has a thickness of 100 nm to 50 µm and more preferably 1 to 15 µm, from the viewpoint of the gas barrier property.

[Production Process and Other Items]

A prefilled syringe barrel generally has a shape composed of a male luer taper nozzle to which an injection needle can be connected, a shoulder formed from the nozzle base end to the cylindrical portion, and a flange formed at the cylindrical portion base end. During the storage of a drug, the nozzle is sealed with a cap, and a gasket connected to a plunger is inserted in the cylindrical portion. The oxygen-absorbing prefilled syringe of the embodiment can be produced by molding the oxygen-absorbing multilayer laminate into a barrel shape by a known method that can be applied depending on, for example, the properties of each material and the desired shapes. Although the method is not specifically limited, injection molding is preferred.

Specifically, a certain amount of a resin for forming layer B is injected into a cavity from the gate disposed on the nozzle end of the barrel of the cavity, and a certain amount of a resin for forming layer A is then injected. The resin for forming layer B injected previously is cooled by the cavity and the wall of the core mold to form a skin layer, and the resin for forming layer A is formed into a core layer between the inner skin layer and the outer skin layer. A certain amount of the resin for forming layer B is then injected again to produce a barrel as a multilayer injection-molded product. The amount of the resin for forming layer B to be injected previously is preferably controlled such that layer A is formed to be situated nearer the cylindrical portion base end than the predetermined position of the barrel in which the gasket is inserted. The barrier property of the barrel can be further surely secured by forming the oxygen-absorbing layer (layer A) until the predetermined position in which the gasket is inserted. The amount of the resin to be injected for forming layer A is preferably controlled such that layer A is formed to be positioned nearer the nozzle end than the predetermined position to be sealed with a cap. The barrier property of the barrel can be further surely secured by forming the oxygen-absorbing layer (layer A) until the predetermined position to be sealed with a cap.

The oxygen-absorbing multilayer laminate may be produced by any known method without specific limitation. The oxygen-absorbing medical multilayer container can be produced by a variety of types of injection molding processes. The detailed description of general injection molding of a multilayer laminate is the same as that described in the first embodiment, and duplicated description is omitted.

[Article to be Stored]

The article to be stored (filling material) filled in the oxygen-absorbing prefilled syringe of the embodiment may be any drug, such as a drug solution, and the type thereof is not specifically limited. The article to be stored is an arbitrary natural product or a compound, for example, a vitamin supplements, such as vitamin A, vitamin B2, vitamin B12, vitamin C, vitamin D, vitamin E, or vitamin K; an alkaloid, such as atropine; a hormone, such as adrenalin or insulin; a saccharide, such as glucose or maltose; an antibiotic, such as ceftriaxone, cephalosporin, or cyclosporine; or a benzodiazepine-based drug, such as oxazolam, flunitrazepam, clotiazepam, or clobazam. When the oxygen-absorbing prefilled syringe of the embodiment is filled with such a natural product or a compound, the amount of the natural product or the compound adsorbing to the prefilled syringe is small, and deterioration due to oxidation of the product or compound can be suppressed and transpiration of the solvent (e.g., water) can be also suppressed.

Fifth Embodiment

[Method for Storing Biological Medicine]

The method for storing a biological medicine of the embodiment stores a biological medicine in an oxygen-absorbing medical multilayer container including an oxygen-absorbing layer containing an oxygen-absorbing composition and a resin layer containing a thermoplastic resin (b). The oxygen-absorbing composition contains at least one compound having a tetralin ring represented by Formula (1), a transition metal catalyst, and a thermoplastic resin (a).

In other words, this method for storing a biological medicine stores a biological medicine in an oxygen-absorbing medical multilayer container according to any one of the first to fourth embodiments.

The method for storing a biological medicine of the embodiment uses the oxygen-absorbing medical multilayer container as a storage container for a biological medicine. As a result, the storage container absorbs oxygen inside the container and also absorbs oxygen from outside of the container, if oxygen passes through or penetrates the wall of the container, even if the amount of the oxygen is small, and can thereby prevent the biological medicine (article to be stored) from, for example, being deteriorated by oxygen. This oxygen-absorbing medical multilayer container can absorb oxygen regardless of the presence or absence of water in the article to be stored and does not cause odor generation after oxygen absorption and can, therefore, be used for a variety of biological medicines. In addition, the oxygen-absorbing medical multilayer container causes a significantly small reduction in strength due to, for example, oxidation even after oxygen absorption and maintains the strength of the oxygen-absorbing layer even in use for a long period of time. Consequently, an oxygen-absorbing medical multilayer container substantially not causing interlayer peeling can also be achieved. Thus, the biological medicine can also be protected from, for example, a shock from outside for a long time. The method using such an oxygen-absorbing medical multilayer container is particularly useful for storage of biological medicines that are highly affected by oxygen.

The biological medicines that can be used in the embodiment are, for example, drugs generated by biotechnology, such as a cell culture technique or a gene recombination technique, and examples thereof may include protein medicinal products, nucleic acid medicinal products, and peptide medicinal products. More specifically, examples of the biological medicine may include, but are not limited to, various monoclonal antibodies, various vaccines, interferons, insulin, growth hormones, erythropoietin, colony stimulating factors, TPA, interleukins, blood coagulation factor VIII, blood coagulation factor IX, natriuretic hormones, somatomedin, glucagon, serum albumin, calcitonin, growth hormone-releasing factors, digestive enzyme agents, inflammatory enzyme agents, antibiotics, antisense nucleic acids, antigen nucleic acids, decoy nucleic acids, aptamers, siRNAs, and microRNAs, and biosimilars thereof. When such a biological medicine is filled in the oxygen-absorbing medical multilayer container, the amount of the biological medicine adsorbing to the medical container is small, and deterioration due to oxidation of the biological medicine and a reduction in drug efficacy can be suppressed and transpiration of the solvent (e.g., water) can be also suppressed.

The oxygen-absorbing medical multilayer container and/or the biological medicine to be stored therein are preferably sterilized before and after filling the oxygen-absorbing medical multilayer container with the biological medicine. The sterilization treatment can be performed by a method and conditions suitable for the biological medicine to be stored. Examples of the sterilizing method may include treatment with hot water of 100° C. or less, treatment with pressurized hot water of 100° C. or more, heat sterilization such as high temperature treatment at 121° C. or more, sterilization with electromagnetic waves such as UV rays, micro waves, or gamma rays, treatment with a gas such as ethylene oxide, and sterilization with a chemical agent such as hydrogen peroxide or hypochlorous acid.

[Oxygen-Absorbing Medical Multilayer Container]

The method for storing a biological medicine of the embodiment can use, for example, the oxygen-absorbing medical multilayer container of the first, second, third, or fourth embodiment. A mode of the oxygen-absorbing medical multilayer container used in the storing method of the embodiment will now be further described. The oxygen-absorbing medical multilayer container may have any layer structure, and the number and the types of the oxygen-absorbing layer (layer A) and the resin layer (layer B) are not specifically limited. For example, the oxygen-absorbing multilayer injection-molded product may be composed of one layer of layer A and one layer of layer B to form a structure of A/B or may be composed of one layer of layer A and two layers of layer B to form a three-layer structure of B/A/B. Alternatively, the multilayer injection-molded product may be composed of one layer of layer A, two layers of layer B1, and two layers of layer B2 to form a five-layer structure of B1/B2/A/B2/B1 or may be composed of one layer of layer A, layer B1, and layer B2 to form a three-layer structure of B1/A/B2 composed of two-material two-layer. The multilayer injection-molded product of the embodiment can optionally include an arbitrary layer, such as an adhesive layer (layer AD), to form, for example, a seven-layer structure of B1/AD/B2/A/B2/AD/B1.

[Oxygen-Absorbing Layer (Layer A)]

The oxygen-absorbing layer (layer A) is a layer containing an oxygen-absorbing composition that contains at least one compound having a tetralin ring represented by Formula (1) (hereinafter, also simply referred to as "tetralin compound"), a transition metal catalyst, and a thermoplastic resin (a).

<Compound Having a Tetralin Ring>

The compound having a tetralin ring described in the first embodiment can be appropriately used.

<Transition Metal Catalyst>

The transition metal catalyst described in the first embodiment can be appropriately used.

<Thermoplastic Resin (a)>

The thermoplastic resin (a) described in the first embodiment can be appropriately used.

[Resin Layer (Layer B)]

The resin layer (layer B) of the oxygen-absorbing medical multilayer container is a layer containing a thermoplastic resin. The content of the thermoplastic resin (b1 or b2) in layer B can be appropriately determined and is not specifically limited, and is preferably 70% to 100% by mass, more preferably 80% to 100% by mass, and most preferably 90% to 100% by mass, based on the total amount of layer B.

The oxygen-absorbing medical multilayer container may include a plurality of layers of layer B, and the plurality of layers of layer B may have the same or different structures. The thickness of layer B in the oxygen-absorbing medical multilayer container of the embodiment can be appropriately determined depending on the use and the desired performance. Although the thickness is not specifically limited, from the viewpoint of securing various physical properties, i.e., the strength, such as drop resistance, and flexibility, required in the multilayer laminate, the thickness is preferably 5 to 1000 µm, more preferably 10 to 800 µm, and most preferably 20 to 500 µm.

The thermoplastic resin (b1 or b2) of layer B of the oxygen-absorbing medical multilayer container can be an arbitrary thermoplastic resin and is not specifically limited. For example, the thermoplastic resin may be the same as or different from the thermoplastic resin (a) used in the above-described layer A. Layer B preferably contains at least one thermoplastic resin selected from the group consisting of polyolefins, polyesters, polyamides, ethylene-vinyl alcohol copolymers, plant-derived resins, and chlorine-containing resins. The content of the thermoplastic resin (b1 or b2) used in layer B is preferably 50% to 100% by mass, more preferably 70% to 100% by mass, and most preferably 90% to 100% by mass, based on the total amount of layer B.

The polyolefin, polyester, polyamide, ethylene-vinyl alcohol copolymer, plant-derived resin, and chlorine-containing resin exemplified as the thermoplastic resin (b1 or b2) that can be used in layer B can be those exemplified as the thermoplastic resins that can be used in layer A.

Layer B may contain a variety of additives known in the art, in addition to the above-mentioned thermoplastic resin (b1 or b2). Examples of such optional components may include, but are not limited to, desiccants, color pigments such as titanium oxide, dyes, antioxidants, slipping agents, antistatic agents, plasticizers, stabilizers, additives such as lubricants, fillers such as calcium carbonate, clay, mica, and silica, and deodorants. In particular, from the viewpoint of recycling and reprocessing offcuts generated during production, it is preferable to add an antioxidant to layer B.

[Other Layer]

The oxygen-absorbing medical multilayer container of the embodiment may further include an arbitrary layer, in addition to the above-described oxygen-absorbing layer (layer A) and the resin layer (layer B), depending on desired performance and other factors. Examples of such arbitrary layer may include adhesive layers, metal foil, metal vapor deposition layers, and organic-inorganic films.

For example, from the viewpoint of further increasing the interlayer adhesion strength between adjacent two layers, an adhesive layer (layer AD) is preferably disposed between the two layers. The adhesive layer preferably contains a thermoplastic resin having adhesiveness. Examples of the thermoplastic resin having adhesiveness may include acid-modified polyolefin resins obtained by modifying polyolefin-based resins, such as polyethylene and polypropylene, with unsaturated carboxylic acids, such as acrylic acid, methacrylic acid, maleic acid, maleic anhydride, fumaric acid, and itaconic acid; and polyester-based thermoplastic elastomers mainly composed of polyester-based block copolymers. In addition, from the viewpoint of enhancing the adhesiveness to the above-described resin layer (layer B), preferred is a resin prepared by modifying a resin of the same type as the thermoplastic resin used in layer B. The adhesive layer may have any thickness, but from the viewpoint of securing molding processability while maintaining practical adhesion strength, the thickness is preferably 2 to 100 µm, more preferably 5 to 90 µm, and most preferably 10 to 80 µm.

From the viewpoint of further enhancing the gas barrier property and light shielding property, one surface of the above-described layer A or layer B is preferably provided with, for example, metal foil, a metal vapor deposition layer, or an organic-inorganic film. Here, the metal foil is not specifically limited, and preferred is aluminum foil. The thickness of the metal foil is preferably 3 to 50 µm, more preferably 3 to 30 µm, and most preferably 5 to 15 µm, from the viewpoint of, for example, the gas barrier property, light shielding property, and bending resistance. The metal vapor deposition layer is not specifically limited, and preferred is, for example, a film of a metal, such as aluminum or alumina, or an oxide thereof deposited on a resin film. Examples of the method for forming the vapor deposition film may include, but are not limited to, physical vapor deposition, such as vacuum vapor deposition, sputtering, or ion plating; and chemical vapor deposition, such as PECVD, and a known method can be employed. The vapor deposition film preferably has a thickness of 5 to 500 nm and more preferably 5 to 200 nm, from the viewpoint of, for example, the gas barrier property, light shielding property, and bending resistance. The organic-inorganic film layer is not specifically limited, and is preferably, for example, a resin film coated with a silica-poly(vinyl alcohol) hybrid film prepared by a sol-gel method. The coating film preferably has a thickness of 100 nm to 50 µm and more preferably 1 to 15 µm, from the viewpoint of, for example, the gas barrier property, light shielding property, and bending resistance.

The thickness of the oxygen-absorbing medical multilayer container is not specifically limited and is preferably 500 to 5000 μm, more preferably 700 to 4000 μm, and most preferably 800 to 3000 μm, from the viewpoint of enhancing the oxygen-absorbing performance and securing various physical properties, such as flexibility, required in a storage container.

[Production Process and Other Items for Oxygen-Absorbing Medical Multilayer Container]

The oxygen-absorbing medical multilayer container can be produced by a known method depending on, for example, the properties of each material and the desired shapes, and the method is not specifically limited. For example, the oxygen-absorbing medical multilayer container can be produced by a variety of types of injection molding processes.

For example, an injection-molded product having a shape along the shape of the cavity of an injection mold can be produced with a molding apparatus equipped with an extruder and an injection mold by injecting the oxygen-absorbing composition into the cavity of the mold from the injection cylinder through a mold hot runner. On this occasion, the neck part of the resulting molded product may be crystallized by heat treatment for imparting heat resistance to the neck part. The degree of crystallinity in this case may be appropriately determined depending on the type of the resin used and desired performance and is not specifically limited. In general, the degree of crystallinity is preferably about 30% to 50%, more preferably 35% to 45%. The neck of the molded product may be crystallized after secondary processing, which will be described below.

The shape of the oxygen-absorbing medical multilayer container may be appropriately determined depending on the usage and is not specifically limited. In a case of injection molding using a mold as described above, an arbitrary shape along the shape of the cavity of the mold can be formed.

The oxygen-absorbing medical multilayer container used in a part of the components of a container for sealing absorbs oxygen inside the container and also absorbs oxygen from the outside of the container, if oxygen passes through or penetrates the wall of the container, even if the amount of the oxygen is small, and can thereby prevent the contents (article to be stored) from, for example, being deteriorated by oxygen. On this occasion, the injection-molded product of the embodiment itself may be molded into the shape of a container. Alternatively, the resulting injection-molded product can be fabricated into a container having a desired shape by secondary processing. The secondary processing can be, for example, blow molding.

The methods other than injection molding are the same as those described in the first embodiment, and duplicated description is omitted.

The mode of the oxygen-absorbing medical multilayer container used in the method for storing a biological medicine of the embodiment is not specifically limited, and the medical container can be used in various modes. Preferred examples of the usage may include, but are not limited to, vials, ampoules, prefilled syringes, and vacuum blood collection tubes. The details of the vials, ampoules, prefilled syringes, and vacuum blood collection tubes are the same as those described in the first embodiment unless specifically indicated otherwise, and duplicated description is omitted.

EXAMPLES

The present invention will now be more specifically described by Examples and Comparative Examples, but is not limited to the following Examples. Incidentally, the NMR measurement was performed at room temperature unless specifically indicated otherwise.

Synthesis Example 1: Diester Compound a Having a Tetralin Ring

A reactor equipped with a thermometer, a partial condenser, a total condenser, and a stirrer was charged with 248 g (1.0 mol) of dimethyl 1,2,3,4-tetrahydronaphthalene-2,6-dicarboxylate, 409 g (4.0 mol) of n-hexyl alcohol, and 0.34 g of tetrabutyl titanate and was heated to 150° C. in a nitrogen atmosphere, and the reaction was performed while removing the generated methanol to the outside of the reaction system to promote the reaction. After the completion of the generation of methanol, the reaction system was cooled to room temperature, and the unreacted n-hexyl alcohol was removed under reduced pressure to obtain diester compound A. The 3% weight-reduction temperature of the resulting compound was measured with a thermogravimetric/differential thermal analyzer (manufactured by Shimadzu Corporation, trade name "DTG-60"). The structural formula, molecular weight, and 3% weight-reduction temperature of the resulting compound are shown in Table 1. The results of NMR analysis were as follows. $^1$H-NMR (400 MHz CDCl$_3$) δ 7.73-7.79 (2H m), 7.16 (1H d), 4.29 (2H t), 4.10 (2H t), 3.01-3.08 (2H m), 2.82-2.97 (2H m), 2.70-2.78 (1H m), 2.18-2.24 (1H m), 1.84-1.94 (1H m), 1.71-1.79 (2H m), 1.58-1.68 (2H m), 1.25-1.48 (12H m), 0.90 (6H t).

Synthesis Example 2: Diester Compound B Having a Tetralin Ring

Diester compound B was prepared by the same procedure as that in Synthesis Example 1 except that 521 g (4.0 mol) of n-octyl alcohol was used instead of n-hexyl alcohol and that the reaction temperature was 190° C. The 3% weight-reduction temperature of the resulting compound was measured with a thermogravimetric/differential thermal analyzer (manufactured by Shimadzu Corporation, trade name "DTG-60"). The structural formula, molecular weight, and 3% weight-reduction temperature of the resulting compound are shown in Table 1. The results of NMR analysis were as follows. $^1$H-NMR (400 MHz CDCl$_3$) δ 7.68-7.74 (2H m), 7.10 (1H d), 4.23 (2H t), 4.04 (2H t), 2.92-3.00 (2H m), 2.72-2.89 (2H m), 2.63-2.70 (1H m), 2.10-2.18 (1H m), 1.76-1.85 (1H m), 1.63-1.72 (2H m), 1.50-1.59 (2H m), 1.09-1.40 (20H m), 0.90 (6H t).

Synthesis Example 3: Diester Compound C Having a Tetralin Ring

Diester compound C was prepared by the same procedure as that in Synthesis Example 2 except that dimethyl 1,2,3,4-tetrahydronaphthalene-1,8-dicarboxylate was used instead of dimethyl 1,2,3,4-tetrahydronaphthalene-2,6-dicarboxylate. The 3% weight-reduction temperature of the resulting compound was measured with a thermogravimetric/differential thermal analyzer (manufactured by Shimadzu Corporation, trade name "DTG-60"). The structural formula, molecular weight, and 3% weight-reduction temperature of the resulting compound are shown in Table 1. The results of NMR analysis were as follows. $^1$H-NMR (400 MHz CDCl$_3$) δ 7.78 (1H d), 7.17-7.29 (2H m), 4.50 (1H t), 4.22 (2H t), 3.98-4.12 (2H m), 2.76-2.93 (2H m), 2.21-2.30 (1H m), 1.89-1.99 (1H m), 1.67-1.83 (4H m), 1.50-1.63 (3H m), 1.18-1.44 (19H m), 0.89 (6H t).

Synthesis Example 4: Diester Compound D Having a Tetralin Ring

A reactor equipped with a thermometer, a partial condenser, a total condenser, and a stirrer was charged with 108 g (0.62 mmol) of dimethyl adipate and 300 g (1.85 mmol) of 6-hydroxymethyl-1,2,3,4-tetrahydronaphthalene and was heated to 130° C. To the mixture added was 0.58 g of titanium tetrabutoxide. The temperature was raised to 200° C., and the reaction was performed while removing the generated methanol to the outside of the reaction system to promote the reaction. After the completion of the generation of methanol, the reaction system was cooled to room temperature. The unreacted 6-hydroxymethyl-1,2,3,4-tetrahydronaphthalene was removed under reduced pressure, and diester compound D was obtained by recrystallization. The 3% weight-reduction temperature of the resulting compound was measured with a thermogravimetric/differential thermal analyzer (manufactured by Shimadzu Corporation, trade name "DTG-60"). The structural formula, molecular weight, and 3% weight-reduction temperature of the resulting compound are shown in Table 1. The results of NMR analysis were as follows. $^1$H-NMR (400 MHz CDCl$_3$) δ 7.00 (6H m), 5.02 (4H s), 2.70-2.79 (8H m), 2.34 (4H t), 1.74-1.83 (8H m), 1.64-1.70 (4H m).

Synthesis Example 5: Diamide Compound E Having a Tetralin Ring

A 2000-mL autoclave equipped with a thermometer and a stirrer was charged with 248 g (1.0 mol) of dimethyl 1,2,3,4-tetrahydronaphthalene-2,6-dicarboxylate and 607 g (6.0 mol) of n-hexylamine, was purged with nitrogen, was then heated to 220° C., and was stirred at this temperature for 5 hours. After cooling to room temperature, diamide compound E was obtained through filtration and recrystallization. The 3% weight-reduction temperature of the resulting compound was measured with a thermogravimetric/differential thermal analyzer (manufactured by Shimadzu Corporation, trade name "DTG-60") The structural formula, molecular weight, and 3% weight-reduction temperature of the resulting compound are shown in Table 1. The results of NMR analysis were as follows. $^1$H-NMR (400 MHz CDCl$_3$) δ 7.42 (1H s), 7.37 (1H d), 7.04 (1H d), 5.99 (1H m), 5.53 (1H m), 3.32-3.41 (2H m), 3.15-3.24 (2H m), 2.68-3.03 (4H m), 2.35-2.43 (1H m), 1.97-2.05 (1H m), 1.76-1.87 (1H m), 1.17-1.58 (12H m), 0.83 (6H t).

Synthesis Example 6: Acid Anhydride F Having a Tetralin Ring

An autoclave having an internal volume of 18 L was charged with 1.8 kg of 1,8-naphthalic anhydride, 300 g of a 5 wt % palladium on activated carbon catalyst (dried product), and 7.5 kg of ethyl acetate. The inside of the autoclave was purged with nitrogen of 1 MPa twice and then with hydrogen of 1 MPa twice at room temperature. Subsequently, the pressure was decreased to ordinary pressure, the internal temperature was increased to 80° C., the pressure was then increased to 5 MPa with hydrogen, and the mixture was stirred at 500 rpm for 2 hours at the same temperature and the same pressure. After the reaction, the autoclave was cooled to room temperature, and the hydrogen was released. After purge with nitrogen of 1 MPa twice, the catalyst was collected by filtration and was washed with 1.0 kg of acetone three times. The solvent in the resulting mother liquor was removed by an evaporator under reduced pressure to obtain a crude product. The resulting crude product was recrystallized to obtain acid anhydride F. The 3% weight-reduction temperature of the resulting compound was measured with a thermogravimetric/differential thermal analyzer (manufactured by Shimadzu Corporation, trade name "DTG-60"). The structural formula, molecular weight, and 3% weight-reduction temperature of the resulting compound are shown in Table 1. The results of NMR analysis were as follows. $^1$H-NMR (400 MHz CDCl$_3$) δ 7.98 (1H d), 7.47 (1H d), 7.38 (1H dd), 3.93 (1H t), 2.80-3.00 (2H m), 2.55-2.64 (1H m), 2.14-2.24 (1H m), 1.77-1.94 (2H m).

TABLE 1

| Compound having tetralin ring | Structure | Molecular weight | 3% weight-reduction temperature (° C.) |
|---|---|---|---|
| Diester compound A | (structure shown) | 388.6 | 237 |
| Diester compound B | (structure shown) | 444.7 | 262 |

TABLE 1-continued

| Compound having tetralin ring | Molecular weight | 3% weight-reduction temperature (° C.) |
|---|---|---|
| Diester compound C | 444.7 | 250 |
| Diester compound D | 434.6 | 263 |
| Diamide compound E | 386.6 | 290 |
| Acid anhydride F | 202.2 | 170 |

First Experiment

Example 1-1

95 parts by mass of an ethylene-vinyl alcohol copolymer (manufactured by Kuraray Co., Ltd., trade name: "EVAL L171B", hereinafter also abbreviated to "EVOH"), 5 parts by mass of diester compound A, and cobalt(II) stearate giving 0.05 parts by mass of cobalt were melt-kneaded with a twin-screw extruder having two 37-mm diameter screws at 220° C., extruded into a strand from the extruder head, cooled, and then pelletized to obtain an oxygen-absorbing composition (1). Subsequently, a vial as an oxygen-absorbing medical multilayer molded product was produced using this oxygen-absorbing composition (1) as shown below. The performance of the resulting vial was then evaluated as described below. Table 2 shows the evaluation results.

[Production of Vial]

Under the following conditions, an injection molded product having a three-layer structure of B/A/B was prepared by injecting a thermoplastic resin constituting the resin layer (layer B) from an injection cylinder, then injecting oxygen-absorbing composition (1) constituting the oxygen-absorbing layer (layer A) from another injection cylinder simultaneously with the thermoplastic resin constituting layer B, and then injecting a necessary amount of the thermoplastic resin constituting layer B to fill the cavity of the injection mold. The resulting injection-molded product was then cooled to a predetermined temperature, was transferred to a blow mold, and was blow molded to produce a vial (bottle portion). Here, the total mass of the vial was 24 g, and the mass of layer A was 30% by mass of the total mass of the vial. The thermoplastic resin constituting layer B used was polypropylene (manufactured by Japan Polypropylene Corporation, trade name: "MG03B").

(Shape of Vial)

The vial had a total length of 89 mm, an outer diameter of 40 mmφ, and a thickness of 1.8 mm. The vial was produced with an injection blow integral-molding apparatus (manufactured by UNILOY, model: IBS 85, providing four vials).

(Conditions for Molding the Vial)

Temperature of injection cylinder for layer A: 220° C.
Temperature of injection cylinder for layer B: 280° C.
Temperature of resin flow path in injection mold: 280° C.
Blow temperature: 150° C.
Temperature of cooling water for blow mold: 15° C.

[Evaluation of Vial Performance]

The resulting vial was evaluated through measurement of the oxygen transmission rate, verification of the appearance after molding, a drop test, and an elution test in accordance with the following methods and criteria.

(1) Oxygen Transmission Rate (OTR) of Vial

The oxygen transmission rate was measured on the 30th day from the start of the measurement in an atmosphere of a temperature of 23° C. and relative humidities of 50% (outside the molded product) and 100% (inside the molded product) with an oxygen transmission rate measurement apparatus (manufactured by MOCON, Inc., trade name: "OX-TRAN 2-21 ML"). A lower measurement value indicates a higher oxygen barrier property. The detection lower limit of the measurement is an oxygen transmission rate of $5 \times 10^{-5}$ mL/(0.21 atm·day·package).

(2) Appearance after Molding

The visibility of the contents in the vial was visually observed. A vial allowing confirmation of the volume and the color tone of the contents and not having any problems in visibility was defined as being acceptable.

(3) Drop Test

The vial was stored at 40° C. and 90% RH for one month, then filled with 50 mL of pure water, and then sealed with a rubber stopper and an aluminum cap. The thus-prepared sealed container was dropped from a height of 2 m and was then investigated for the appearance of the container. The drop test was performed for twenty sealed containers prepared as in above, and the appearance of the twenty containers was investigated.

(4) Elution Test

The vial was stored at 40° C. and 90% RH for one month, then filled with 50 mL of pure water, and then sealed with a rubber stopper and an aluminum cap. The thus-prepared sealed container was stored at 40° C. and 60% RH for four months, and the total amount of carbon (hereinafter, referred to as TOC) in the pure water was then measured.

(TOC Measurement)

Apparatus: TOC-VCPH manufactured by Shimadzu Corporation

Temperature of combustion furnace: 720° C.

Gas/flow rate: high purity air, 150 mL/min at TOC meter portion

Amount injected: 150 μL

Detection limit: 1 μg/mL

Example 1-2

A multilayer vial was produced as in Example 1 except that diester compound B was used instead of diester compound A, and was evaluated as in Example 1-1. The results are shown in Table 2.

Example 1-3

A multilayer vial was produced as in Example 1-1 except that diester compound C was used instead of diester compound A, and was evaluated as in Example 1-1. The results are shown in Table 2.

Example 1-4

A multilayer vial was produced as in Example 1-1 except that diester compound D was used instead of diester compound A, and was evaluated as in Example 1-1. The results are shown in Table 2.

Example 1-5

A multilayer vial was produced as in Example 1-1 except that diamide compound E was used instead of diester compound A, and was evaluated as in Example 1-1. The results are shown in Table 2.

Example 1-6

A multilayer vial was produced as in Example 1-1 except that acid anhydride F was used instead of diester compound A, and was evaluated as in Example 1-1. The results are shown in Table 2.

Example 1-7

A multilayer vial was produced as in Example 1-1 except that polycarbonate (manufactured by Saudi Basic Industries Corporation (SABIC), trade name "Lexan 144R") was used instead of polypropylene, that an amorphous polyamide (manufactured by Mitsubishi Engineering-Plastics Corporation, trade name: "NOVAMID X21-F07", hereinafter, also abbreviated to "6IT") was used instead of EVOH, and that the injection cylinder temperature for layer A was 260° C., and was evaluated as in Example 1-1. The results are shown in Table 2.

Example 1-8

A multilayer vial was produced as in Example 1-7 except that diester compound B was used instead of diester compound A, and was evaluated as in Example 1-1. The results are shown in Table 2.

Example 1-9

A multilayer vial was produced as in Example 1-7 except that diester compound C was used instead of diester compound A, and was evaluated as in Example 1-1. The results are shown in Table 2.

Example 1-10

A multilayer vial was produced as in Example 1-7 except that diester compound D was used instead of diester compound A, and was evaluated as in Example 1-1. The results are shown in Table 2.

Example 1-11

A multilayer vial was produced as in Example 1-7 except that diamide compound E was used instead of diester compound A, and was evaluated as in Example 1-1. The results are shown in Table 2.

Example 1-12

A multilayer vial was produced as in Example 1-7 except that acid anhydride F was used instead of diester compound A, and was evaluated as in Example 1-1. The results are shown in Table 2.

Comparative Example 1-1

A monolayer vial having the same shape as that of the vial in Example 1-1 was produced as in Example 1-1 except that 100 parts by mass of polypropylene (manufactured by Japan Polypropylene Corporation, trade name: "MG03B") was used as the resin constituting the layer. The performance of the resulting vial was evaluated as in Example 1-1. The evaluation results are shown in Table 2.

Comparative Example 1-2

A monolayer vial having the same shape as that of the vial in Example 1-1 was produced as in Example 1-1 except that 100 parts by mass of polycarbonate (manufactured by Saudi Basic Industries Corporation (SABIC), trade name "Lexan 144R") was used instead of polypropylene as the resin constituting the layer. The performance of the resulting vial was evaluated as in Example 1-1. The evaluation results are shown in Table 2.

Comparative Example 1-3

A multilayer vial was produced as in Example 1-1 except that diester compound A and cobalt stearate were not used, and was evaluated as in Example 1-1. That is, although the multilayer vial had a three-layer structure, the compound having a tetralin ring and the transition metal were not used (see Table 2). The results are shown in Table 2.

Comparative Example 1-4

A multilayer vial was produced as in Example 1-7 except that diester compound A and cobalt stearate were not used, and was evaluated as in Example 1-1. That is, although the multilayer vial had a three-layer structure, the compound having a tetralin ring and the transition metal were not used (see Table 2). The results are shown in Table 2.

Comparative Example 1-5

A mixture prepared by dry blending of 100 parts by mass of nylon MXD6 (manufactured by Mitsubishi Gas Chemical Company Inc., trade name: "S7007") and cobalt(II) stearate giving 0.04 parts by mass of cobalt was supplied to a twin-screw extruder having two 37-mm diameter screws at a rate of 15 kg/h, melt-kneaded at a cylinder temperature of 280° C., extruded into a strand from the extruder head, cooled, and then pelletized to obtain an oxygen-absorbing composition (M). A vial was produced as in Example 1-1 except that this oxygen-absorbing composition (M) was used instead of oxygen-absorbing composition (1). The performance of the resulting vial was evaluated as in Example 1-1. The evaluation results are shown in Table 2.

TABLE 2

| | Layer structure | Inner and outer layer resin | Composition of oxygen-absorbing layer (parts by mass) | | Transition metal |
|---|---|---|---|---|---|
| | | | Thermoplastic resin | Compound having tetralin ring | |
| Example 1-1 | Three-layer | PP | (95) EVOH | (5) Diester compound A | 0.05 (Co) |
| Example 1-2 | Three-layer | PP | (95) EVOH | (5) Diester compound B | 0.05 (Co) |
| Example 1-3 | Three-layer | PP | (95) EVOH | (5) Diester compound C | 0.05 (Co) |
| Example 1-4 | Three-layer | PP | (95) EVOH | (5) Diester compound D | 0.05 (Co) |
| Example 1-5 | Three-layer | PP | (95) EVOH | (5) Diamide compound E | 0.05 (Co) |
| Example 1-6 | Three-layer | PP | (95) EVOH | (5) Acid anhydride F | 0.05 (Co) |
| Example 1-7 | Three-layer | PC | (95) 6IT | (5) Diester compound A | 0.05 (Co) |
| Example 1-8 | Three-layer | PC | (95) 6IT | (5) Diester compound B | 0.05 (Co) |
| Example 1-9 | Three-layer | PC | (95) 6IT | (5) Diester compound C | 0.05 (Co) |
| Example 1-10 | Three-layer | PC | (95) 6IT | (5) Diester compound D | 0.05 (Co) |
| Example 1-11 | Three-layer | PC | (95) 6IT | (5) Diamide compound E | 0.05 (Co) |
| Example 1-12 | Three-layer | PC | (95) 6IT | (5) Acid anhydride F | 0.05 (Co) |
| Comparative Example 1-1 | Monolayer | PP | (100) PP | — | — |
| Comparative Example 1-2 | Monolayer | PC | (100) PC | — | — |
| Comparative Example 1-3 | Three-layer | PP | (100) EVOH | — | — |
| Comparative Example 1-4 | Three-layer | PC | (100) 6IT | — | — |
| Comparative Example 1-5 | Three-layer | PP | (100) Ny-MXD6 | — | 0.04 (Co) |

| | Oxygen transmission rate[1] (30th day) (cc/bottle/day/0.21 atm) | Appearance after molding | Drop test | Elution test TOC[2] (μg/mL) |
|---|---|---|---|---|
| Example 1-1 | Undetectable | Transparent (acceptable) | No breakage occurred in all containers | Undetectable |
| Example 1-2 | Undetectable | Transparent (acceptable) | No breakage occurred in all containers | Undetectable |
| Example 1-3 | Undetectable | Transparent (acceptable) | No breakage occurred in all containers | Undetectable |
| Example 1-4 | Undetectable | Transparent (acceptable) | No breakage occurred in all containers | Undetectable |

TABLE 2-continued

| | | | | |
|---|---|---|---|---|
| Example 1-5 | Undetectable | Transparent (acceptable) | No breakage occurred in all containers | Undetectable |
| Example 1-6 | Undetectable | Transparent (acceptable) | No breakage occurred in all containers | Undetectable |
| Example 1-7 | Undetectable | Having haze (acceptable) | No breakage occurred in all containers | Undetectable |
| Example 1-8 | Undetectable | Having haze (acceptable) | No breakage occurred in all containers | Undetectable |
| Example 1-9 | Undetectable | Having haze (acceptable) | No breakage occurred in all containers | Undetectable |
| Example 1-10 | Undetectable | Having haze (acceptable) | No breakage occurred in all containers | Undetectable |
| Example 1-11 | Undetectable | Transparent (acceptable) | No breakage occurred in all containers | Undetectable |
| Example 1-12 | Undetectable | Transparent (acceptable) | No breakage occurred in all containers | Undetectable |
| Comparative Example 1-1 | 0.0999 | Having haze (acceptable) | No breakage occurred in all containers | Undetectable |
| Comparative Example 1-2 | 0.212 | Transparent (acceptable) | No breakage occurred in all containers | Undetectable |
| Comparative Example 1-3 | 0.002 | Having haze (acceptable) | No breakage occurred in all containers | Undetectable |
| Comparative Example 1-4 | 0.0017 | Transparent (acceptable) | No breakage occurred in all containers | Undetectable |
| Comparative Example 1-5 | Undetectable | Having haze (acceptable) | Breakage occurred in 14 of 20 | 15 |

1) Unit: mL/(0.21 atm·day·package), Detection lower limit: $5 \times 10^{-5}$ mL/(0.21 atm·day·package)
2) Detection lower limit: (0.1 μg/mL)

As obvious from Table 2, it was observed that the vial of each Example had a reduced oxygen transmission rate and a satisfactory oxygen barrier property, maintained a satisfactory strength even after long-term storage, secured the visibility of contents, and showed a reduced amount of elution from the container into the contents, compared to the vial of each Comparative Example.

Second Experiment

Diester compounds A to D each having a tetralin ring produced in Synthesis Examples 1 to 4, and diamide compound E having a tetralin ring produced in Synthesis Example 5, and acid anhydride F having a tetralin ring produced in Synthesis Example 6 were used.

Example 2-1

95 parts by mass of an ethylene-vinyl alcohol copolymer (manufactured by Kuraray Co., Ltd., trade name: "EVAL L171B", hereinafter also abbreviated to "EVOH"), 5 parts by mass of diester compound A, and cobalt(II) stearate giving 0.05 parts by mass of cobalt were melt-kneaded with a twin-screw extruder having two 37-mm diameter screws at 220° C., extruded into a strand from the extruder head, cooled, and then pelletized to obtain an oxygen-absorbing composition (1). Subsequently, a vial as an oxygen-absorbing medical multilayer molded product was produced using this oxygen-absorbing composition (1) as shown below. The performance of the resulting vial was then evaluated as described below. Table 3 shows the evaluation results.
[Production of Vial]

Under the following conditions, an injection molded product having a three-layer structure of B/A/B was prepared by injecting polyolefin constituting the resin layer (layer B) containing the polyolefin from an injection cylinder, then injecting oxygen-absorbing composition (1) constituting the oxygen-absorbing layer (layer A) from another injection cylinder simultaneously with the polyolefin constituting layer B, and then injecting a necessary amount of the polyolefin constituting layer B to fill the cavity of the injection mold. The resulting injection-molded product was then cooled to a predetermined temperature, was transferred to a blow mold, and was blow molded to produce a vial (bottle portion). Here, the total mass of the vial was 24 g, and the mass of layer A was 30% by mass of the total mass of the vial. The polyolefin constituting layer B used was a cylcoolefin polymer (manufactured by Zeon Corporation, trade name: "ZEONEX 690R", hereinafter also abbreviated to "COP").
(Shape of Vial)

The vial had a total length of 89 mm, an outer diameter of 40 mmφ, and a thickness of 1.8 mm. The vial was produced with an injection blow integral-molding apparatus (manufactured by UNILOY, model: IBS 85, providing four vials).
(Conditions for Molding the Vial)

Temperature of injection cylinder for layer A: 220° C.
Temperature of injection cylinder for layer B: 280° C.
Temperature of resin flow path in injection mold: 280° C.
Blow temperature: 150° C.
Temperature of cooling water for blow mold: 15° C.
[Evaluation of Vial Performance]

The resulting vial was evaluated through measurement of the oxygen transmission rate, verification of the appearance after molding, a drop test, and an elution test in accordance with the following methods and criteria.
(1) Oxygen Transmission Rate (OTR) of Vial The oxygen transmission rate was measured on the 30th day from the start of the measurement in an atmosphere of a temperature of 23° C. and relative humidities of 50% (outside the molded product) and 100% (inside the molded product) with an oxygen transmission rate measurement apparatus (manufactured by MOCON, Inc., trade name: OX-TRAN 2-21 ML). A lower measurement value indicates a higher oxygen barrier property. The detection lower limit of the measurement is an oxygen transmission rate of $5 \times 10^{-5}$ mL/(0.21 atm·day·package).
(2) Water Vapor Transmission Rate (WVTR) of Vial The water vapor transmission rate was measured on the tenth day from the start of the measurement in an atmosphere of a temperature of 40° C. and a relative humidity of 100% (outside the molded product) with a water vapor transmission rate measurement apparatus (manufactured by MOCON, Inc., trade name: "PERMATRAN-W 3/33G"). A lower measurement value indicates a higher water vapor barrier property. The detection lower limit is a water vapor transmission rate of $5 \times 10^{-4}$ g/(day·package).

(3) Appearance after Molding

The visibility of the contents in the vial was visually observed. A vial allowing confirmation of the volume and the color tone of the contents and not having any problems in visibility was defined as being acceptable.

(4) Drop Test

The vial was stored at 40° C. and 90% RH for one month, then filled with 50 mL of pure water, and then sealed with a rubber stopper and an aluminum cap. The thus-prepared sealed container was dropped from a height of 2 m and was then investigated for the appearance of the container. The drop test was performed for twenty sealed containers prepared as in above, and the appearance of the twenty containers was investigated.

(5) Elution Test

The vial was stored at 40° C. and 90% RH for one month, then filled with 50 mL of pure water, and then sealed with a rubber stopper and an aluminum cap. The thus-prepared sealed container was stored at 40° C. and 60% RH for four months, and the total amount of carbon (hereinafter, referred to as TOC) in the pure water was then measured.

(TOC Measurement)

Apparatus: TOC-VCPH manufactured by Shimadzu Corporation

Temperature of combustion furnace: 720° C.

Gas/flow rate: high purity air, 150 mL/min at TOC meter portion

Amount injected: 150 μL

Detection limit: 1 μg/mL

Example 2-2

A multilayer vial was produced as in Example 2-1 except that diester compound B was used instead of diester compound A, and was evaluated as in Example 2-1. The results are shown in Table 3.

Example 2-3

A multilayer vial was produced as in Example 2-1 except that diester compound C was used instead of diester compound A, and was evaluated as in Example 2-1. The results are shown in Table 3.

Example 2-4

A multilayer vial was produced as in Example 2-1 except that diester compound D was used instead of diester compound A, and was evaluated as in Example 2-1. The results are shown in Table 3.

Example 2-5

A multilayer vial was produced as in Example 2-1 except that diamide compound E was used instead of diester compound A, and was evaluated as in Example 2-1. The results are shown in Table 3.

Example 2-6

A multilayer vial was produced as in Example 2-1 except that acid anhydride F was used instead of diester compound A, and was evaluated as in Example 2-1. The results are shown in Table 3.

Example 2-7

A multilayer vial was produced as in Example 2-1 except that an amorphous polyamide (manufactured by Mitsubishi Engineering-Plastics Corporation, trade name: "NOVAMID X21-F07", hereinafter, also abbreviated to "6IT") was used instead of EVOH and that the injection cylinder temperature for layer A was 260° C., and was evaluated as in Example 2-1. The results are shown in Table 3.

Example 2-8

A multilayer vial was produced as in Example 2-7 except that diester compound B was used instead of diester compound A, and was evaluated as in Example 2-1. The results are shown in Table 3.

Example 2-9

A multilayer vial was produced as in Example 2-7 except that diester compound C was used instead of diester compound A, and was evaluated as in Example 2-1. The results are shown in Table 3.

Example 2-10

A multilayer vial was produced as in Example 2-7 except that diester compound D was used instead of diester compound A, and was evaluated as in Example 2-1. The results are shown in Table 3.

Example 2-11

A multilayer vial was produced as in Example 2-7 except that diamide compound E was used instead of diester compound A, and was evaluated as in Example 2-1. The results are shown in Table 3.

Example 2-12

A multilayer vial was produced as in Example 2-7 except that acid anhydride F was used instead of diester compound A, and was evaluated as in Example 2-1. The results are shown in Table 3.

Comparative Example 2-1

A monolayer vial having the same shape as that of the vial in Example 2-1 was produced as in Example 2-1 except that 100 parts by mass of a cylcoolefin polymer (manufactured by Zeon Corporation, trade name: "ZEONEX 690R") was used as the resin constituting the layer. The performance of the resulting vial was evaluated as in Example 2-1. The evaluation results are shown in Table 3.

Example 2-13

A monolayer vial having the same shape as that of the vial in Example 2-1 was produced as in Example 2-1 except that 100 parts by mass of polycarbonate (manufactured by Saudi Basic Industries Corporation (SABIC), trade name "Lexan 144R") was used as the resin constituting the layer. The performance of the resulting vial was evaluated as in Example 2-1. The evaluation results are shown in Table 3.

Comparative Example 2-2

A multilayer vial was produced as in Example 2-1 except that diester compound A and cobalt stearate were not used, and was evaluated as in Example 2-1. The results are shown in Table 3.

Comparative Example 2-3

A multilayer vial was produced as in Example 2-7 except that diester compound A and cobalt stearate were not used, and was evaluated as in Example 2-1. The results are shown in Table 3.

Comparative Example 2-4

A mixture prepared by dry blending of 100 parts by mass of nylon MXD6 (manufactured by Mitsubishi Gas Chemical Company Inc., trade name: "S7007") and cobalt(II) stearate giving 0.04 parts by mass of cobalt was supplied to a twin-screw extruder having two 37-mm diameter screws at a rate of 15 kg/h, melt-kneaded at a cylinder temperature of 280° C., extruded into a strand from the extruder head, cooled, and then pelletized to obtain an oxygen-absorbing composition (M). A vial was produced as in Example 2-1 except that this oxygen-absorbing composition (M) was used instead of oxygen-absorbing composition (1). The performance of the resulting vial was evaluated as in Example 2-1. The evaluation results are shown in Table 3.

TABLE 3

| | Resin constituting layer B | Composition of resin constituting layer A (parts by mass) | | Transition metal | Oxygen transmission rate[1] (30th day) |
|---|---|---|---|---|---|
| | | Thermoplastic resin | Compound having tetralin ring | | |
| Example 2-1 | COP | (95) EVOH | (5) Diester compound A | 0.05 (Co) | Undetectable |
| Example 2-2 | COP | (95) EVOH | (5) Diester compound B | 0.05 (Co) | Undetectable |
| Example 2-3 | COP | (95) EVOH | (5) Diester compound C | 0.05 (Co) | Undetectable |
| Example 2-4 | COP | (95) EVOH | (5) Diester compound D | 0.05 (Co) | Undetectable |
| Example 2-5 | COP | (95) EVOH | (5) Diamide compound E | 0.05 (Co) | Undetectable |
| Example 2-6 | COP | (95) EVOH | (5) Acid anhydride F | 0.05 (Co) | Undetectable |
| Example 2-7 | COP | (95) 6IT | (5) Diester compound A | 0.05 (Co) | Undetectable |
| Example 2-8 | COP | (95) 6IT | (5) Diester compound B | 0.05 (Co) | Undetectable |
| Example 2-9 | COP | (95) 6IT | (5) Diester compound C | 0.05 (Co) | Undetectable |
| Example 2-10 | COP | (95) 6IT | (5) Diester compound D | 0.05 (Co) | Undetectable |
| Example 2-11 | COP | (95) 6IT | (5) Diamide compound E | 0.05 (Co) | Undetectable |
| Example 2-12 | COP | (95) 6IT | (5) Acid anhydride F | 0.05 (Co) | Undetectable |
| Comparative Example 2-1 | | COP monolayer | | | 0.0382 |
| Example 2-13 | PC | (95) EVOH | (5) Diester compound A | 0.05 (Co) | Undetectable |
| Comparative Example 2-2 | COP | (100) EVOH | — | — | 0.0001 |
| Comparative Example 2-3 | COP | (100) 6IT | — | — | 0.0007 |
| Comparative Example 2-4 | COP | (100) Ny-MXD6 | — | 0.04 (Co) | Undetectable |

| | Water vapor transmission rate[2] (10th day) | Visibility of contents | Drop test | Elution test TOC[3] (μg/mL) |
|---|---|---|---|---|
| Example 2-1 | 0.0008 | Good | No breakage occurred in all containers | Undetectable |
| Example 2-2 | 0.0009 | Good | No breakage occurred in all containers | Undetectable |
| Example 2-3 | 0.0009 | Good | No breakage occurred in all containers | Undetectable |
| Example 2-4 | 0.0008 | Good | No breakage occurred in all containers | Undetectable |
| Example 2-5 | 0.0009 | Good | No breakage occurred in all containers | Undetectable |
| Example 2-6 | 0.0008 | Good | No breakage occurred in all containers | Undetectable |
| Example 2-7 | 0.0009 | Almost good | No breakage occurred in all containers | Undetectable |

TABLE 3-continued

|  | | | | |
|---|---|---|---|---|
| Example 2-8 | 0.0008 | Almost good | No breakage occurred in all containers | Undetectable |
| Example 2-9 | 0.0009 | Almost good | No breakage occurred in all containers | Undetectable |
| Example 2-10 | 0.0008 | Almost good | No breakage occurred in all containers | Undetectable |
| Example 2-11 | 0.0008 | Good | No breakage occurred in all containers | Undetectable |
| Example 2-12 | 0.0008 | Good | No breakage occurred in all containers | Undetectable |
| Comparative Example 2-1 | 0.0007 | Good | No breakage occurred in all containers | Undetectable |
| Example 2-13 | 0.0198 | Good | No breakage occurred in all containers | Undetectable |
| Comparative Example 2-2 | 0.0009 | Good | No breakage occurred in all containers | Undetectable |
| Comparative Example 2-3 | 0.0008 | Good | No breakage occurred in all containers | Undetectable |
| Comparative Example 2-4 | 0.0009 | Good | Breakage occurred in 14 of 20 | 15 |

1) Unit: mL/(0.21 atm·day·package), Detection lower limit: $5 \times 10^{-5}$ mL/(0.21 atm·day·package)
2) Unit: g/(day·package), Detection lower limit: $5 \times 10^{-4}$ g/(day·package)
3) Detection lower limit: (0.1 μg/mL)

As obvious from Table 3, it was observed that the vial of each Example had satisfactory oxygen barrier property and water vapor barrier property, maintained a satisfactory strength even after long-term storage, secured the visibility of the contents, and showed a reduced amount of elution from the container into the contents. In particular, in Examples 2-1 to 2-6, 2-11, and 2-12, the visibility of the contents was observed to be more satisfactory.

Third Experiment

Diester compounds A to D each having a tetralin ring produced in Synthesis Examples 1 to 4, and diamide compound E having a tetralin ring produced in Synthesis Example 5, and acid anhydride F having a tetralin ring produced in Synthesis Example 6 were used.

Example 3-1

95 parts by mass of an ethylene-vinyl alcohol copolymer (product name: "EVAL L171B", hereinafter also abbreviated to "EVOH", manufactured by Kuraray Co., Ltd.), 5 parts by mass of diester compound A, and cobalt(II) stearate giving 0.05 parts by mass of cobalt were melt-kneaded with a twin-screw extruder having two 37-mm diameter screws at 220° C., extruded into a strand from the extruder head, cooled, and then pelletized to obtain an oxygen-absorbing composition (1). Subsequently, a vial as an oxygen-absorbing medical multilayer molded product was produced using this oxygen-absorbing composition (1) as shown below. The performance of the resulting vial was then evaluated as described below. Table 4 shows the evaluation results.

[Production of Vial]

Under the following conditions, an injection molded product having a three-layer structure of B/A/B was prepared by injecting polyester constituting the resin layer (layer B) containing the polyester from an injection cylinder, then injecting oxygen-absorbing composition (1) constituting the oxygen-absorbing layer (layer A) from another injection cylinder simultaneously with the polyester constituting layer B, and then injecting a necessary amount of the polyester constituting layer B to fill the cavity of the injection mold. The resulting injection-molded product was then cooled to a predetermined temperature, was transferred to a blow mold, and was blow molded to produce a vial (bottle portion). Here, the total mass of the vial was 24 g, and the mass of layer A was 30% by mass of the total mass of the vial. The polyester constituting layer B used was a poly(ethylene terephthalate) resin (manufactured by Nippon Unipet Co., Ltd., trade name: "RT-553C", hereinafter also abbreviated to "PET").

(Shape of Vial)

The vial had a total length of 89 mm, an outer diameter of 40 mmφ, and a thickness of 1.8 mm. The vial was produced with an injection blow integral-molding apparatus (manufactured by UNILOY, model: IBS 85, providing four vials).

(Conditions for Molding the Vial)

Temperature of injection cylinder for layer A: 220° C.
Temperature of injection cylinder for layer B: 280° C.
Temperature of resin flow path in injection mold: 280° C.
Blow temperature: 150° C.
Temperature of cooling water for blow mold: 15° C.

[Evaluation of Vial Performance]

The resulting vial was evaluated through measurement of the oxygen transmission rate, verification of the appearance after molding, a drop test, and an elution test in accordance with the following methods and criteria.

(1) Oxygen Transmission Rate (OTR) of Vial

The oxygen transmission rate was measured on the 30th day from the start of the measurement in an atmosphere of a temperature of 23° C. and relative humidities of 50% (outside the molded product) and 100% (inside the molded product) with an oxygen transmission rate measurement apparatus (manufactured by MOCON, Inc., trade name: OX-TRAN 2-21 ML). A lower measurement value indicates a higher oxygen barrier property. The detection lower limit of the measurement is an oxygen transmission rate of $5 \times 10-5$ mL/(0.21 atm·day·package).

(2) Appearance after Molding

The visibility of the contents in the vial was visually observed. A vial not having any problems in visibility was defined as being acceptable.

(3) Drop Test

The vial was stored at 40° C. and 90% RH for one month, then filled with 50 mL of pure water, and then sealed with a rubber stopper and an aluminum cap. The thus-prepared sealed container was dropped from a height of 2 m and was then investigated for the appearance of the container. The drop test was performed for twenty containers under the same conditions.

(4) Elution Test

The vial was stored at 40° C. and 90% RH for one month, then filled with 50 mL of pure water, and then sealed with a rubber stopper and an aluminum cap. The thus-prepared sealed container was stored at 40° C. and 60% RH for four months, and the total amount of carbon (hereinafter, referred to as TOC) in the pure water was then measured.

(TOC Measurement)

Apparatus: TOC-VCPH manufactured by Shimadzu Corporation

Temperature of combustion furnace: 720° C.

Gas/flow rate: high purity air, 150 mL/min at TOC meter portion

Amount injected: 150 μL

Detection limit: 1 μg/mL

Example 3-2

A multilayer vial was produced as in Example 3-1 except that diester compound B was used instead of diester compound A, and was evaluated as in Example 3-1. The results are shown in Table 4.

Example 3-3

A multilayer vial was produced as in Example 3-1 except that diester compound C was used instead of diester compound A, and was evaluated as in Example 3-1. The results are shown in Table 4.

Example 3-4

A multilayer vial was produced as in Example 3-1 except that diester compound D was used instead of diester compound A, and was evaluated as in Example 3-1. The results are shown in Table 4.

Example 3-5

A multilayer vial was produced as in Example 3-1 except that diamide compound E was used instead of diester compound A, and was evaluated as in Example 3-1. The results are shown in Table 4.

Example 3-6

A multilayer vial was produced as in Example 3-1 except that acid anhydride F was used instead of diester compound A, and was evaluated as in Example 3-1. The results are shown in Table 4.

Example 3-7

A multilayer vial was produced as in Example 3-1 except that an amorphous polyamide (manufactured by Mitsubishi Engineering-Plastics Corporation, trade name: "NOVAMID X21-F07", hereinafter, also abbreviated to "6IT") was used instead of EVOH and that the injection cylinder temperature for layer A was 260° C., and was evaluated as in Example 3-1. The results are shown in Table 4.

Example 3-8

A multilayer vial was produced as in Example 3-7 except that diester compound B was used instead of diester compound A, and was evaluated as in Example 3-1. The results are shown in Table 4.

Example 3-9

A multilayer vial was produced as in Example 3-7 except that diester compound C was used instead of diester compound A, and was evaluated as in Example 3-1. The results are shown in Table 4.

Example 3-10

A multilayer vial was produced as in Example 3-7 except that diester compound D was used instead of diester compound A, and was evaluated as in Example 3-1. The results are shown in Table 4.

Example 3-11

A multilayer vial was produced as in Example 3-7 except that diamide compound E was used instead of diester compound A, and was evaluated as in Example 3-1. The results are shown in Table 4.

Example 3-12

A multilayer vial was produced as in Example 3-7 except that acid anhydride F was used instead of diester compound A, and was evaluated as in Example 3-1. The results are shown in Table 4.

Comparative Example 3-1

A multilayer vial was produced as in Example 3-1 except that diester compound A and cobalt stearate were not used, and was evaluated as in Example 3-1. The results are shown in Table 4.

Comparative Example 3-2

A multilayer vial was produced as in Example 3-7 except that diester compound A and cobalt stearate were not used, and was evaluated as in Example 3-1. The results are shown in Table 4.

Comparative Example 3-3

A mixture prepared by dry blending of 100 parts by mass of nylon MXD6 (manufactured by Mitsubishi Gas Chemical Company Inc., trade name: "S7007") and cobalt(II) stearate giving 0.04 parts by mass of cobalt was supplied to a twin-screw extruder having two 37-mm diameter screws at a rate of 15 kg/h, melt-kneaded at a cylinder temperature of 280° C., extruded into a strand from the extruder head, cooled, and then pelletized to obtain an oxygen-absorbing composition (M). A vial was produced as in Example 3-1 except that this oxygen-absorbing composition (M) was used instead of oxygen-absorbing composition (1) and that the injection cylinder temperature for layer B was 260° C.

The performance of the resulting vial was evaluated as in Example 3-1. The evaluation results are shown in Table 4.

TABLE 4

| | Resin constituting layer B | Composition of resin constituting layer A (parts by mass) | | | Oxygen transmission rate[1] (30th day) | Visibility of contents | Drop test | Elution test TOC[2] (μg/mL) |
|---|---|---|---|---|---|---|---|---|
| | | Thermoplastic resin | Compound having tetralin ring | Transition metal | | | | |
| Example 3-1 | PET | (95) EVOH | (5) Diester compound A | 0.05 (Co) | Undetectable | Transparent (acceptable) | No breakage occurred in all containers | Undetectable |
| Example 3-2 | PET | (95) EVOH | (5) Diester compound B | 0.05 (Co) | Undetectable | Transparent (acceptable) | No breakage occurred in all containers | Undetectable |
| Example 3-3 | PET | (95) EVOH | (5) Diester compound C | 0.05 (Co) | Undetectable | Transparent (acceptable) | No breakage occurred in all containers | Undetectable |
| Example 3-4 | PET | (95) EVOH | (5) Diester compound D | 0.05 (Co) | Undetectable | Transparent (acceptable) | No breakage occurred in all containers | Undetectable |
| Example 3-5 | PET | (95) EVOH | (5) Diamide compound E | 0.05 (Co) | Undetectable | Transparent (acceptable) | No breakage occurred in all containers | Undetectable |
| Example 3-6 | PET | (95) EVOH | (5) Acid anhydride F | 0.05 (Co) | Undetectable | Transparent (acceptable) | No breakage occurred in all containers | Undetectable |
| Example 3-7 | PET | (95) 6IT | (5) Diester compound A | 0.05 (Co) | Undetectable | Having haze (acceptable) | No breakage occurred in all containers | Undetectable |
| Example 3-8 | PET | (95) 6IT | (5) Diester compound B | 0.05 (Co) | Undetectable | Having haze (acceptable) | No breakage occurred in all containers | Undetectable |
| Example 3-9 | PET | (95) 6IT | (5) Diester compound C | 0.05 (Co) | Undetectable | Having haze (acceptable) | No breakage occurred in all containers | Undetectable |
| Example 3-10 | PET | (95) 6IT | (5) Diester compound D | 0.05 (Co) | Undetectable | Having haze (acceptable) | No breakage occurred in all containers | Undetectable |
| Example 3-11 | PET | (95) 6IT | (5) Diamide compound E | 0.05 (Co) | Undetectable | Transparent (acceptable) | No breakage occurred in all containers | Undetectable |
| Example 3-12 | PET | (95) 6IT | (5) Acid anhydride F | 0.05 (Co) | Undetectable | Transparent (acceptable) | No breakage occurred in all containers | Undetectable |
| Comparative Example 3-1 | PET | (100) EVOH | — | — | 0.00008 | Transparent (acceptable) | No breakage occurred in all containers | Undetectable |
| Comparative Example 3-2 | PET | (100) 6IT | — | — | 0.00054 | Transparent (acceptable) | No breakage occurred in all containers | Undetectable |
| Comparative Example 3-3 | PET | (100) Ny-MXD6 | — | 0.04 (Co) | Undetectable | Transparent (acceptable) | Breakage occurred in 14 of 20 | 15 |

(1) Unit: mL/(0.21 atm·day·package), Detection lower limit: $5 \times 10^{-5}$ mL/(0.21 atm·day·package)
(2) Detection lower limit: (0.1 μg/mL)

As obvious from Table 4, it was observed that the vial of each Example had a reduced oxygen transmission rate, secured the visibility of the inside of the container, maintained a satisfactory strength even after long-term storage, and showed a reduced amount of elution from the container into the contents, compared to the vial of each Comparative Example. It was further observed that the vials of Examples 3-1 to 3-6, 3-11, and 3-12 had excellent transparency to have very good visibility of the contents.

Fourth Experiment

Diester compounds A to D having tetralin rings produced in Synthesis Examples 1 to 4, and diamide compound E having a tetralin ring produced in Synthesis Example 5, and acid anhydride F having a tetralin ring produced in Synthesis Example 6 were used.

Example 4-1

95 parts by mass of an ethylene-vinyl alcohol copolymer (manufactured by Kuraray Co., Ltd., trade name: "EVAL L171B", hereinafter also abbreviated to "EVOH"), 5 parts by mass of diester compound A, and cobalt(II) stearate giving 0.05 parts by mass of cobalt were melt-kneaded with a twin-screw extruder having two 37-mm diameter screws at 220° C., extruded into a strand from the extruder head, cooled, and then pelletized to obtain oxygen-absorbing composition (1). Subsequently, a syringe as an oxygen-absorbing medical multilayer molded product was produced using this oxygen-absorbing composition (1) as shown below. The performance of the resulting syringe was then evaluated as described below. Table 5 shows the evaluation results.

[Production of Syringe]

Under the following conditions, a syringe having a three-layer structure of B/A/B was produced by injecting a thermoplastic resin constituting the resin layer (layer B) from an injection cylinder, then injecting oxygen-absorbing composition (1) constituting the oxygen-absorbing layer (layer A) from another injection cylinder simultaneously with the thermoplastic resin constituting layer B, and then injecting a necessary amount of the thermoplastic resin constituting layer B to fill the cavity of the injection mold. Here, the total mass of the syringe was 1.95 g, and the mass of layer A was 30% by mass of the total mass of the syringe. The thermoplastic resin constituting layer B used was a cycloolefin copolymer (manufactured by Ticona GmbH, trade name: "TOPAS6013, hereinafter, also abbreviated to "COC").

(Shape of Syringe)

The inner capacity was set to be 1 cc (standard) conformable to ISO 11040-6. The syringe was produced with an injection molding apparatus (manufactured by Nissei ASB Machine Co., Ltd., model: ASB-12N/10).

(Molding Conditions for Syringe)
Temperature of injection cylinder for layer A: 220° C.
Temperature of injection cylinder for layer B: 280° C.
Temperature of resin flow path in injection mold: 280° C.
Temperature of mold: 18° C.

87

[Evaluation of Syringe Performance]

The resulting syringe was evaluated through measurement of the oxygen transmission rate, verification of the appearance after molding, a shock resistance test, and an elution test in accordance with the following methods and criteria.

(1) Oxygen Transmission Rate (OTR) of Syringe

The oxygen transmission rate was measured on the 30th day from the start of the measurement in an atmosphere of a temperature of 23° C. and relative humidities of 50% (outside the molded product) and 100% (inside the molded product) with an oxygen transmission rate measurement apparatus (manufactured by MOCON, Inc., trade name: OX-TRAN 2-21 ML). A lower measurement value indicates a higher oxygen barrier property. The detection lower limit of the measurement is an oxygen transmission rate of 5×10−5 mL/(0.21 atm·day·package).

(2) Visibility of Contents of Syringe

The visibility of the contents in the syringe was visually observed. A syringe not having any problems in visibility was defined as being acceptable.

(3) Shock Resistance Test

The syringe was stored at 40° C. and 90% RH for 30 days, and a metal ball of 50 g was then dropped onto the syringe body from a height of 2 m. Twenty samples were investigated whether or not any breakage was caused on this occasion. The drop test was performed for twenty containers under the same conditions.

(4) Elution Test

The syringe was stored at 40° C. and 90% RH for 30 days, filled with 1 cc of pure water, and then sealed with a plunger equipped with a top cap and a gasket. The thus-prepared syringe was stored at 40° C. and 60% RH for 120 days, and the total amount of carbon (hereinafter, referred to as TOC) in the pure water was then measured.

(TOC Measurement)

Apparatus: TOC-VCPH manufactured by Shimadzu Corporation

Temperature of combustion furnace: 720° C.

Gas/flow rate: high purity air, 150 mL/min at TOC meter portion

Amount injected: 150 μL

Detection limit: 1 μg/mL

Example 4-2

A multilayer syringe was produced as in Example 4-1 except that diester compound B was used instead of diester compound A, and was evaluated as in Example 4-1. The results are shown in Table 5.

Example 4-3

A multilayer syringe was produced as in Example 4-1 except that diester compound C was used instead of diester compound A, and was evaluated as in Example 4-1. The results are shown in Table 5.

Example 4-4

A multilayer syringe was produced as in Example 4-1 except that diester compound D was used instead of diester compound A, and was evaluated as in Example 4-1. The results are shown in Table 5.

88

Example 4-5

A multilayer syringe was produced as in Example 4-1 except that diamide compound E was used instead of diester compound A, and was evaluated as in Example 4-1. The results are shown in Table 5.

Example 4-6

A multilayer syringe was produced as in Example 4-1 except that acid anhydride F was used instead of diester compound A, and was evaluated as in Example 4-1. The results are shown in Table 5.

Example 4-7

A multilayer syringe was produced as in Example 4-1 except that an amorphous polyamide (manufactured by Mitsubishi Engineering-Plastics Corporation, trade name: "NOVAMID X21-F07", hereinafter, also abbreviated to "6IT") was used instead of EVOH and that the injection cylinder temperature for layer A was 260° C., and was evaluated as in Example 4-1. The results are shown in Table 5.

Example 4-8

A multilayer syringe was produced as in Example 4-7 except that diester compound B was used instead of diester compound A, and was evaluated as in Example 4-1. The results are shown in Table 5.

Example 4-9

A multilayer syringe was produced as in Example 4-7 except that diester compound C was used instead of diester compound A, and was evaluated as in Example 4-1. The results are shown in Table 5.

Example 4-10

A multilayer syringe was produced as in Example 4-7 except that diester compound D was used instead of diester compound A, and was evaluated as in Example 4-1. The results are shown in Table 5.

Example 4-11

A multilayer syringe was produced as in Example 4-7 except that diamide compound E was used instead of diester compound A, and was evaluated as in Example 4-1. The results are shown in Table 5.

Example 4-12

A multilayer syringe was produced as in Example 4-7 except that acid anhydride F was used instead of diester compound A, and was evaluated as in Example 4-1. The results are shown in Table 5.

Example 4-13

A multilayer syringe was produced as in Example 4-1 except that polypropylene (manufactured by Japan Polypropylene Corporation, trade name: "MG03B", hereinafter, also abbreviated to "PP") was used instead of COC and that the injection cylinder temperature for layer B was 220° C., and was evaluated as in Example 4-1. The results are shown in Table 5.

Example 4-14

A multilayer syringe was produced as in Example 4-13 except that diester compound B was used instead of diester compound A, and was evaluated as in Example 4-1. The results are shown in Table 5.

Example 4-15

A multilayer syringe was produced as in Example 4-13 except that diester compound C was used instead of diester compound A, and was evaluated as in Example 4-1. The results are shown in Table 5.

Example 4-16

A multilayer syringe was produced as in Example 4-13 except that diester compound D was used instead of diester compound A, and was evaluated as in Example 4-1. The results are shown in Table 5.

Example 4-17

A multilayer syringe was produced as in Example 4-13 except that diamide compound E was used instead of diester compound A, and was evaluated as in Example 4-1. The results are shown in Table 5.

Example 4-18

A multilayer syringe was produced as in Example 4-13 except that acid anhydride F was used instead of diester compound A, and was evaluated as in Example 4-1. The results are shown in Table 5.

Comparative Example 4-1

A monolayer syringe having the same shape as that of the syringe in Example 4-1 was produced as in Example 4-1 except that COC was used instead of oxygen-absorbing composition (1) and that the injection cylinder temperature for layer A was 280° C., and was evaluated as in Example 4-1. The results are shown in Table 5.

Comparative Example 4-2

A monolayer syringe having the same shape as that of the syringe in Example 4-1 was produced as in Example 4-13 except that PP was used instead of oxygen-absorbing composition (1), and was evaluated as in Example 4-1. The results are shown in Table 5.

Comparative Example 4-3

A multilayer syringe was produced as in Example 4-1 except that diester compound A and cobalt stearate were not used, and was evaluated as in Example 4-1. The results are shown in Table 5.

Comparative Example 4-4

A multilayer syringe was produced as in Example 4-7 except that diester compound A and cobalt stearate were not used, and was evaluated as in Example 4-1. The results are shown in Table 5.

Comparative Example 4-5

A mixture prepared by dry blending of 100 parts by mass of nylon MXD6 (manufactured by Mitsubishi Gas Chemical Company Inc., trade name: "S7007") and cobalt(II) stearate giving 0.04 parts by mass of cobalt was supplied to a twin-screw extruder having two 37-mm diameter screws at a rate of 15 kg/h, melt-kneaded at a cylinder temperature of 280° C., extruded into a strand from the extruder head, cooled, and then pelletized to obtain an oxygen-absorbing composition (M). A syringe was produced as in Example 4-1 except that this oxygen-absorbing composition (M) was used instead of oxygen-absorbing composition (1) and that the injection cylinder temperature for layer B was 260° C. The performance of the resulting syringe was evaluated as in Example 4-1. The evaluation results are shown in Table 5.

TABLE 5

| | | | Composition of resin constituting layer A (parts by mass) | | |
|---|---|---|---|---|---|
| | Layer structure | Resin constituting layer B | Thermoplastic resin | Compound having tetralin ring | Transition metal |
| Example 4-1 | Three-layer | COC | (95) EVOH | (5) Diester compound A | 0.05 (Co) |
| Example 4-2 | Three-layer | COC | (95) EVOH | (5) Diester compound B | 0.05 (Co) |
| Example 4-3 | Three-layer | COC | (95) EVOH | (5) Diester compound C | 0.05 (Co) |
| Example 4-4 | Three-layer | COC | (95) EVOH | (5) Diester compound D | 0.05 (Co) |
| Example 4-5 | Three-layer | COC | (95) EVOH | (5) Diamide compound E | 0.05 (Co) |
| Example 4-6 | Three-layer | COC | (95) EVOH | (5) Acid anhydride F | 0.05 (Co) |
| Example 4-7 | Three-layer | COC | (95) 6IT | (5) Diester compound A | 0.05 (Co) |
| Example 4-8 | Three-layer | COC | (95) 6IT | (5) Diester compound B | 0.05 (Co) |
| Example 4-9 | Three-layer | COC | (95) 6IT | (5) Diester compound C | 0.05 (Co) |
| Example 4-10 | Three-layer | COC | (95) 6IT | (5) Diester compound D | 0.05 (Co) |

TABLE 5-continued

| | | | | | |
|---|---|---|---|---|---|
| Example 4-11 | Three-layer | COC | (95) 6IT | (5) Diamide compound E | 0.05 (Co) |
| Example 4-12 | Three-layer | COC | (95) 6IT | (5) Acid anhydride F | 0.05 (Co) |
| Example 4-13 | Three-layer | PP | (95) EVOH | (5) Diester compound A | 0.05 (Co) |
| Example 4-14 | Three-layer | PP | (95) EVOH | (5) Diester compound B | 0.05 (Co) |
| Example 4-15 | Three-layer | PP | (95) EVOH | (5) Diester compound C | 0.05 (Co) |
| Example 4-16 | Three-layer | PP | (95) EVOH | (5) Diester compound D | 0.05 (Co) |
| Example 4-17 | Three-layer | PP | (95) EVOH | (5) Diamide compound E | 0.05 (Co) |
| Example 4-18 | Three-layer | PP | (95) EVOH | (5) Acid anhydride F | 0.05 (Co) |
| Comparative Example 4-1 | Monolayer | COC | (100) COC | — | — |
| Comparative Example 4-2 | Monolayer | PP | (100) PP | — | — |
| Comparative Example 4-3 | Three-layer | COC | (100) EVOH | — | — |
| Comparative Example 4-4 | Three-layer | COC | (100) 6IT | — | — |
| Comparative Example 4-5 | Three-layer | COC | (100) Ny-MXD6 | — | 0.04 (Co) |

| | Oxygen transmission rate[1] (30th day) | Visibility of contents | Shock resistance test | Elution test TOC[2] (μg/mL) |
|---|---|---|---|---|
| Example 4-1 | Undetectable | Having haze (acceptable) | No breakage occurred in all containers | Undetectable |
| Example 4-2 | Undetectable | Having haze (acceptable) | No breakage occurred in all containers | Undetectable |
| Example 4-3 | Undetectable | Having haze (acceptable) | No breakage occurred in all containers | Undetectable |
| Example 4-4 | Undetectable | Having haze (acceptable) | No breakage occurred in all containers | Undetectable |
| Example 4-5 | Undetectable | Having haze (acceptable) | No breakage occurred in all containers | Undetectable |
| Example 4-6 | Undetectable | Having haze (acceptable) | No breakage occurred in all containers | Undetectable |
| Example 4-7 | Undetectable | Having haze (acceptable) | No breakage occurred in all containers | Undetectable |
| Example 4-8 | Undetectable | Having haze (acceptable) | No breakage occurred in all containers | Undetectable |
| Example 4-9 | Undetectable | Having haze (acceptable) | No breakage occurred in all containers | Undetectable |
| Example 4-10 | Undetectable | Having haze (acceptable) | No breakage occurred in all containers | Undetectable |
| Example 4-11 | Undetectable | Transparent (acceptable) | No breakage occurred in all containers | Undetectable |
| Example 4-12 | Undetectable | Transparent (acceptable) | No breakage occurred in all containers | Undetectable |
| Example 4-13 | Undetectable | Having haze (acceptable) | No breakage occurred in all containers | Undetectable |
| Example 4-14 | Undetectable | Having haze (acceptable) | No breakage occurred in all containers | Undetectable |
| Example 4-15 | Undetectable | Having haze (acceptable) | No breakage occurred in all containers | Undetectable |
| Example 4-16 | Undetectable | Having haze (acceptable) | No breakage occurred in all containers | Undetectable |
| Example 4-17 | Undetectable | Having haze (acceptable) | No breakage occurred in all containers | Undetectable |
| Example 4-18 | Undetectable | Having haze (acceptable) | No breakage occurred in all containers | Undetectable |
| Comparative Example 4-1 | 0.024 | Transparent (acceptable) | No breakage occurred in all containers | Undetectable |
| Comparative Example 4-2 | 0.037 | Having haze (acceptable) | No breakage occurred in all containers | Undetectable |
| Comparative Example 4-3 | 0.00007 | Transparent (acceptable) | No breakage occurred in all containers | Undetectable |
| Comparative Example 4-4 | 0.00049 | Transparent (acceptable) | No breakage occurred in all containers | Undetectable |
| Comparative Example 4-5 | Undetectable | Transparent (acceptable) | Breakage occurred in 14 of 20 | 15 |

1) Unit: mL/(0.21 atm·day·package), Detection lower limit: 5×10$^{-5}$ mL/(0.21 atm·day·package)
2) Detection lower limit: (0.1 μg/mL)

As obvious from Table 5, it was observed that the syringe of each Example had a reduced oxygen transmission rate, secured the visibility of the inside of the container, maintained a satisfactory strength even after long-term storage, and showed a reduced amount of elution from the container into the contents, compared to the syringe of each Comparative Example. It was further observed that the syringes of Examples 4-11 and 4-12 had excellent transparency to have very good visibility of the contents.

Fifth Experiment

Diester compounds A to D having tetralin rings produced in Synthesis Examples 1 to 4, and diamide compound E having a tetralin ring produced in Synthesis Example 5, and acid anhydride F having a tetralin ring produced in Synthesis Example 6 were used.

Example 5-1

95 parts by mass of an ethylene-vinyl alcohol copolymer (manufactured by Kuraray Co., Ltd., trade name: "EVAL L171B", hereinafter also abbreviated to "EVOH"), 5 parts by mass of diester compound A, and cobalt(II) stearate giving 0.05 parts by mass of cobalt were melt-kneaded with a twin-screw extruder having two 37-mm diameter screws at 220° C., extruded into a strand from the extruder head, cooled, and then pelletized to obtain oxygen-absorbing composition (1). Subsequently, a vial as an oxygen-absorbing medical multilayer molded product was produced using this oxygen-absorbing composition (1) as shown below. The performance of the resulting vial was then evaluated as described below. Table 6 shows the evaluation results.

[Production of Vial]
Under the following conditions, an injection molded product having a three-layer structure of B/A/B was prepared by injecting a thermoplastic resin constituting the resin layer (layer B) from an injection cylinder, then injecting oxygen-absorbing composition (1) constituting the oxygen-absorbing layer (layer A) from another injection cylinder simultaneously with the thermoplastic resin constituting layer B, and then injecting a necessary amount of the thermoplastic resin constituting layer B to fill the cavity of the injection mold. The resulting injection-molded product was then cooled to a predetermined temperature, was transferred to a blow mold, and was blow molded to produce a vial (bottle portion). Here, the total mass of the vial was 24 g, and the mass of layer A was 30% by mass of the total mass of the vial. The thermoplastic resin constituting layer B used was cycloolefin polymer (manufactured by Zeon Corporation, trade name: "ZEONEX 690R").

(Shape of Vial)
The vial had a total length of 89 mm, an outer diameter of 40 mmφ, and a thickness of 1.8 mm. The vial was produced with an injection blow integral-molding apparatus (manufactured by UNILOY, model: IBS 85, providing four vials).

(Conditions for Molding the Vial)
Temperature of injection cylinder for layer A: 220° C.
Temperature of injection cylinder for layer B: 280° C.
Temperature of resin flow path in injection mold: 280° C.
Blow temperature: 150° C.
Temperature of cooling water for blow mold: 15° C.

[Evaluation of Vial Performance]
The resulting vial was evaluated through measurement of the oxygen transmission rate, verification of the appearance after molding, a drop test, and an elution test in accordance with the following methods and criteria.

[Evaluation of Vial Performance]
The resulting vial was evaluated through measurement of the oxygen transmission rate, verification of the appearance after molding, a drop test, and an elution test in accordance with the following methods and criteria.

(1) Oxygen Transmission Rate (OTR) of Vial
The oxygen transmission rate was measured on the 30th day from the start of the measurement in an atmosphere of a temperature of 23° C. and relative humidities of 50% (outside the molded product) and 100% (inside the molded product) with an oxygen transmission rate measurement apparatus (manufactured by MOCON, Inc., trade name: OX-TRAN 2-21 ML). A lower measurement value indicates a higher oxygen barrier property. The detection lower limit of the measurement is an oxygen transmission rate of 5×10$^{-5}$ mL/(0.21 atm·day·package).

(2) Verification of Appearance
The visibility of the contents in the vial was visually observed. A vial allowing confirmation of the volume and the color tone of the contents and not having any problems in visibility was defined as being acceptable.

(3) Drop Test
The vial was stored at 40° C. and 90% RH for 30 days, then filled with 50 mL of pure water, and then sealed with a rubber stopper and an aluminum cap. The thus-prepared sealed container was dropped from a height of 2 m and was then investigated for the appearance of the container. The drop test was performed for twenty containers under the same conditions.

(4) Elution Test
The vial was stored at 40° C. and 90% RH for 30 days, then filled with 50 mL of pure water, and then sealed with a rubber stopper and an aluminum cap. The thus-prepared sealed container was stored at 40° C. and 60% RH for 120 days, and the total amount of carbon (hereinafter, referred to as TOC) in the pure water was then measured to determine the amount eluted impurities.

(TOC Measurement)
Apparatus: TOC-VCPH manufactured by Shimadzu Corporation
Temperature of combustion furnace: 720° C.
Gas/flow rate: high purity air, 150 mL/min at TOC meter portion
Amount injected: 150 μL
Detection limit: 1 μg/mL (5) Storage Test of Biological Medicine
(Binding Ratio Measuring Method)
The binding ratio was measured with an isothermal titration calorimeter (ITC, manufactured by GE Healthcare, "Microcal VP-ITC") at a measurement temperature of 25° C. by filling the cell with 5 μM of an antigen solution (manufactured by BIOLOGICAL Industries Ltd., "FGF1-Mouse") and adding dropwise a monoclonal antibody solution to the cell by 10 μL for each time.

(Storage Test)
The vial was filled with 1 cc of a 50 μM solution of monoclonal antibody (mAb1) (manufactured by Wako Pure Chemical Industries, Ltd., trade name: "ANTI FGF1, Monoclonal Antibody (mAb1)") and was stored under conditions of 8° C. and 50% RH for 180 days. The solvent used was a phosphate buffer (PBS, pH 7.4, one-time liquid product) manufactured by Life Technologies Japan Ltd. The binding ratio of the antibody solution before the storage test and after the storage for 180 days was measured by the above-described method, and the antibody activity retention rate after the storage was determined based on the following expression:

Antibody activity retention rate (%)=(binding ratio of antibody solution after storage for 180 days/ binding ratio of antibody solution before storage)×100

Example 5-2

A multilayer vial was produced as in Example 5-1 except that diester compound B was used instead of diester compound A, and was evaluated as in Example 5-1. The results are shown in Table 6.

Example 5-3

A multilayer vial was produced as in Example 5-1 except that diester compound C was used instead of diester compound A, and was evaluated as in Example 5-1. The results are shown in Table 6.

Example 5-4

A multilayer vial was produced as in Example 5-1 except that diester compound D was used instead of diester compound A, and was evaluated as in Example 5-1. The results are shown in Table 6.

Example 5-5

A multilayer vial was produced as in Example 5-1 except that diamide compound E was used instead of diester compound A, and was evaluated as in Example 5-1. The results are shown in Table 6.

Example 5-6

A multilayer vial was produced as in Example 5-1 except that acid anhydride F was used instead of diester compound A, and was evaluated as in Example 5-1. The results are shown in Table 6.

Example 5-7

A multilayer vial was produced as in Example 5-1 except that amorphous nylon (manufactured by Mitsubishi Engineering-Plastics Corporation, trade name: "NOVAMID X21-F07", hereinafter, also abbreviated to "6IT") was used instead of EVOH, and was evaluated as in Example 5-1. The results are shown in Table 6.

Example 5-8

A multilayer vial was produced as in Example 5-7 except that diester compound B was used instead of diester compound A, and was evaluated as in Example 5-1. The results are shown in Table 6.

Example 5-9

A multilayer vial was produced as in Example 5-7 except that diester compound C was used instead of diester compound A, and was evaluated as in Example 5-1. The results are shown in Table 6.

Example 5-10

A multilayer vial was produced as in Example 5-7 except that diester compound D was used instead of diester compound A, and was evaluated as in Example 5-1. The results are shown in Table 6.

Example 5-11

A multilayer vial was produced as in Example 5-7 except that diamide compound E was used instead of diester compound A, and was evaluated as in Example 5-1. The results are shown in Table 6.

Example 5-12

A multilayer vial was produced as in Example 5-7 except that acid anhydride F was used instead of diester compound A, and was evaluated as in Example 5-1. The results are shown in Table 6.

Comparative Example 5-1

A monolayer vial having the same shape as that of the vial in Example 5-1 was produced as in Example 5-1 except that 100 parts by mass of a cycloolefin polymer (manufactured by Zeon Corporation, trade name: "ZEONEX690R", hereinafter, also abbreviated to "COP") was used instead of oxygen-absorbing composition (1), and was evaluated as in Example 5-1. The results are shown in Table 6.

Comparative Example 5-2

A multilayer vial was produced as in Example 5-1 except that diester compound A was not used, and was evaluated as in Example 5-1. The results are shown in Table 6.

Comparative Example 5-3

A multilayer vial was produced as in Example 5-8 except that diester compound A was not used, and was evaluated as in Example 5-1. The results are shown in Table 6.

Comparative Example 5-4

A mixture prepared by dry blending of 100 parts by mass of nylon MXD6 (manufactured by Mitsubishi Gas Chemical Company Inc., trade name: "S7007") and cobalt(II) stearate giving 0.04 parts by mass of cobalt was supplied to a twin-screw extruder having two 37-mm diameter screws at a rate of 15 kg/h, melt-kneaded at a cylinder temperature of 280° C., extruded into a strand from the extruder head, cooled, and then pelletized to obtain an oxygen-absorbing composition (M). A vial was produced as in Example 5-1 except that this oxygen-absorbing composition (M) was used instead of oxygen-absorbing composition (1). The performance of the resulting vial was evaluated as in Example 5-1. The evaluation results are shown in Table 6.

TABLE 6

| | | | Composition of oxygen-absorbing layer (parts by mass) | | |
|---|---|---|---|---|---|
| | Layer structure | Inner and outer layer resin | Thermoplastic resin | Compound having tetralin ring | Transition metal |
| Example 5-1 | Three-layer | COP | (95) EVOH | (5) Diester compound A | 0.05 (Co) |
| Example 5-2 | Three-layer | COP | (95) EVOH | (5) Diester compound B | 0.05 (Co) |
| Example 5-3 | Three-layer | COP | (95) EVOH | (5) Diester compound C | 0.05 (Co) |
| Example 5-4 | Three-layer | COP | (95) EVOH | (5) Diester compound D | 0.05 (Co) |
| Example 5-5 | Three-layer | COP | (95) EVOH | (5) Diamide compound E | 0.05 (Co) |
| Example 5-6 | Three-layer | COP | (95) EVOH | (5) Acid anhydride F | 0.05 (Co) |
| Example 5-7 | Three-layer | COP | (95) 6IT | (5) Diester compound A | 0.05 (Co) |
| Example 5-8 | Three-layer | COP | (95) 6IT | (5) Diester compound B | 0.05 (Co) |
| Example 5-9 | Three-layer | COP | (95) 6IT | (5) Diester compound C | 0.05 (Co) |
| Example 5-10 | Three-layer | COP | (95) 6IT | (5) Diester compound D | 0.05 (Co) |
| Example 5-11 | Three-layer | COP | (95) 6IT | (5) Diamide compound E | 0.05 (Co) |
| Example 5-12 | Three-layer | COP | (95) 6IT | (5) Acid anhydride F | 0.05 (Co) |
| Comparative Example 5-1 | Monolayer | COP | (100) COP | — | — |
| Comparative Example 5-2 | Three-layer | COP | (100) EVOH | — | — |
| Comparative Example 5-3 | Three-layer | COP | (100) 6IT | — | — |
| Comparative Example 5-4 | Three-layer | COP | (100) Ny-MXD6 | — | 0.04 (Co) |

| | Oxygen transmission rate[1] (30th day) (cc/bottle/day/0.21 atm) | Appearance after molding | Drop test | Elution test TOC[2] (μg/mL) | Antibody retention rate (%) |
|---|---|---|---|---|---|
| Example 5-1 | Undetectable | Transparent (acceptable) | No breakage occurred in all containers | Undetectable | 75 |
| Example 5-2 | Undetectable | Transparent (acceptable) | No breakage occurred in all containers | Undetectable | 77 |
| Example 5-3 | Undetectable | Transparent (acceptable) | No breakage occurred in all containers | Undetectable | 72 |
| Example 5-4 | Undetectable | Transparent (acceptable) | No breakage occurred in all containers | Undetectable | 78 |
| Example 5-5 | Undetectable | Transparent (acceptable) | No breakage occurred in all containers | Undetectable | 80 |
| Example 5-6 | Undetectable | Transparent (acceptable) | No breakage occurred in all containers | Undetectable | 74 |
| Example 5-7 | Undetectable | Having haze (acceptable) | No breakage occurred in all containers | Undetectable | 76 |
| Example 5-8 | Undetectable | Having haze (acceptable) | No breakage occurred in all containers | Undetectable | 72 |
| Example 5-9 | Undetectable | Having haze (acceptable) | No breakage occurred in all containers | Undetectable | 78 |
| Example 5-10 | Undetectable | Having haze (acceptable) | No breakage occurred in all containers | Undetectable | 79 |
| Example 5-11 | Undetectable | Transparent (acceptable) | No breakage occurred in all containers | Undetectable | 70 |
| Example 5-12 | Undetectable | Transparent (acceptable) | No breakage occurred in all containers | Undetectable | 72 |
| Comparative Example 5-1 | 0.0382 | Transparent (acceptable) | No breakage occurred in all containers | Undetectable | 35 |
| Comparative Example 5-2 | 0.0001 | Transparent (acceptable) | No breakage occurred in all containers | Undetectable | 49 |
| Comparative Example 5-3 | 0.0007 | Transparent (acceptable) | No breakage occurred in all containers | Undetectable | 43 |
| Comparative Example 5-4 | Undetectable | Transparent (acceptable) | Breakage occurred in 14 of 20 | 15 | 79 |

1) Unit: mL/(0.21 atm·day·package), Detection lower limit: 5×10⁻⁵ mL/(0.21 atm·day·package)
2) Detection lower limit: (0.1 μg/mL)

As obvious from Table 6, the oxygen transmission rate could be reduced in each Example, compared to each Comparative Example. It was also confirmed that the oxygen permeation was low to significantly prevent oxidation degradation of the biological medicine, the biological medicine could be protected from a shock from outside even in a long-term storage, contamination of the biological medicine with impurities could be effectively prevented, and a reduction in drug efficacy after storage could be suppressed.

Note that the present application is based on the following Japanese Patent Applications, the contents of which are incorporated herein by reference:
Japanese Patent Application (Patent Application No. 2013-044754) filed with the Japanese Patent Office on Mar. 6, 2013;
Japanese Patent Application (Patent Application No. 2013-044734) filed with the Japanese Patent Office on Mar. 6, 2013;
Japanese Patent Application (Patent Application No. 2013-044755) filed with the Japanese Patent Office on Mar. 6, 2013;
Japanese Patent Application (Patent Application No. 2013-044737) filed with the Japanese Patent Office on Mar. 6, 2013; and
Japanese Patent Application (Patent Application No. 2013-044740) filed with the Japanese Patent Office on Mar. 6, 2013.

INDUSTRIAL APPLICABILITY

The oxygen-absorbing medical multilayer container of the present invention at least has an excellent oxygen absorbing property and can, therefore, absorb oxygen regardless of the presence or absence of water in the article to be stored, and the multilayer container suppresses an increase in the strength of odor after oxygen absorption and can be, therefore, effectively used, in particular, for, for example, medicinal products and health foods. Moreover, the oxygen-absorbing multilayer laminate and other products of the present invention are not responsive to a metal detector and therefore can be widely and effectively used in packaging materials, containers, etc. that are required to be inspected with a metal detector for metals, metal pieces, etc. from the outside.

What is claimed is:
1. An oxygen-absorbing medical multilayer container comprising at least three layers comprising:
   a first resin layer containing a thermoplastic resin (b1);
   an oxygen-absorbing layer containing an oxygen-absorbing composition; and
   a second resin layer containing a thermoplastic resin (b2), in this order, wherein
   the oxygen-absorbing composition comprises a compound having a tetralin ring, a transition metal catalyst, and a thermoplastic resin (a), and
   the compound having a tetralin ring is a compound having a tetralin ring represented by Formula (1A), a compound having a tetralin ring represented by Formula (1B) or a compound having a tetralin ring represented by Formula (2-1):

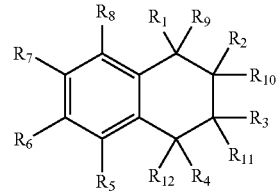

(1A)

where, in Formula (1A), $R_1$ to $R_{12}$ each independently represent a hydrogen atom or a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, an imide group, a substituent represented by Formula (1a), and a substituent represented by Formula (1b), which each optionally further have a substituent; $R_1$ to $R_{12}$ do not form a ring by bonding of two or more thereof; and at least one hydrogen atom is bonded to a benzylic position of the tetralin ring; and $R_1$ to $R_{12}$ satisfy the following requirements (A) or (B);
   (A) one or more monovalent substituents represented by Formula (2) are bonded to the aromatic ring of the tetralin ring, and one or more monovalent substituents represented by Formula (2) are bonded to the aliphatic ring of the tetralin ring; and
   (B) two or more monovalent substituents represented by Formula (2) are bonded to the aromatic ring of the tetralin ring:

—C(=O)X    (2)

where, in Formula (2), X represents one selected from the group consisting of a hydrogen atom, a hydroxy group, an alkyl group, an alkoxy group, a monoalkylamino group, and a dialkylamino group, and a plurality of X may be the same or different:

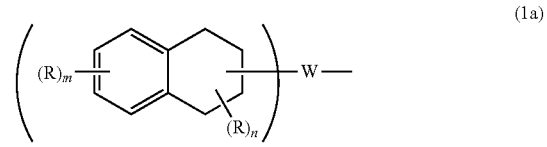

(1a)

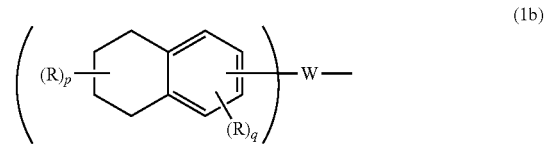

(1b)

where, in Formulae (1a) or (1b), R each independently represents a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, and an imide group, which each optionally further have a substituent; two of the substituents each represented by R are optionally bonded to each other to form a ring; W represents a bond or a bivalent organic group, the bivalent organic group being at least one selected from the group consisting of an aromatic hydrocarbon group, a saturated or unsaturated alicyclic hydrocarbon group, a linear or branched saturated or unsaturated aliphatic hydrocarbon group and a heterocyclic group, —C(=O)—, —OC(=O)—, —N(H)C(=O)—, and an arbitrary combination thereof; m represents an integer of 0 to 4; n represents an integer of 0 to 7; p represents an integer of 0 to 8; and q represents an integer of 0 to 3:

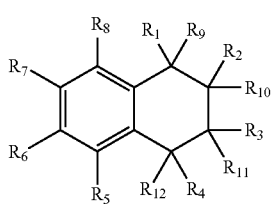

(1B)

where, in Formula (1B), $R_1$ to $R_{12}$ each independently represent a hydrogen atom or a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, an imide group, a substituent represented by Formula (1a), and a substituent represented by Formula (1b), which each optionally further have a substituent; two of the substituents represented by $R_1$ to $R_{12}$ are optionally bonded to each other to form a ring; and at least one hydrogen atom is bonded to a benzylic positions of the tetralin ring, with the proviso that the monovalent substituent being at least one selected from the group consisting of the substituent represented by Formula (1a) and the substituent represented by Formula (1b), which each optionally further have a substituent; and wherein, in Formulae (1a) and (1b), R, W, m, n, p and q are as defined above:

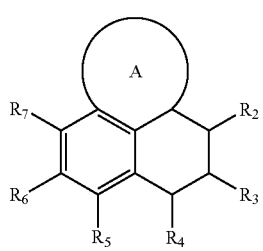

(2-1)

where, in Formula (2-1), $R_2$ to $R_7$ each independently represent a hydrogen atom or a monovalent substituent, the monovalent substituent being at least one selected from the group consisting of a halogen atom, an alkyl group, an alkenyl group, an alkynyl group, an aryl group, a heterocyclic group, a cyano group, a hydroxy group, a carboxyl group, an ester group, an amide group, a nitro group, an alkoxy group, an aryloxy group, an acyl group, an amino group, a thiol group, an alkylthio group, an arylthio group, a heterocyclic thio group, an imide group, the substituent represented by Formula (1a), and the substituent represented by Formula (1b), which each optionally further have a substituent; two of the substituents represented by $R_2$ to $R_7$ are optionally bonded to each other to form a ring; and at least one hydrogen atom is bonded to a benzylic position of the tetralin ring; and arc A represents a substituted or unsubstituted aromatic, heterocyclic, or acid anhydride ring having 4 to 7 carbon atoms; and wherein, in Formulae (1a) and (1b), R, W, m, n, p and q are as defined above.

2. The oxygen-absorbing medical multilayer container according to claim 1, wherein the compound having a tetralin ring is a compound having a tetralin ring represented by Formula (1A).

3. The oxygen-absorbing medical multilayer container according to claim 1, wherein the compound having a tetralin ring is a compound having a tetralin ring represented by Formula (1B).

4. The oxygen-absorbing medical multilayer container according to claim 1, wherein the compound having a tetralin ring has two or more tetralin rings.

5. The oxygen-absorbing medical multilayer container according to claim 1, wherein a proportion of the amount of the compound having a tetralin ring to the total amount of the compound having a tetralin ring and the thermoplastic resin (a) in the oxygen-absorbing composition is 1% to 30% by mass.

6. The oxygen-absorbing medical multilayer container according to claim 1, wherein the transition metal catalyst contains at least one transition metal selected from the group consisting of manganese, iron, cobalt, nickel, and copper.

7. The oxygen-absorbing medical multilayer container according to claim 1, wherein the transition metal catalyst is contained in an amount of 0.001 to 10 parts by mass in terms of the transition metal amount, in the oxygen-absorbing composition, based on 100 parts by mass of the total amount of the compound having a tetralin ring and the thermoplastic resin (a).

8. The oxygen-absorbing medical multilayer container according to claim 1, wherein the thermoplastic resin (a) in the oxygen-absorbing composition is at least one selected from the group consisting of a polyolefin, a polyester, a polyamide, an ethylene-vinyl alcohol copolymer, a plant-derived resin, and a chlorine-containing resin.

9. The oxygen-absorbing medical multilayer container according to claim 1, wherein
the thermoplastic resin (b1) is a polyolefin (PO1); and
the thermoplastic resin (b2) is a polyolefin (PO2).

10. The oxygen-absorbing medical multilayer container according to claim 1, wherein
the thermoplastic resin (b1) is a polyester (PES1); and
the thermoplastic resin (b2) is a polyester (PES2).

11. The oxygen-absorbing medical multilayer container according to claim 10, wherein
at least one of the polyester (PES1) and the polyester (PES2) comprises dicarboxylic acid units, where 70 mol % or more of the dicarboxylic acid units are derived from one or more dicarboxylic acids selected from the group consisting of terephthalic acid, isophthalic acid, 1,3-naphthalenedicarboxylic acid, 1,4-naphthalenedicarboxylic acid, 1,5-naphthalenedicarboxylic acid, 2,6-naphthalenedicarboxylic acid, and 2,7-naphthalenedicarboxylic acid, and ester-forming derivatives thereof.

12. The oxygen-absorbing medical multilayer container according to claim 1, wherein the oxygen-absorbing medical multilayer container is an oxygen-absorbing prefilled syringe accommodating a drug in a sealed condition in advance and allowing the drug to be dispensed by releasing the sealed condition when the syringe is used.

13. A method for storing a biological medicine, comprising storing the biological medicine in the oxygen-absorbing medical multilayer container according to claim 1.

14. The oxygen-absorbing medical multilayer container according to claim 1, wherein the compound having a tetralin ring is a compound having a tetralin ring represented by Formula (2-1).

* * * * *